(12) United States Patent
Machacek et al.

(10) Patent No.: US 8,344,144 B2
(45) Date of Patent: Jan. 1, 2013

(54) INHIBITORS OF JANUS KINASES

(75) Inventors: Michelle Machacek, Brookline, MA (US); Gabriela de Almeida, Brookline, MA (US); Jonathan B. Grimm, Newton, MA (US); Rachel N. MacCoss, Brookline, MA (US); Eric Romeo, Allston, MA (US); Tony Siu, Brookline, MA (US); Catherine White, Newton Center, LA (US); Kevin Wilson, West Newton, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/999,342

(22) PCT Filed: Jun. 8, 2009

(86) PCT No.: PCT/US2009/046597
§ 371 (c)(1),
(2), (4) Date: Dec. 16, 2010

(87) PCT Pub. No.: WO2009/155156
PCT Pub. Date: Dec. 23, 2009

(65) Prior Publication Data
US 2011/0082136 A1 Apr. 7, 2011

Related U.S. Application Data

(60) Provisional application No. 61/132,963, filed on Jun. 18, 2008.

(51) Int. Cl.
*C07D 471/02* (2006.01)
*A61K 31/395* (2006.01)
(52) U.S. Cl. ........................................ 546/113; 514/300
(58) Field of Classification Search .................. 546/113; 514/300
See application file for complete search history.

(56) References Cited

U.S. PATENT DOCUMENTS

| 3,963,750 A | 6/1976 | Goudie |
| 7,125,896 B2 | 10/2006 | Faull et al. |
| 2007/0249670 A1 | 10/2007 | Evans et al. |

OTHER PUBLICATIONS

Kubinyi (3D QSAR in Drug Design: Ligand-Protein Interactions and Molecular Similarity, vol. 2-3, Springer, 1998, 800 pages).*
Malerich et al. (Bioorg. Med. Chem. Lett. 20 (2010) 7454-7457).*
Wermuth, The Practice of Medicinal Chemsitry, 2d ed. (2003), 768 pages. Chapters 9-10 provided.*
Huang et al. (CAPLUS Abstract of WO 2008024980).*
Cannon, "Analog Design" in Burger's Medicinal Chemistry and Drug Discovery, 6th ed. 2003, Wiley, pp. 687-714.*

* cited by examiner

*Primary Examiner* — Robert Havlin
(74) *Attorney, Agent, or Firm* — Laura M. Ginkel; David A. Muthard

(57) ABSTRACT

The instant invention provides for compounds that inhibit the four known mammalian JAK kinases (JAK1, JAK2, JAK3 and TYK2) and PDK1. The invention also provides for compositions comprising such inhibitory compounds and methods of inhibiting the activity of JAK1, JAK2, JAK3, TYK2 and PDK1 by administering the compound to a patient in need of treatment for myeloproliferative disorders or cancer.

6 Claims, No Drawings

INHIBITORS OF JANUS KINASES

BACKGROUND OF THE INVENTION

Janus kinase (JAK) is a family of intracellular non-receptor tyrosine kinases, ranging from 120-140 kDa, that transduce cytokine-mediated signals via the JAK-STAT pathway. The JAK family plays a role in the cytokine-dependent regulation of proliferation and function of cells involved in immune response. Currently, there are four known mammalian JAK family members: JAK1, JAK2, JAK3 and TYK2.

JAK1, JAK2 and TYK2 are ubiquitously expressed whereas JAK3 is expressed in the myeloid and lymphoid lineages. The JAK family members are non-receptor tyrosine kinases that associate with many hematopoietin cytokines, receptor tyrosine kinases and GPCR's. JAK1−/− mice were found to be developmentally similar to the JAK1+/+ although they weighed 40% less than the wild-type and failed to nurse at birth. These pups were not viable and died within 24 hours of birth (Meraz et al Cell, 1998, 373-383). JAK1 deficiency led to reduced number of thymocytes, pre-B cells and mature T and B lymphocytes. TYK2(−/−) mice, on the other hand, are viable, demonstrating subtle defects in their response to IFN-α/β and IL-10 and profound defects to the response of IL-12 and LPS.

The breast cancer susceptibility protein (BRCA1) acts as a tumor suppressor and contributes to cell proliferation, cycle regulation, as well as DNA damage and repair. BRCA1 (−/−) mice develop normally but die by 7.5 days post embryo suggesting a key role of BRCA1 for development. Mice in which the BRCA1 protein was overexpressed led to inhibition of cell growth and sensitized cells to cytotoxic reagents. In the human prostate cancer cell line Du-145 (Gao FEBS Letters 2001, 488, 179-184), enhanced expression of BRCA1 was found to correlate with constitutive activation of STAT3 as well as activation of JAK1 and JAK2. Moreover, antisense oligonucleotides selective for STAT3 led to significant inhibition of cell proliferation and apoptosis in Du-145 cells. This data supports the potential utility of JAK1 and JAK2 inhibitors in the treatment of prostate cancer.

Campbell et al (Journal of Biological Chemistry 1997, 272, 2591-2594) as reported that STAT3 is constitutively activated v-Src transformed cells. To test whether STAT3 activation resulted via signaling through the JAK-STAT pathway, three fibroblast cell lines (NIH3T3, Balb/c, and 3Y1) were transformed with v-Src. The level of JAK1 phosphorylation in NIH3T3 cells was markedly increased in cells overexpressed with v-Src or mutant c-Src (Y527F) compared to those in the less transforming c-Src. This result correlated with increased JAK1 enzymatic activity. Similar results were observed with JAK2 albeit to a lesser extent. These results are consistent with constitutive activation of JAK1 and possibly JAK2 which contribute to the hyperactivation of STAT3 in Src-transformed cells.

Asthma is a disease that is increasing in prevalence and results in "airway obstruction, airway hyperresponsiveness, and airway inflammation and remodeling" (Perris. The Journal of Clinical Investigation 2002, 109, 1279-1283). A common cause is the inappropriate immune responses to environmental antigens usually involving CD4+ T helper cells (TH2) which are triggered from cytokines IL-4, IL-5, IL-6, IL-10, and IL-13 which signal through JAK1/JAK3-STAT6 pathway. Th1 cells are thought to be involved with the "delayed-type hypersensitivity responses" which secrete IL-2, IFN-γ, and TNF-β and signal through the JAK2/TYK2-STAT4 pathway. STAT6 (−/−) mice were protected from AHR when challenged with environmental antigens and showed no increase in IgE levels or the quantity of mucous containing cells.

JAK2 is a cytoplasmic protein-tyrosine kinase that catalyzes the transfer of the gamma-phosphate group of adenosine triphosphate to the hydroxyl groups of specific tyrosine residues in signal transduction molecules. JAK2 mediates signaling downstream of cytokine receptors after ligand-induced autophosphorylation of both receptor and enzyme. The main downstream effectors of JAK2 are a family of transcription factors known as signal transducers and activators of transcription (STAT) proteins. Studies have disclosed an association between an activating JAK2 mutation (JAK2V617F) and myeloproliferative disorders. The myeloproliferative disorders, a subgroup of myeloid malignancies, are clonal stem cell diseases characterized by an expansion of morphologically mature granulocyte, erythroid, megakaryocyte, or monocyte lineage cells. Myeloproliferative disorders (MPD) include polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), juvenile myelomonocytic leukemia (JMML) and systemic mast cell disease (SMCD). It has been suggested that abnormalities in signal transduction mechanisms, including constitutive activation of protein tyrosine kinases, initiate MPD.

JAK3 associates with the common gamma chain of the extracellular receptors for the following interleukins: IL-2, IL-4, IL-7, IL-9 and IL-15. A JAK3 deficiency is associated with an immune compromised (SCID) phenotype in both rodents and humans. The SCID phenotype of JAK3−/− mammals and the lymphoid cell specific expression of JAK3 are two favorable attributes of a target for an immune suppressant. Data suggests that inhibitors of JAK3 could impede T-cell activation and prevent rejection of grafts following transplant surgery, or to provide therapeutic benefit to patients suffering autoimmune disorders.

PDK1 signaling regulates multiple critical steps in angiogenesis. Inhibitors of the activity of PDK1 are thus useful in the treatment of cancer, in particular cancers associated with deregulated activity of the PTEN/PI3K pathway including, but not limited to PTEN loss of function mutations and receptor tyrosine kinase gain of function mutations.

SUMMARY OF THE INVENTION

The instant invention provides for compounds that inhibit mammalian JAK kinases (such as JAK1, JAK2, JAK3 and TYK2) and PDK1. The invention also provides for compositions comprising such inhibitory compounds and methods of inhibiting the activity of JAK1, JAK2, JAK3 TYK2 and PDK1 by administering the compound to a patient in need of treatment for myeloproliferative disorders or cancer. One embodiment of the invention is illustrated by a compound of formula I or II, and the pharmaceutically acceptable salts and stereoisomers thereof:

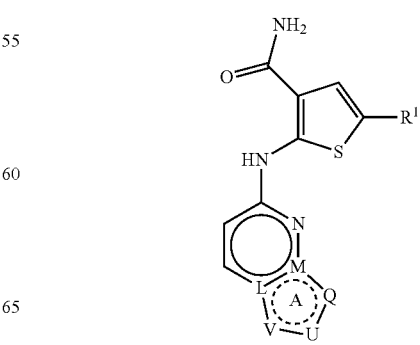

I

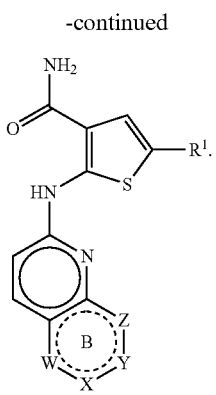

DETAILED DESCRIPTION OF THE INVENTION

The instant invention provides for compounds that inhibit the four known mammalian JAK kinases (JAK1, JAK2, JAK3 and TYK2) and PDK1. The invention also provides for compositions comprising such inhibitory compounds and methods of inhibiting the activity of JAK1, JAK2, JAK3, TYK2 and PDK1 by administering the compound to a patient in need of treatment for myeloproliferative disorders or cancer. One embodiment of the invention is illustrated by a compound of formula I or II:

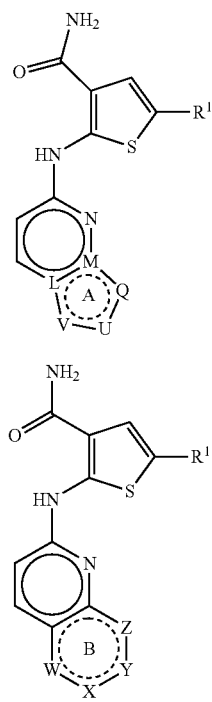

wherein rings A and B are either saturated, partially saturated or unsaturated;
W is N, $NR^6$, CH or $CH_2$;
X is N, $NR^6$ or $CR^2$;
Y is N, $NR^6$, CH or $CH_2$;
Z is N, $NR^6$, CH, $CH_2$ or C=O;
L is N or C;
M is N or C;
Q is $CR^3$, $CHR^3$, N, NH, S or C=O;
U is $CR^4$, $CHR^4$, O, N, $NR^5$, or S;
V is $CR^6$, $CR^6R^7$, N, $NR^6$, S or C=O;
$R^1$ is aryl or heteroaryl, wherein said aryl and heteroaryl groups are optionally substituted on either the carbon or the heteroatom with one to three substituents independently selected from the group consisting of halo, hydroxyl, cyano, $C_{1-6}$ alkyl and heterocyclyl, wherein said alkyl group is optionally substituted with hydroxyl or cyano, and said heterocyclyl group is optionally substituted with halo;
$R^2$ is hydrogen, halo, hydroxyl, $C_{1-6}$ alkyl or $O(C_{1-6}$ alkyl);
$R^3$ is hydrogen, halo, $C_{1-6}$ alkyl, $C_{2-6}$ alkenyl or heteroaryl, wherein said alkenyl group is optionally substituted with one to three halo or hydroxyl;
$R^4$ is hydrogen, halo, $C_{1-6}$ alkyl, $C_{3-6}$ cycloalkyl, heteroaryl, heterocyclyl, (C=O)heterocyclyl, (C=O)NH($C_{3-6}$ cycloalkyl) or (C=O)$NR^6R^7$, wherein said alkyl groups are optionally substituted with one to three halo, hydroxyl, heterocyclyl or $C_{3-6}$ cycloalkyl and said heterocyclyl groups are optionally substituted on either the carbon or the heteroatom with hydroxyl or $CH_2OH$;
$R^5$ is hydrogen, halo, cyano, $C_{1-6}$ alkyl, ($C_{1-6}$ alkyl)$OR^6$, heterocyclyl, $CH_2$-heterocyclyl or $CH_2$-heteroaryl, wherein said alkyl groups are optionally substituted with one to three substituents independently selected from the group consisting of halo, hydroxyl and $NR^6R^7$, and said heterocyclyl groups are optionally substituted on either the carbon or the heteroatom with $C_{1-6}$ alkyl;
$R^6$ is hydrogen or $C_{1-6}$ alkyl; wherein said alkyl group is optionally substituted with hydroxyl or $C_{3-6}$ cycloalkyl;
$R^7$ is hydrogen or $C_{1-6}$ alkyl; wherein said alkyl group is optionally substituted with hydroxyl;
or a pharmaceutically acceptable salt thereof.

In an embodiment of the invention, W is N, NH, CH or $CH_2$.
In an embodiment of the invention, X is N, NH or $CR^2$;
In an embodiment of the invention, Y is N, NH, CH or $CH_2$;
In an embodiment of the invention, Z is N, NH, CH, $CH_2$ or C=O;
In an embodiment of the invention, L is C.
In an embodiment of the invention, M is N. In another embodiment of the invention, M is C.
In an embodiment of the invention, Q is $CR^3$, $CHR^3$, N or NH. In a class of the invention, Q is $CR^3$. In another class of the invention, Q is N or NH. In another class of the invention, Q is $CHR^3$.
In an embodiment of the invention, U is $CR^4$ or $NR^5$. In a class of the invention, U is $CR^4$. In another class of the invention, U is $NR^5$.
In an embodiment of the invention, V is N, $NR^6$ or C=O. In a class of the invention, V is N or NH. In another class of the invention, V is N. In another class of the invention, V is C=O.
In an embodiment of the invention, $R^1$ is aryl, wherein said aryl group is substituted with one to three substituents independently selected from the group consisting of halo and $C_{1-6}$ alkyl, wherein said alkyl group is optionally substituted with hydroxyl. In a class of the invention, $R^1$ is phenyl, wherein said phenyl group is substituted with one to three substituents independently selected from the group consisting of halo and $C_{1-6}$ alkyl, wherein said alkyl group is optionally substituted with hydroxyl.
In an embodiment of the invention, $R^3$ is hydrogen.
In an embodiment of the invention, $R^4$ is $C_{1-6}$ alkyl, wherein said alkyl group is optionally substituted with hydroxyl or heterocyclyl, and said heterocyclyl group is optionally substituted with hydroxyl or $CH_2OH$. In a class of the invention, $R^4$ is $C_{1-6}$ alkyl, wherein said alkyl group is optionally substituted with hydroxyl. In another class of the invention, $R^4$ is $C_{1-6}$ alkyl, wherein said alkyl group is optionally substituted with heterocyclyl.

In an embodiment of the invention, $R^5$ is $C_{1-6}$ alkyl, wherein said alkyl group is optionally substituted with one to three hydroxyl. In a class of the invention, $R^5$ is $C_{1-6}$ alkyl, wherein said alkyl group is substituted with hydroxyl.

Reference to the preferred embodiments set forth above is meant to include all combinations of particular and preferred groups unless stated otherwise.

Specific embodiments of the present invention include, but are not limited to:

5-[2,6-Difluoro-4-(1-hydroxy-1-methylethyl)phenyl]-2-{[6-(2-hydroxyethyl)-5-oxo-6,7-dihydro-5H-pyrrolo[3,4-b]pyridin-2-yl]amino}thiophene-3-carboxamide;

5-[2,6-difluoro-4-(1-hydroxy-1-methylethyl)phenyl]-2-[(5-oxo-6,7-dihydro-5H-pyrrolo[3,4-b]pyridin-2-yl)amino]thiophene-3-carboxamide;

5-[2,6-difluoro-4-(1-hydroxy-1-methylethyl)phenyl]-2-{[6-(2-methoxyethyl)-5-oxo-6,7-dihydro-5H-pyrrolo[3,4-b]pyridin-2-yl]amino}thiophene-3-carboxamide;

5-[2,6-difluoro-4-(1-hydroxy-1-methylethyl)phenyl]-2-({6-[(2S)-2-hydroxypropyl]-5-oxo-6,7-dihydro-5H-pyrrolo[3,4-b]pyridin-2-yl}amino)thiophene-3-carboxamide;

5-[2,6-difluoro-4-(1-hydroxy-1-methylethyl)phenyl]-2-({6-[(2R)-2-hydroxypropyl]-5-oxo-6,7-dihydro-5H-pyrrolo[3,4-b]pyridin-2-yl}amino)thiophene-3-carboxamide;

5-[2,6-difluoro-4-(1-hydroxy-1-methylethyl)phenyl]-2-({6-[2-(dimethylamino)ethyl]-5-oxo-6,7-dihydro-5H-pyrrolo[3,4-b]pyridin-2-yl}amino)thiophene-3-carboxamide;

5-[2,6-Difluoro-4-(1-hydroxy-1-methylethyl)phenyl]-2-[(6-methyl-5-oxo-6,7-dihydro-5H-pyrrolo[3,4-b]pyridin-2-yl)amino]thiophene-3-carboxamide;

5-[2-fluoro-4-(1-hydroxy-1-methylethyl)phenyl]-2-[(6-methyl-5-oxo-6,7-dihydro-5H-pyrrolo[3,4-b]pyridin-2-yl)amino]thiophene-3-carboxamide;

5-[4-(1-hydroxy-1-methylethyl)phenyl]-2-[(6-methyl-5-oxo-6,7-dihydro-5H-pyrrolo[3,4-b]pyridin-2-yl)amino]thiophene-3-carboxamide;

2-[(6-methyl-5-oxo-6,7-dihydro-5H-pyrrolo[3,4-b]pyridin-2-yl)amino]-5-(6-morpholin-4-ylpyridin-3-yl)thiophene-3-carboxamide;

5-(4-chlorophenyl)-2-[(6-methyl-5-oxo-6,7-dihydro-5H-pyrrolo[3,4-b]pyridin-2-yl)amino]thiophene-3-carboxamide;

5-(4-fluorophenyl)-2-[(6-methyl-5-oxo-6,7-dihydro-5H-pyrrolo[3,4-b]pyridin-2-yl)amino]thiophene-3-carboxamide;

2-[(6-methyl-5-oxo-6,7-dihydro-5H-pyrrolo[3,4-b]pyridin-2-yl)amino]-5-(2,4,6-trifluorophenyl)thiophene-3-carboxamide;

5-[4-(1-cyano-1-methylethyl)phenyl]-2-[(6-methyl-5-oxo-6,7-dihydro-5H-pyrrolo[3,4-b]pyridin-2-yl)amino]thiophene-3-carboxamide;

5-[4-(3-fluorooxetan-3-yl)phenyl]-2-[(6-methyl-5-oxo-6,7-dihydro-5H-pyrrolo[3,4-b]pyridin-2-yl)amino]thiophene-3-carboxamide;

5-[2,6-difluoro-4-(1-hydroxy-1-methylethyl)phenyl]-2-[(6-isopropyl-5-oxo-6,7-dihydro-5H-pyrrolo[3,4-b]pyridin-2-yl]amino)thiophene-3-carboxamide;

5-[2,6-Difluoro-4-(1-hydroxy-1-methylethyl)phenyl]-2-({6-[(3-methyloxetan-3-yl)methyl]-5-oxo-6,7-dihydro-5H-pyrrolo[3,4-b]pyridin-2-yl}amino)thiophene-3-carboxamide;

5-[2,6-difluoro-4-(1-hydroxy-1-methylethyl)phenyl]-2-{[6-(1,3-oxazol-2-ylmethyl)-5-oxo-6,7-dihydro-5H-pyrrolo pyridin-2-yl]amino}thiophene-3-carboxamide;

5-[2,6-Difluoro-4-(1-hydroxy-1-methylethyl)phenyl]-2-[(6-oxetan-3-yl-5-oxo-6,7-dihydro-5H-pyrrolo[3,4-b]pyridin-2-yl)amino]thiophene-3-carboxamide;

5-[2,6-Difluoro-4-(1-hydroxy-1-methylethyl)phenyl]-2-[(6-methyl-7-oxo-6,7-dihydro-5H-pyrrolo[3,4-]pyridin-2-yl)amino]thiophene-3-carboxamide;

2-[(6-methyl-7-oxo-6,7-dihydro-5H-pyrrolo[3,4-b]pyridin-2-yl)amino]-5-(6-morpholin-4-ylpyridin-3-yl)thiophene-3-carboxamide;

5-[2,6-Difluoro-4-(1-hydroxy-1-methylethyl)phenyl]-2-[(5,5-dimethyl-5,7-dihydrofuro[3,4-b]pyridin-2-yl)amino]thiophene-3-carboxamide;

5-[2,6-Difluoro-4-(1-hydroxy-1-methylethyl)phenyl]-2-{[2-(1-hydroxyethyl)-1H-imidazo[4,5-b]pyridin-5-yl]amino}thiophene-3-carboxamide;

5-[2,6-difluoro-4-(1-hydroxy-1-methylethyl)phenyl]-2-{[2-(trifluoromethyl)-3H-imidazo[4,5-b]pyridin-5-yl]amino}thiophene-3-carboxamide;

5-[2,6-difluoro-4-(1-hydroxy-1-methylethyl)phenyl]-2-[(2-methyl-1H-imidazo[4,5-b]pyridin-5-yl)amino]thiophene-3-carboxamide;

5-[2,6-Difluoro-4-(1-hydroxy-1-methylethyl)phenyl]-2-{[2-(morpholin-4-ylmethyl)-1H-imidazo[4,5-b]pyridin-5-yl]amino}thiophene-3-carboxamide;

5-[2,6-Difluoro-4-(1-hydroxy-1-methylethyl)phenyl]-2-(1H-[1,2,3]triazolo[4,5-b]pyridin-5-ylamino)thiophene-3-carboxamide;

5-[2,6-Difluoro-4-(1-hydroxy-1-methylethyl)phenyl]-2-{[1-(2-hydroxy-2-methylpropyl)-1H-[1,2,3]triazolo[4,5-b]pyridin-5-yl]amino}thiophene-3-carboxamide;

5-[2,6-Difluoro-4-(1-hydroxy-1-methylethyl)phenyl]-2-[(2-methyl[1,3]thiazolo[4,5-b]pyrazin-6-yl)amino]thiophene-3-carboxamide;

5-(4-(1-Hydroxy-1-methylethyl)phenyl)-2-[(2-methoxypyrido[2,3-b]pyrazin-6-yl)amino]thiophene-3-carboxamide;

5-[2,6-difluoro-4-(1-hydroxy-1-methylethyl)phenyl]-2-(1H-pyrazolo[4,3-b]pyridin-5-ylamino)thiophene-3-carboxamide;

5-[2,6-difluoro-4-(1-hydroxy-1-methylethyl)phenyl]-2-(1H-pyrrolo[3,2-b]pyridin-5-ylamino)thiophene-3-carboxamide;

5-(2-fluoro-4-(1-hydroxy-1-methylethyl)phenyl)-2-((2-methoxypyrido[3,2-d]pyrimidin-6-yl)amino)-3-thiophenecarboxamide;

5-(4-(1-hydroxy-1-methylethyl)phenyl)-2-(thieno[3,2-b]pyridin-5-ylamino)-3-thiophenecarboxamide;

5-(4-(1-hydroxy-1-methylethyl)phenyl)-2-(1H-pyrazolo[4,3-b]pyridin-5-ylamino)-3-thiophenecarboxamide;

5-(4-(1-hydroxy-1-methylethyl)phenyl)-2-(thieno[2,3-b]pyridin-6-ylamino)-3-thiophenecarboxamide;

5-(4-(1-hydroxy-1-methylethyl)phenyl)-2-((6-methoxy-1,5-naphthyridin-2-ylamino)-3-thiophenecarboxamide;

5-(4-(1-hydroxy-1-methylethyl)phenyl-2-methoxypyrido[3,2-d]pyrimidin-6-yl)amino)-3-thiophenecarboxamide;

5-[2,6-difluoro-4-(1-hydroxy-1-methylethyl)phenyl]-2-(imidazo[1,2-b]pyridazin-6-ylamino)thiophene-3-carboxamide;

5-[2,6-difluoro-4-(1-hydroxy-1-methylethyl)phenyl]-2-[(2-methylimidazo[1,2-b]pyridazin-6-yl)amino]thiophene-3-carboxamide;

5-[2,6-difluoro-4-(1-hydroxy-1-methylethyl)phenyl]-2-([1,2,4]triazolo[4,3-b]pyridazin-6-ylamino)thiophene-3-carboxamide;

5-[2,6-difluoro-4-(1-hydroxy-1-methylethyl)phenyl]-2-(pyrazolo[1,5-a]pyrimidin-5-ylamino)thiophene-3-carboxamide;

5-[2,6-difluoro-4-(1-hydroxy-1-methylethyl)phenyl]-2-[(8-oxo-7,8-dihydro-1,7-naphthyridin-2-yl)amino]thiophene-3-carboxamide;

5-[2-fluoro-4-(1-hydroxy-1-methylethyl)phenyl]-2-[(8-oxo-7,8-dihydro-1,7-naphthyridin-2-yl)amino]thiophene-3-carboxamide;

5-[2,6-Difluoro-4-(1-hydroxy-1-methylethyl)phenyl]-2-{[2-(1-hydroxy-1-methylethyl)imidazo[1,2-b]pyridazin-6-yl]amino}thiophene-3-carboxamide;

2-{[2-(1-hydroxy-1-methylethyl)imidazo[1,2-b]pyridazin-6-yl]amino}-5-(6-morpholin-4-ylpyridin-3-yl)thiophene-3-carboxamide;

5-[2-fluoro-4-(1-hydroxy-1-methylethyl)phenyl]-2-{[2-(1-hydroxy-1-methylethyl)imidazo[1,2-b]pyridazin-6-yl]amino}thiophene-3-carboxamide;

5-[2,6-Difluoro-4-(1-hydroxy-1-methylethyl)phenyl]-2-{[2-(2-furyl)imidazo[1,2-b]pyridazin-6-yl]amino}thiophene-3-carboxamide;

5-[2,6-difluoro-4-(1-hydroxy-1-methylethyl)phenyl]-2-{[2-(2-thienyl)imidazo[1,2-b]pyridazin-6-yl]amino}thiophene-3-carboxamide;

2-[(2-cyclopropylimidazo[1,2-b]pyridazin-6-yl)amino]-5-[2,6-difluoro-4-(1-hydroxy-1-methylethyl)phenyl]thiophene-3-carboxamide;

5-[2,6-Difluoro-4-(1-hydroxy-1-methylethyl)phenyl]-2-({2-[(3-hydroxyazetidin-1-yl)carbonyl]imidazo[1,2-b]pyridazin-6-yl}amino)thiophene-3-carboxamide;

6-({3-(Aminocarbonyl)-5-[2,6-difluoro-4-(1-hydroxy-1-methylethyl)phenyl]-2-thienyl}amino)-N-isopropylimidazo[1,2-b]pyridazine-2-carboxamide;

6-({3-(aminocarbonyl)-5-[2,6-difluoro-4-(1-hydroxy-1-methylethyl)phenyl]-2-thienyl}amino)-N-cyclobutylimidazo[1,2-b]pyridazine-2-carboxamide;

6-({3-(aminocarbonyl)-5-[2,6-difluoro-4-(1-hydroxy-1-methylethyl)phenyl]-2-thienyl}amino)-N-(1-cyclopropylethyl)imidazo[1,2-b]pyridazine-2-carboxamide;

5-[2,6-difluoro-4-(1-hydroxy-1-methylethyl)phenyl]-2-{[2-(morpholin-4-ylcarbonyl)imidazo[1,2-b]pyridazin-6-yl]amino}thiophene-3-carboxamide, 5-[2,6-Difluoro-4-(1-hydroxy-1-methylethyl)phenyl]-2-([1,2,5]oxadiazolo[3,4-b]pyridin-5-ylamino)thiophene-3-carboxamide;

5-[2,6-Difluoro-4-(1-hydroxy-1-methylethyl)phenyl]-2-([1,2,5]thiadiazolo[3,4-b]pyridin-5-ylamino)thiophene-3-carboxamide;

or a pharmaceutically acceptable salt thereof.

Also included within the scope of the present invention is a pharmaceutical composition which is comprised of a compound of Formula I or II as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted. For example the following is within the scope of the instant invention:

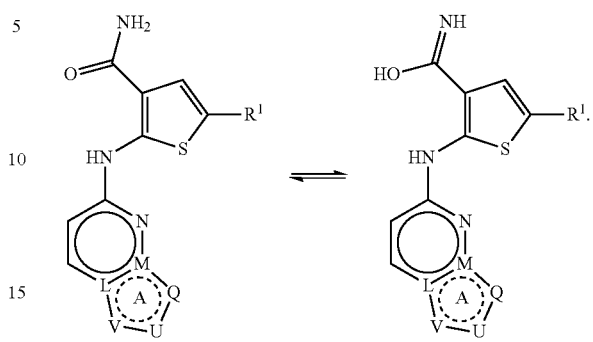

Many heteroaryl groups, such as imidazoles, exist as a mixture of 1H/2H tautomers. The tautomeric forms of these heteroaryl moieties are also within the scope of the instant invention.

When any variable (e.g. $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to four substituents, and the more preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "($C_1$-$C_{10}$)alkyl" is defined to include groups having 1, 2, 3, 4, 5, 6, 7, 8, 9 or 10 carbons in a linear or branched arrangement. For example, "($C_1$-$C_{10}$)alkyl" specifically includes methyl, ethyl, n-propyl, i-propyl, n-butyl, t-butyl, i-butyl, pentyl, hexyl, heptyl, octyl, nonyl, decyl, and so on.

The term "haloalkyl" means an alkyl radical as defined above, unless otherwise specified, that is substituted with one to five, preferably one to three halogen. Representative examples include, but are not limited to trifluoromethyl, dichloroethyl, and the like.

As used herein, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

"Alkoxy" represents either a cyclic or non-cyclic alkyl group of indicated number of carbon atoms attached through an oxygen bridge. "Alkoxy" therefore encompasses the definitions of alkyl and cycloalkyl above.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively. Such heteroaaryl moieties include but are not limited to: 2-benzimidazolyl, 2-quinolinyl, 3-quinolinyl, 4-quinolinyl, 1-isoquinolinyl, 3-isoquinolinyl, 4-isoquinolinyl, dihydroimidazopyrazinyl and dihydrooxozolopyridinyl.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: azabicyclohexyl, azaphosphinyl, azaspiroheptyl, benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, dioxidothiomorpholinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, oxadiazaspirodecyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro (Cl), fluoro (F), bromo (Br) and iodo (1).

Included in the instant invention is the free form of compounds of the instant invention, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of the instant invention. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Utility

The compounds of the present invention are inhibitors of JAK 1, JAK2, JAK 3, TYK2 and PDK1, and are therefore useful to treat or prevent myeloproliferative disorders or cancer in mammals, preferably humans.

An embodiment of the invention provides a method for inhibiting JAK1 tyrosine kinase, comprising administering to the mammal a therapeutically effective amount of any of the compounds or any of the pharmaceutical compositions described above.

An embodiment of the invention provides a method for inhibiting JAK2 tyrosine kinase, comprising administering to the mammal a therapeutically effective amount of any of the compounds or any of the pharmaceutical compositions described above.

An embodiment of the invention provides a method for inhibiting wild type or mutant JAK2 tyrosine kinase, comprising administering to the mammal a therapeutically effective amount of any of the compounds or any of the pharmaceutical compositions described above.

An embodiment of the invention provides a method for inhibiting JAK2V617F tyrosine kinase, comprising administering to the mammal a therapeutically effective amount of any of the compounds or any of the pharmaceutical compositions described above.

The compounds, compositions and methods provided herein are particularly deemed useful for the treatment of myeloproliferative disorder(s). Myeloproliferative disorders that may be treated include polycythemia vera (PV), essential thrombocythemia (ET), myeloid metaplasia with myelofibrosis (MMIVI), chronic myelogenous leukemia (CML), myelomonocytic leukemia (CMML), hypereosinophilic syndrome (HES), juvenile myelomonocytic leukemia (JMML), and systemic mast cell disease (SMCD).

It is known in the literature that inhibitors of JAK2 are useful in the treatment and/or prevention of myeloproliferative disorders. See, e.g., Tefferi, A. and Gilliland, D. G. *Mayo Clin. Proc.* 80(7): 947-958 (2005); Fernandez-Luna, J. L. et al. *Haematologica* 83(2): 97-98 (1998); Harrison, C. N. *Br. J. Haematol.* 130(2): 153-165 (2005); *Leukemia* (2005) 19, 1843-1844; and Tefferi, A. and Barbui, T. *Mayo Clin. Proc.* 80(9): 1220-1232 (2005).

The compounds, compositions and methods provided herein are also deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angio sarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma; and Adrenal glands: neuroblastoma. Thus, the term "cancerous cell" as provided herein, includes a cell afflicted by any one of the above-identified conditions.

The compounds, compositions and methods of the invention may also be useful in treating the following disease states: keloids and psoriasis.

Cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

Cancers that may be treated by the compounds, compositions and methods of the invention include: breast, prostate, colon, ovarian, colorectal and lung (non-small cell lung).

Cancers that may be treated by the compounds, compositions and methods of the invention include: breast, colon, colorectal and lung.

Cancers that may be treated by the compounds, compositions and methods of the invention include: lymphoma and leukemia.

The compounds of the instant invention are also inhibitors of the activity of PDK1 and are thus useful in the treatment of cancer, in particular cancers associated with deregulated activity of the PTEN/PI3K pathway including, but not limited to PTEN loss of function mutations and receptor tyrosine kinase gain of function mutations. Such cancers include, but are not limited to, ovarian, pancreatic, breast and prostate cancer, as well as cancers (including glioblastoma) where the tumor suppressor PTEN is mutated. See, Feldman, Richard L, et al., "Novel Small Molecule Inhibitors of 3-Phosphoinositide-dependent Kinase-1," *The Journal of Biological Chemistry*, Vol. 280, No. 20, Issue of May 20, pp. 19867-19874, 2005.

PDK1 signaling regulates multiple critical steps in angiogenesis. See, Mora, Alfonso et al., "PDK1, the master regulator of AGC kinase signal transduction," *Seminars in Cell & Developmental Biology* 15 (2004) 161-170. The utility of angiogenesis inhibitors in the treatment of cancer is known in the literature, see J. Rak et al. *Cancer Research*, 55:4575-4580, 1995 and Dredge et al., *Expert Opin. Biol. Ther*. (2002) 2(8):953-966, for example. The role of angiogenesis in cancer has been shown in numerous types of cancer and tissues: breast carcinoma (G. Gasparini and A. L. Harris, *J. Clin. Oncol.*, 1995, 13:765-782; M. Toi et al., *Japan. J. Cancer Res.*, 1994, 85:1045-1049); bladder carcinomas (A. J. Dickinson et al., *Br. J. Urol.*, 1994, 74:762-766); colon carcinomas (L. M. Ellis et al., *Surgery*, 1996, 120(5):871-878); and oral cavity tumors (J. K. Williams et al., *Am. J. Surg.*, 1994, 168:373-380). Other cancers include, advanced tumors, hairy cell leukemia, melanoma, advanced head and neck, metastatic renal cell, non-Hodgkin's lymphoma, metastatic breast, breast adenocarcinoma, advanced melanoma, pancreatic, gastric, glioblastoma, lung, ovarian, non-small cell lung, prostate, small cell lung, renal cell carcinoma, various solid tumors, multiple myeloma, metastatic prostate, malignant glioma, renal cancer, lymphoma, refractory metastatic disease, refractory multiple myeloma, cervical cancer, Karposi's sarcoma, recurrent anaplastic glioma, and metastatic colon cancer (Dredge et al., *Expert Opin. Biol. Ther*. (2002) 2(8): 953-966). Thus, the PDKI inhibitors disclosed in the instant application are also useful in the treatment of these angiogenesis related cancers.

Tumors which have undergone neovascularization show an increased potential for metastasis. In fact, angiogenesis is essential for tumor growth and metastasis. (S. P. Cunningham, et al., *Can. Research,* 61: 3206-3211 (2001)). The PDK1 inhibitors disclosed in the present application are therefore also useful to prevent or decrease tumor cell metastasis.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angio genesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge et al., *Expert Opin. Biol. Ther*. (2002) 2(8):953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

Further included within the scope of the invention is a method of treating hyperproliferative disorders such as restenosis, inflammation, autoimmune diseases and allergy/asthma.

Further included within the scope of the instant invention is the use of the instant compounds to coat stents and therefore the use of the instant compounds on coated stents for the treatment and/or prevention of restenosis (WO03/032809).

Further included within the scope of the instant invention is the use of the instant compounds for the treatment and/or prevention of osteoarthritis (WO03/035048).

Further included within the scope of the invention is a method of treating hypoinsulinism.

An embodiment of the invention provides a method for inhibiting JAK3 tyrosine kinase, comprising administering to the mammal a therapeutically effective amount of any of the compounds or any of the pharmaceutical compositions described above.

An embodiment of the invention provides a method for inhibiting TYK2 tyrosine kinase, comprising administering to the mammal a therapeutically effective amount of any of the compounds or any of the pharmaceutical compositions described above.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of bone loss, bone resorption, bone fractures, metastatic bone disease and/or disorders related to cathepsin functioning.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compounds of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

When a composition according to this invention is administered into a human subject, the daily dosage will normally be determined by the prescribing physician with the dosage generally varying according to the age, weight, and response of the individual patient, as well as the severity of the patient's symptoms.

In an embodiment, a suitable amount of an inhibitor of JAK2 is administered to a mammal undergoing treatment for cancer. Administration occurs in an amount of inhibitor of between about 0.1 mg/kg of body weight to about 60 mg/kg of body weight per day, or between 0.5 mg/kg of body weight to about 40 mg/kg of body weight per day. Another therapeutic dosage that comprises the instant composition includes from about 0.01 mg to about 1000 mg of inhibitor of JAK2. In another embodiment, the dosage comprises from about 1 mg to about 1000 mg of inhibitor of JAK2.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonallanti-hoimonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinyispermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxel, rhizoxin, dolastatin, mivobulin isethionate, auristatin, cemadotin, RPR109881, BMS184476, vinflunine, cryptophycin, 2,3,4,5, 6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB, 8aa,9b)-9-[2-[N-[2-(dimethylamino)ethyl]-N-methylamino] ethyl]-5-[4-hydro0xy-3,5-dimethoxyphenyl]-5,5a,6,8,8a,9-hexohydrofuro(3',':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-diclalorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (*PNAS*, Vol. 89, p. 7384 (1992); *JNCI*; Vol. 69, p. 475 (1982); *Arch. Opthahnol.*, Vol. 108, p. 573 (1990); *Anat. Rec.*, Vol. 238, p. 68 (1994); *FEBS Letters*, Vol. 372, p. 83 (1995); *Clin. Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin 11 antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature,* 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature,* 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of 1050 for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpimase, IM862, 5-methoxy-4-[2-methyl-3-(3-methyl-2-butenyi)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with inhibitors of Akt. Such inhibitors include compounds described in, but not limited to, the following publications: WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469.

A compound of the instant invention may also be useful for treating or preventing cancer in combination with PARP inhibitors.

A compound of the instant invention may also be useful for treating cancer in combination with the following therapeutic agents: abarelix (Plenaxis depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuxirnab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Domee); dactinomycin, actinomycin D (Cosmegene); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); B Solution (Elliott's B Solution®); epirubicin (Ellence®); Epoetin alfa (epogen®); erlotinib (Tarceva®); estramustine (Emcyt®); etoposide phosphate (Etopophos®); etoposide, VP-16 (Vepeside); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin implant®); hydroxyurea (Hydrea®); Ibritumomab Tiuxetan (Zevalin); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex tabs®); methotrexate (Methotrexatee); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimtag); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosole); tamoxifen (Nolvadex®); temozolomide (Temodar®); teniposide, VM-26 (Vumone); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstare); vinblastine (Velban®); vincristine (Oncovin®); vinorelbine (Navelbine®); and zoledronate (Zometa®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

All patents, publications and pending patent applications identified are hereby incorporated by reference.

The abbreviations used herein have the following tabulated meanings. Abbreviations not tabulated below have their meanings as commonly used unless specifically stated otherwise.

| | |
|---|---|
| Ac = | Acetyl |
| Bn = | Benzyl |
| DIBAL = | diisobutylaluminum hydride |
| DMAP = | 4-(dimethylamino)pyridine |
| DMF = | N,N-dimethylformamide |
| $Et_3N$ = | Triethylamine |
| HMDS | Hexamethyldisilazide |
| LDA = | lithium diisopropylamide |
| mCPBA = | metachloroperbenzoic acid |
| Ms = | methanesulfonyl = mesyl = $SO_2Me$ |
| NSAID = | non-steroidal anti-inflammatory drug |
| o-Tol = | ortho-tolyl |
| Ph = | Phenyl |
| PMB = | para-methoxybenzyl |
| r.t. = | room temperature |
| Rac. = | Racemic |
| SEM = | 2-(trimethylsilyl)ethoxymethoxy |
| TBAF = | tetra-n-butylammonium fluoride |
| TEA = | triethylamine |
| TFA = | trifluoroacetic acid |
| TFAA = | trifluoroacetic acid anhydride |
| THF = | Tetrahydrofuran |
| TLC = | thin layer chromatography |
| TMS-CN = | trimethylsilyl cyanide |
| TMSI | trimethylsilyl iodide |
| $C_3H_5$ = | Allyl |

ALKYL GROUP ABBREVIATIONS

| | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | Cyclobutyl |
| c-Pen = | cyclopentyl |
| c-Hex = | cyclohexyl |

The compounds of the present invention can be prepared according to the following general schemes, using appropriate materials, and are further exemplified by the subsequent specific examples. The compounds illustrated in the examples are not, however, to be construed as forming the only genus that is considered as the invention. The illustrative Examples below, therefore, are not limited by the compounds listed or by any particular substituents employed for illustrative purposes. Those skilled in the art will readily understand that known variations of the conditions and processes of the following preparative procedures can be used to prepare these compounds. All temperatures are degrees Celsius unless otherwise noted.

METHODS OF SYNTHESIS

Method 1

General procedures to prepare compounds of the instant invention are described in Scheme 1. Aldehyde I can be homologated by one carbon using the appropriate Wittig agent and base, and the corresponding methyl enol ether II can be hydrolyzed under acidic conditions to give the acetaldehyde III. The aldehyde can be condensed with 2-cyanoacetamide and sulfur to afford thiophene IV. The 2-amino thiophene IV was elaborated to the final product thiophene V through a palladium catalyzed coupling with an appropriate optionally substituted halogenated bicyclic heterocycle.

SCHEME 1

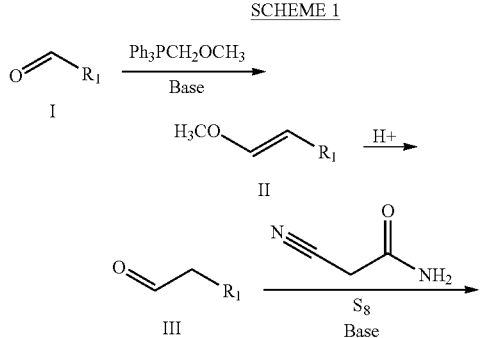

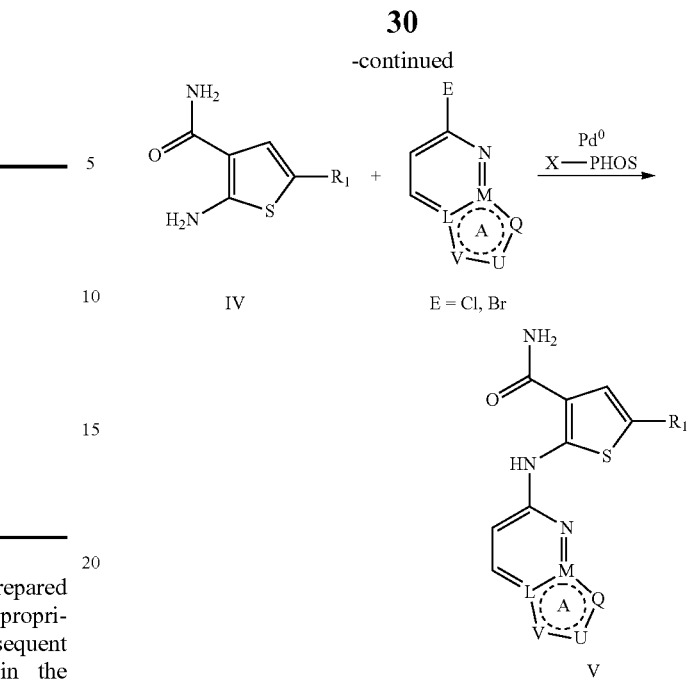

Method 2

General procedures to prepare compounds of the instant invention are also described in Scheme 2. An appropriate aryl or heteroaryl iodide VI can be coupled to allyl bromide by first performing an iodo-magensium exchange and then introducing allyl bromide in the presence of a copper cyanide-lithium chloride complex. The resulting allylated aryl ring VII can be dihydroxylated using a catalytic amount of osmium tetroxide in the presence of a stoichiometric reoxidant, giving the diol VIII that can be cleaved to give the aryl acetylaldehyde III. The aldehyde can be condensed with 2-cyanoacetamide and sulfur to afford thiophene IV. The 2-amino thiophene IV was elaborated to the final product thiophene V through a palladium catalyzed coupling with an appropriate optionally substituted halogenated bicyclic heterocycle.

SCHEME 2

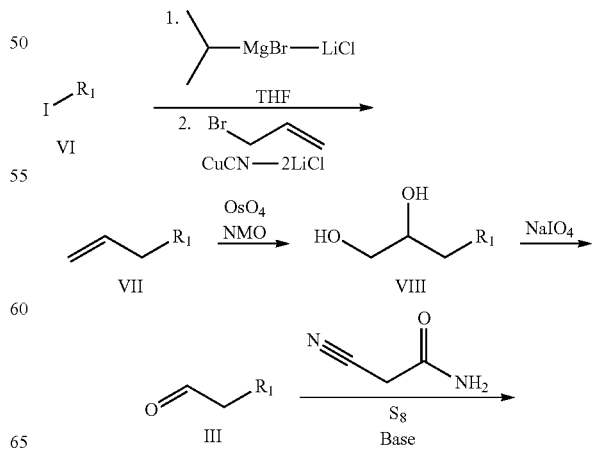

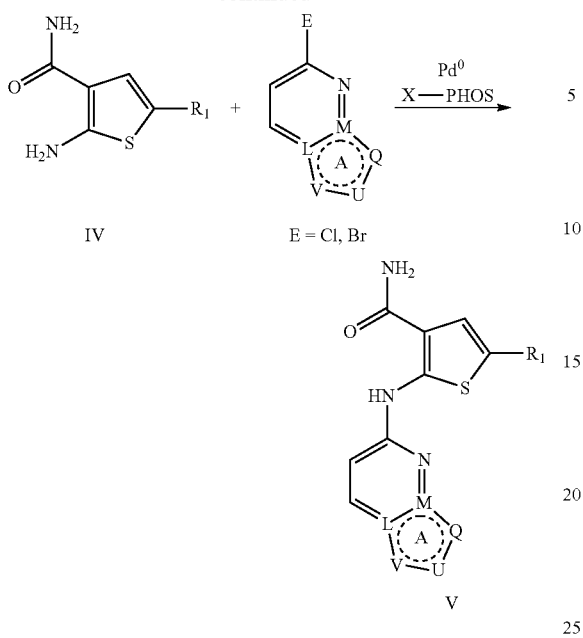

Method 3

General procedures to prepare compounds of the instant invention are described in Scheme 3. Nitrothiophene IX can be alkylated with chloroform using a variety of strongly basic conditions to afford the dichloromethyl adduct X. Hydrolysis to the aldehyde XI under acidic or basic conditions followed by condensation with hydroxylamine affords oxime XII. Transition metal-catalyzed rearrangement to the amide XIII followed by palladium catalyzed cross coupling with aryl or heteroaryl boronates affords the functionalized nitro thiophene intermediate XIV. Reduction of the nitro group and coupling with an appropriate optionally substituted halogenated bicyclic heterocycle using palladium catalysis affords the 2-aminopyridyl thiophene V.

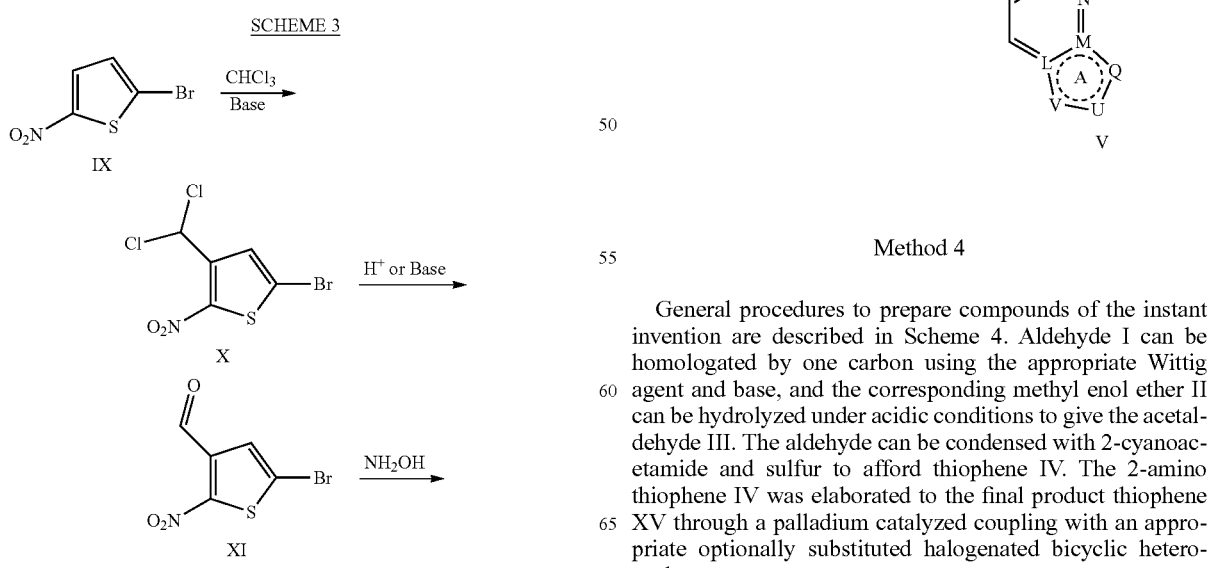

Method 4

General procedures to prepare compounds of the instant invention are described in Scheme 4. Aldehyde I can be homologated by one carbon using the appropriate Wittig agent and base, and the corresponding methyl enol ether II can be hydrolyzed under acidic conditions to give the acetaldehyde III. The aldehyde can be condensed with 2-cyanoacetamide and sulfur to afford thiophene IV. The 2-amino thiophene IV was elaborated to the final product thiophene XV through a palladium catalyzed coupling with an appropriate optionally substituted halogenated bicyclic heterocycle.

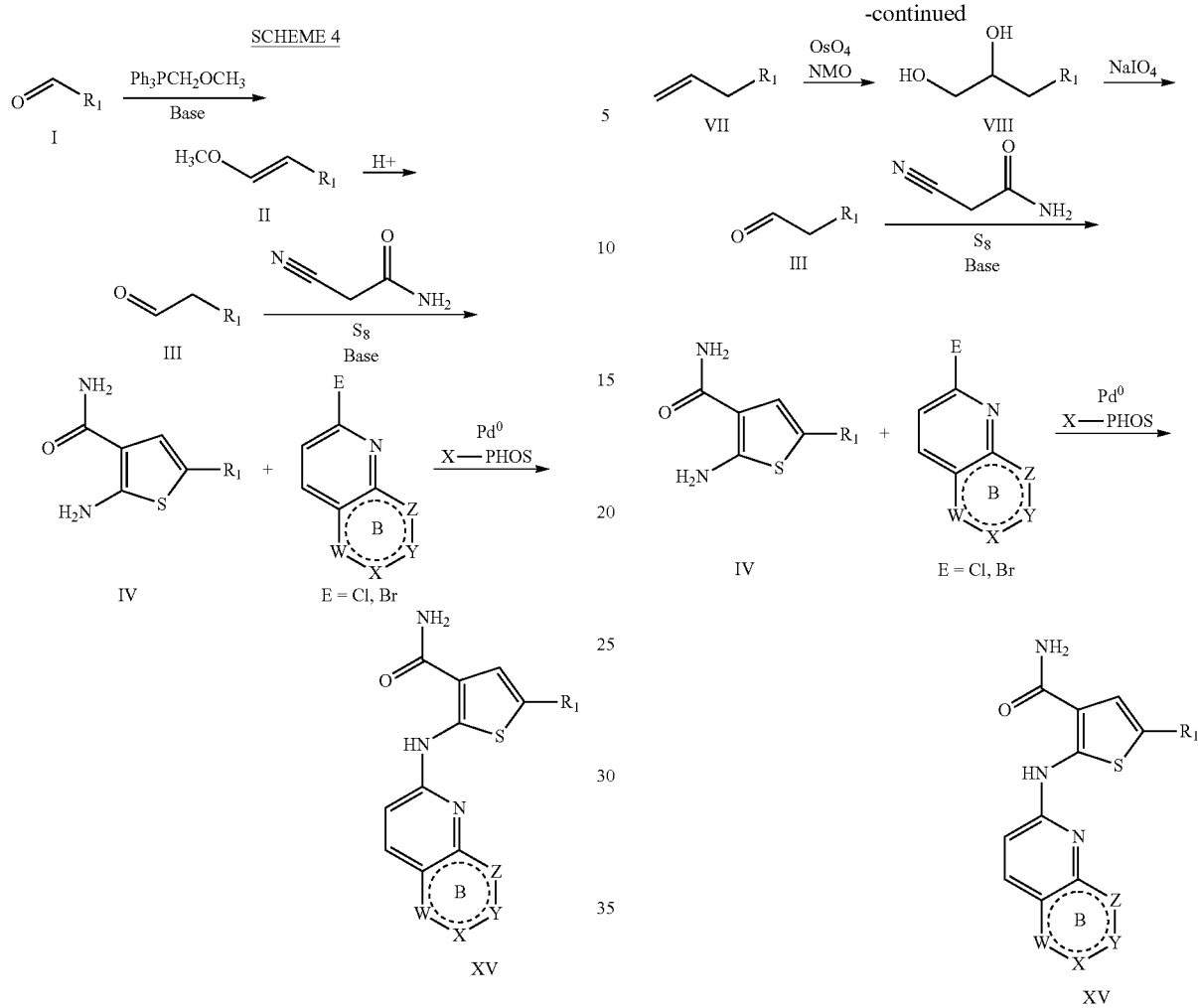

Method 5

General procedures to prepare compounds of the instant invention are also described in Scheme 5. An appropriate aryl or heteroaryl iodide VI can be coupled to allyl bromide by first performing an iodo-magensium exchange and then introducing allyl bromide in the presence of a copper cyanide-lithium chloride complex. The resulting allylated aryl ring VII can be dihydroxylated using a catalytic amount of osmium tetroxide in the presence of a stoichiometric reoxidant, giving the diol VIII that can be cleaved to give the aryl acetylaldehyde III. The aldehyde can be condensed with 2-cyanoacetamide and sulfur to afford thiophene IV. The 2-amino thiophene IV was elaborated to the final product thiophene XV through a palladium catalyzed coupling with an appropriate optionally substituted halogenated bicyclic heterocycle.

The invention will now be illustrated in the following non-limiting examples in which, unless otherwise stated:

1. All final products were analyzed by NMR, LCMS.
2. Intermediates were analyzed by NMR and/or TLC and/or LCMS.
3. Most compounds were purified by flash chromatography on silica gel, reverse phase HPLC, recrystallization, and/or swish (suspension in a solvent followed by filtration of the solid).
4. The course of the reactions was followed by thin layer chromatography (TLC) and/or LCMS and reaction times are given for illustration only.

Intermediate 1

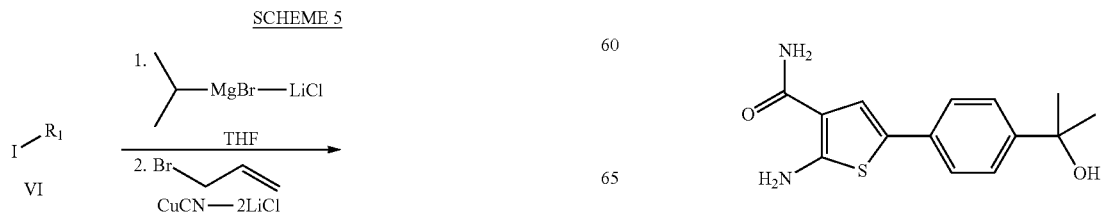

2-Amino-5-[4-(1-hydroxy-1-methylethyl)phenyl] thiophene-3-carboxamide

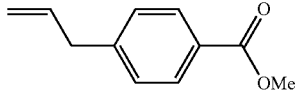

Step 1: Methyl 4-allylbenzoate

A 100 mL flask containing copper(I) cyanide (0.85 g, 9.54 mmol) and lithium chloride (0.81 g, 19.08 mmol) was placed under vacuum and heated to 150° C. for 90 minutes, and then cooled to room temperature. A 500 mL flask containing a solution of methyl 4-iodobenzoate (12.5 g, 47.7 mmol) in tetrahydrofuran (75 mL) under argon was cooled to −25° C. and isopropylmagnesium chloride—lithium chloride complex (49.1 mL, 1 M, 49.1 mmol) was added over 16 minutes while the internal temperature was maintained at below −20° C. After 45 minutes, the copper(I) cyanide and lithium chloride were dissolved in tetrahydrofuran (20 mL) with sonication, and the resulting solution was transferred to the clear, orange reaction mixture via cannula. After an additional 25 minutes, allyl bromide (4.13 mL, 47.7 mmol) was added over 10 min while the reaction temperature was kept below −15° C., and then the reaction was kept at −5° C. for 24 hours. 60 mL of 9:1 NH$_4$Cl(sat):NH$_3$(sat) was then added, followed by 50 mL of water and 200 mL dichloromethane. The layers were separated, and the aqueous layer was extracted with dichloromethane (2×100 mL). The combined organic layers were washed with 100 mL water and then diluted with 100 mL dichloromethane and 100 mL chloroform. The organic layer was washed with 150 mL brine, dried over MgSO$_4$ and Na$_2$SO$_4$, filtered, and concentrated to yield an oil and a solid. The oil was filtered through a cotton plug and the entire flask was then rinsed with hexanes (4×2 mL); these rinses were combined with the oil after filtering through cotton. Concentration of this solution yielded the title compound. $^1$H NMR (600 MHz, DMSO): δ 7.86 (d, J=8.2Hz, 2H), 7.31 (d, J=8.5Hz, 2H), 5.93 (m, 1 H), 5.07 (m, 1H), 5.05 (m, 1H), 3.79 (s, 3H), 3.41 (d, J=6.7Hz, 1H).

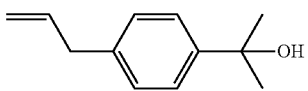

Step 2: 2-(4-Allylphenyl)propan-2-ol

A solution of methyl 4-allylbenzoate (5.66 g, 32.1 mmol) in tetrahydrofuran (37 mL) at 0° C. under an argon atmosphere was charged with a solution of methyl magnesium bromide in diethyl ether (3 M, 26.8 mL, 80 mmol). The reaction mixture was allowed to warm to room temperature and then it was cooled to 0° C. after an additional four hours, at which time a saturated aqueous ammonium chloride solution (50 mL) was added slowly followed by diethyl ether (100 mL). The layers were separated, and the aqueous layer was extracted with diethyl ether (2×50 mL). The combined organic layers were dried over magnesium sulfate, filtered, and concentrated to afford the title compound.

$^1$H NMR (600 MHz, DMSO): δ 7.34 (d, J=8.5Hz, 2H), 7.06 (d, J=8.5Hz, 2H), 5.90 (m, 1 H), 5.02 (m, 1H), 4.99 (m, 1H), 4.88 (s, 1H), 3.27 (m, 2H), 1.35 (s, 6H).

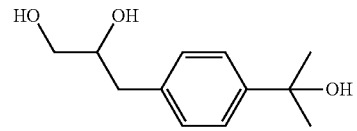

Step 3: 3-[4-(1-Hydroxy-1-methylethyl)phenyl]propane-1,2-diol

To a biphasic mixture of 2-(4-allylphenyl)propan-2-ol (5.53 g, 31.4 mmol) and N-Methyl morpholine NV oxide (3.86 g, 32.9 mmol) in acetone (11 mL) and water (22 mL) was added osmium tetroxide (3.14 mL, 0.157 mmol) with vigorous stirring. After 24 hours, dithionite (0.15 g), Florisil (1.5 g), and water (8 mL) were added and allowed to stir for an additional 15 minutes before filtering through a pad of Celite. The filter was rinsed with acetone (2×5 mL, then 2×10 mL), and filtrate was concentrated by rotary evaporation to remove the acetone. The remaining liquid was diluted with 9:1 chloroformisopropanol (20 mL) and aqueous hydrogen chloride (1 M, 20 mL), the layers were separated, and the acidic (pH=1) aqueous layer was extracted with 9:1 chloroformisopropanol (2×20 mL). The combined organic layers were washed with 3:1 water:brine (12 mL), saturated aqueous sodium bicarbonate (10 mL), and brine (10 mL). The aqueous layers were combined and saturated with solid sodium chloride (50 cc) by stirring for 90 minutes, and then extracted with 9:1 chloroformisopropanol (3×50 mL). The combined organic extracts were dried over sodium sulfate, filtered, and concentrated, and the crude material was purified by silica gel chromatography (5-20% methanol/dichloromethane) to afford 3-[4-(1-hydroxy-1-methylethy)phenyl]propane-1,2-diol as an oil.

$^1$H NMR (600 MHz, DMSO): δ 7.29 (d, J=8.5Hz, 2H), 7.08 (d, J=8.5Hz, 2H), 4.86 (s, 1H), 4.50 (t, J=5.7Hz, 1H), 4.47 (d, J=5.3Hz, 1H), 3.55 (m, 1H), 3.23 (m, 2H), 2.67 (dd, J=13.8, 8.8Hz, 1H), 2.43 (dd, J=13.6, 7.6Hz, 1H), 1.35 (s, 6H).

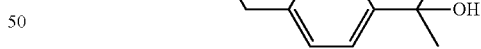

Step 4: [4-(1-Hydroxy-1-methylethyl)phenyl]acetaldehyde

A biphasic mixture of 3-[4-(1-hydroxy-1-methylethyl) phenyl]propane-1,2-dial (5.44 g, 25.9 mmol) in water (85 mL) and diethyl ether (170 mL) was charged with sodium periodate (11.07 g, 51.7 mmol) and stirred vigorously for two hours. The reaction mixture was then partitioned between diethyl ether (50 mL) and saturated aqueous sodium thiosulfate (50 mL), and the layers were separated. The aqueous layer was extracted with diethyl ether (2×100 mL), and the combined organic layers were washed with brine (25 mL), dried over sodium sulfate, filtered, and concentrated. To remove water left over, the concentrated material was dissolved in dichloromethane (70 mL), washed with brine (20 mL), dried over sodium sulfate, filtered, and concentrated to yield the title compound.

$^1$H NMR (600 MHz, DMSO): δ 9.63 (t, J=2.0Hz, 1H), 7.40 (d, J=8.5Hz, 2H), 7.12 (d, 8.5Hz, 2H), 4.95 (s, 1H), 3.68 (d, J=2.0Hz, 2H), 1.35 (s, 6H).

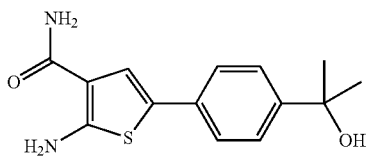 [SMILES: CC(C)(O)c1ccc(-c2cc(C(N)=O)c(N)s2)cc1]

Step 5: 2-Amino-5-[4-(1-hydroxy-1-methylethyl)phenyl]thiophene-3-carboxamide

The title compound was prepared using [4-(1-hydroxy-1-methylethyl)phenyl]acetaldehyde (3.65 g, 20.5 mmol) as the starting material according to the general thiophene synthesis procedure in Intermediate 3 Step 3.

LRMS (APCI) calc'd for ($C_{14}H_{17}N_2O_2S$) [M+H]$^+$: 277. Found: 277.

Intermediate 2

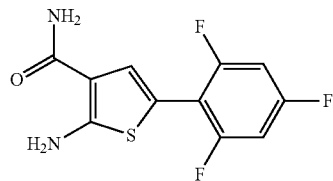 [SMILES: NC(=O)c1cc(-c2c(F)cc(F)cc2F)sc1N]

2-Amino-5-(2,4,6-trifluorophenyl)thiophene-3-carboxamide

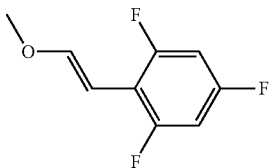

Step 1: 1,3,5-Trifluoro-2-[(E,Z)-2-methoxyvinyl]benzene

A suspension of (methoxymethyl)triphenylphosphonium chloride (25.7 g, 75.0 mmol) in tetrahydrofuran (110 mL) under argon was charged with potassium tert-butoxide (8.06 g, 71.8 mmol) to give a red suspension. After 30 minutes a solution of 2,4,6-trifluorobenzaldehyde (5 g, 31.2 mmol) in tetrahydrofuran (40 mL) was added via cannula. After stirring for 75 minutes, the suspension was filtered, the collected solids were washed with ethyl acetate (15 mL), and the filtrate was concentrated. Addition of hexanes (60 mL) and sonication, a precipitate formed that was removed by filtration; the solids were washed with additional hexanes (50 mL). The filtrate was diluted with ethyl acetate (30 mL) and the combined organic layers were washed with aqueous saturated ammonium chloride solution (2×30 mL) and brine (30 mL), dried over sodium sulfate, filtered, and concentrated. The crude product was purified by silica gel chromatography (5% ethyl acetate/hexanes) to afford the title compound.

$^1$H NMR (600 MHz, DMSO) (*denotes minor isomer): δ 7.22 (d, J=13.2Hz, 1H), 7.14 (m, 2 H), 7.08 (m, 2H)*, 6.44 (d, J=6.8Hz, 1H)*, 5.57 (d, J=13.2Hz, 1H), 5.02 (d, J=6.2Hz, 1H)*, 3.64 (s, 3H), 3.62 (s, 3H)*.

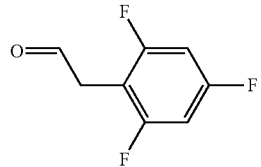 [SMILES: O=CCc1c(F)cc(F)cc1F]

Step 2: (2,4,6-Trifluorophenyl)acetaldehyde

A solution of 1,3,5-trifluoro-2-[(E,Z)-2-methoxyvinyl]benzene (5.87 g, 31.2 mmol) and hydrogen chloride in dioxane (4 M, 40 mL, 160 mmol) was stirred for 30 minutes, and then diluted with diethyl ether (60 mL) and water (20 mL). The two layers were separated and the organic layer was washed with saturated aqueous sodium bicarbonate (20 mL) (CAUTION: gas evolution), aqueous phosphate buffer (1 M, pH=8, 20 mL), and brine (20 mL), dried over sodium sulfate, filtered, and concentrated to give the title compound.

$^1$H NMR (600 MHz, DMSO): δ 9.63 (s, 1H), 7.18 (m, 2H), 3.84 (s, 2H).

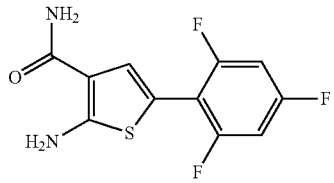 [SMILES: NC(=O)c1cc(-c2c(F)cc(F)cc2F)sc1N]

Step 3: 2-Amino-5-(2,4,6-trifluorophenyl)thiophene-3-carboxamide

A suspension of (2,4,6-trifluorophenyl)acetaldehyde (3.64 g, 20.91 mmol), 2-cyanoacetamide (1.93 g, 23.0 mmol), sulfur (0.74 g, 23.0 mmol), and morpholine (2.0 mL, 23.0 mmol) in ethanol (40 mL) in a 100 mL flask with an attached condenser was placed under an argon atmosphere with 3 vacuum/argon flush cycles and then heated to 70° C. After 14 hours, the reaction mixture was cooled to room temperature, filtered, and concentrated. The crude oil was diluted with ethyl acetate (100 mL) and aqueous citric acid (1 M, 25 mL). The layers were separated and the organic layer was washed with water (25 mL), saturated aqueous sodium bicarbonate solution (25 mL), and brine (25 mL), dried over sodium sulfate, filtered, and concentrated. The crude oil was triturated with dichloromethane and the resulting solid was collected by filtration. This solid was purified by silica gel chromatography (25-100% ethyl acetate/hexanes) to give the title compound.

LRMS (APCI) calc'd for ($C_{11}H_8F_3N_2OS$) $[M+H]^+$: 273. Found: 273.

Intermediate 3

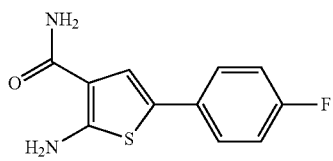 [SMILES: NC(=O)c1cc(-c2ccc(F)cc2)sc1N]

2-Amino-5-(4-fluorophenyl)thiophene-3-carboxamide

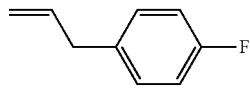

Step 1: 1-Allyl-4-fluorobenzene

Allyl bromide (4.33 mL, 50 mmol) was added dropwise to a solution of 4-fluorophenyl magnesium bromide (50 mmol) in tetrahydrofuran (25 mL) and diethyl ether (25 mL). After 16 hours, the reaction suspension was diluted with diethyl ether (100 mL) and saturated aqueous ammonium chloride (50 mL). The layers were separated, and the organic layer was washed with water (25 mL) and brine (25 mL), dried over magnesium sulfate, filtered, and concentrated to afford 1-allyl-4-fluorobenzene.

$^1$H NMR (600 MHz, DMSO): 7.18 (m, 2H), 7.08 (d, 2H), 5.90 (m, 1H), 5.03 (m, 1H), 5.00 (m, 1H), 3.32 (d, J=6.7Hz, 2H).

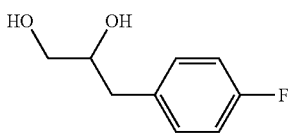 [SMILES: OCC(O)Cc1ccc(F)cc1]

Step 2: 3-(4-Fluorophenyl)propane-1,2-diol

The title compound was prepared according to the procedure in Intermediate 1 Step 3 using 1-allyl-4-fluorobenzene (3.76 g, 27.6 mmol) as the starting material.

$^1$H NMR (600 MHz, DMSO): δ 7.18 (m, 2H), 7.02 (m, 2H), 4.52 (m, 2H), 3.55 (m, 1H), 3.25 (m, 1H), 3.21 (m, 1H), 2.72 (dd, J=13.7, 4.6Hz, 1H), 2.46 (m, 1H).

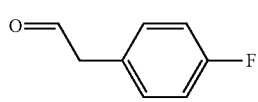

Step 3: (4-Fluorophenyl)acetaldehyde

The title compound was prepared according to the procedure in Intermediate 1

Step 4 using 3-(4-fluorophenyl)propane-1,2-diol (3.69 g, 21.7 mmol) as the starting material.

$^1$H NMR (600 MHz, DMSO): δ 9.63 (t, J=1.8Hz, 1H), 7.24 (m, 2H), 7.14 (m, 2H), 3.78 (d, J=1.5Hz, 2H).

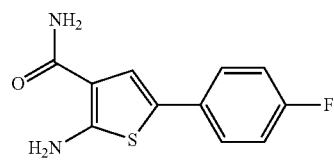 [SMILES: NC(=O)c1cc(-c2ccc(F)cc2)sc1N]

Step 4:
2-Amino-5-(4-fluorophenyl)thiophene-3-carboxamide

2-Amino-5-(4-fluorophenyl)thiophene-3-carboxamide was prepared according to the general thiophene synthesis procedure in Intermediate 2 Step 3 using (4-fluorophenyl)acetaldehyde (2.93 g, 21.2 mmol) as the starting material.

LRMS (APCI) calcd for ($C_{11}H_{10}FN_2OS$) $[M+H]^+$: 237. Found: 237.

Intermediate 4

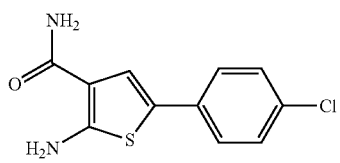 [SMILES: NC(=O)c1cc(-c2ccc(Cl)cc2)sc1N]

2-Amino-5-(4-chlorophenyl)thiophene-3-carboxamide

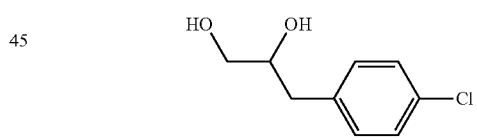

Step 1: 3-(4-Chlorophenyl)propane-1,2-diol 3-(4-Chlorophenyl)propane-1,2-diol was prepared according to the procedure in Intermediate 1 Step 3 using 1-allyl-4-chlorobenzene (6.19 g, 40.6 mmol) as the starting material.

$^1$H NMR (600 MHz, DMSO): δ 7.24 (d, 2H), 7.18 (d, 2H), 4.56 (m, 2H), 3.55 (m, 1H), 3.26 (m, 1H), 3.21 (m, 1H), 2.72 (dd, 1H), 2.46 (m, 1H).

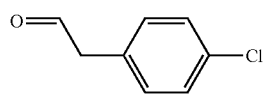

Step 2: (4-Chlorophenyl)acetaldehyde (4-Chlorophenyl)acetaldehyde was prepared according to the procedure in Intermediate 1 Step 4 using 3-(4-chlorophenyl)propane-1,2-diol (5.42 g, 29.0 mmol) as the starting material.

$^1$H NMR (600 MHz, DMSO): δ 9.63 (t, 1H), 7.36 (d, 2H), 7.22 (d, 2H), 3.77 (d, 2H).

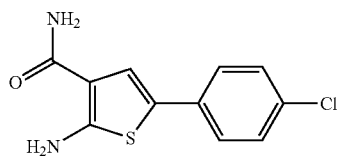 [SMILES: NC(=O)c1cc(-c2ccc(Cl)cc2)sc1N]

Step 3: 2-Amino-5-(4-chlorophenyl)thiophene-3-carboxamide

2-Amino-5-(4-chlororophenyl)thiophene-3-carboxamide was prepared according to the general thiophene synthesis procedure in Intermediate 2 Step 3 using (4-chlorophenyl)acetaldehyde (4.04 g, 26.1 mmol) as the starting material.

LRMS (APCI) calc'd for ($C_{11}H_{10}ClN_2OS$) [M+H]$^+$: 253. Found: 253.

Intermediate 5

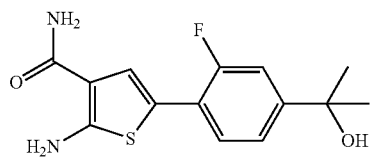 [SMILES: CC(C)(O)c1ccc(-c2cc(C(N)=O)c(N)s2)c(F)c1]

2-Amino-5-[2-fluoro-4-(1-hydroxy-1-methylethyl)phenyl]thiophene-3-carboxamide

Step 1. 2-(4-Bromo-2-fluorophenyl)vinyl methyl ether

Methoxymethyl)triphenylphosphonium chloride (147 g, 0.48 mol) was suspended in tetrahydrofuran (1.5 L) under argon atmosphere, stirred with ice-water cooling. t-BuOK (51.6 g, 0.46 mol) was added in portions. A solution of 4-bromo-2-fluorobenzaldehyde (40.6 g, 0.2 mol) in tetrahydrofuran (500 mL) was then added to the reaction mixture. The solution was stirred at room temperature for 1 hour. The solution was poured into ice-water and extracted with ethyl acetate (2×). The combined organic phases were dried and concentrated in vacuo. Purification via flash chromatography afforded the title compound.

$^1$H NMR (300 MHz, CDCl$_3$): δ 7.2-7.3 (m, 3H), 6.2 (d, 1H), 5.8 (d, 1H), 3.7 (s, 3H).

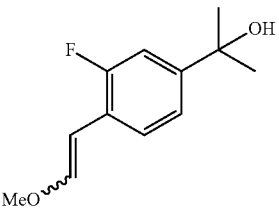

Step 2. 2-{3-Fluoro-4-[2-methoxyvinyl]phenyl}propan-2-ol

To a solution of compound 2-(4-bromo-2-fluorophenyl) vinyl methyl ether (115.5 g, 0.5 mol) in tetrahydrofuran (666 mL) at −78° C. was added n-butyllithium (240 mL of 2.5M in hexanes, 0.6 mol), and the resulting mixture was stirred at −78° C. for 1 hour. A solution of acetone (37.7 g, 0.65 mol) in tetrahydrofuran (280 mL) was added dropwise to the reaction mixture. Then the reaction solution was slowly warmed to 0° C., stirred for 30 minutes, and then at room temperature for 30 minutes. Water (300 mL) was added to quench the reaction. The biphasic mixture was extracted with ethyl acetate (2×). The combined organics were dried and concentrated in vacuo. Purification via flash chromatography afforded the title compound.

$^1$H NMR (300 MHz, CDCl$_3$): δ 6.9-7.3 (m, 3H), 6.2 (d, 1H), 5.8 (d, 1H), 3.73 (s, 3H), 1.55 (s, 6H).

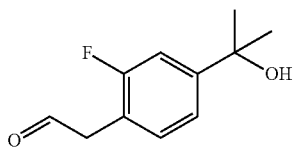

Step 3. [2-Fluoro-4-(1-hydroxy-1-methylethyl)phenyl]acetaldehyde

To a room temperature solution of 2-{3-fluoro-4-[2-methoxyvinyl]phenyl}propan-2-ol (100 mg, 0.48 mmol) in acetone (5 mL) was added dropwise 4 M aqueous hydrochloric acid (5 mL, 20 mmol). The reaction was stirred at room temperature for two hours. The mixture was then diluted with 25 mL of water and 50 mL of diethyl ether. The water phase was extracted with diethyl ether (2×) and the combined organic layers were washed with saturated aqueous sodium bicarbonate and brine, dried and concentrated in vacuo to afford the title compound.

$^1$H NMR (400 MHz, CDCl$_3$): δ 9.76 (s, 1H), 7.14-7.28 (m, 3H), 3.73 (s, 2H), 1.57 (s, 6H).

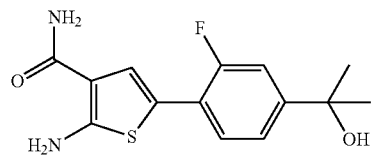 [SMILES: CC(C)(O)c1ccc(-c2cc(C(N)=O)c(N)s2)c(F)c1]

Step 4. 2-Amino-5-[2-fluoro-4-(1-hydroxy-1-methylethyl)phenyl]thiophene-3-carboxamide A solution of [2-fluoro-4-(1-hydroxy-1-methylethyl)phenyl]acetaldehyde (74.5 g, 0.38 mol) in dry dimethylformamide (240 mL) was treated with 2-cyanoacetamide (44.5 g, 0.53 mmol) and sulfur (17 g, 0.53 mmol). Triethylamine (53.6 g, 0.53 mmol) was added dropwise to the reaction mixture using an ice-bath to control the resulting exotherm. The reaction was stirred at room temperature overnight, and then poured into a mixture of ice-water (800 mL) and ethyl acetate (80 mL). An emulsion formed and the insoluble material was filtered. The filtrate was extracted with ethyl acetate (2×). The organic layers were concentrated in vacuo and the resulting residue was combined with the filter cake from the previous filtration. This combined material was washed with ethyl acetate. Purification via flash chromatography afforded the title compound.

$^1$H NMR (400 MHz, DMSO): δ 7.55 (s, 4H), 7.46 (s, 4H), 7.41 (t, 1H), 6.23-6.26 (br, 2H), 5.11 (s, 1H), 1.39 (s, 6H). LRMS (APCI) calc'd for ($C_{14}H_{16}FN_2O_2S$) [M+H]$^+$: 295. found 295.

Intermediate 6

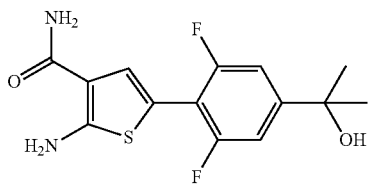 [SMILES: CC(C)(O)c1cc(F)c(-c2cc(C(N)=O)c(N)s2)c(F)c1]

2-Amino-5-[2,6-difluoro-4-(1-hydroxy-1-methylethyl)phenyl]thiophene-3-carboxamide

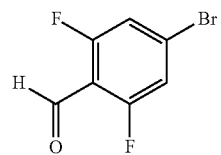

Step 1. 4-Bromo-2,6-difluorobenzaldehyde

To a solution of diisopropylamine (93 mL, 0.66 mol) in dry tetrahydrofuran (300 mL) at −50° C. was added n-BuLi (212 mL of 2.M in hexanes, 0.53 mol.) dropwise. The solution was stirred at room temperature for 30 mins. This solution was then added dropwise to a cooled (−75° C.) solution of 1-bromo-3,5-difluorobenzene (84 g, 0.44 mol) in dry tetrahydrofuran (900 mL). The mixture was stirred at −78° C. for one hour. Dry dimethylformamide (63.6 mL, 0.82 mol) was added and the mixture was stirred for two hours. The cooling bath was removed and the mixture was slowly warmed to room temperature. The mixture was diluted with diethyl ether and poured into cooled 1 M aqueous hydrochloric acid (1 L). The aqueous phase was extracted with diethyl ether. The combined phases were dried, filtered, and the solvent was removed in vacuo to give the crude product. The crude was re-crystallized with ethyl acetate and petroleum ether to afford the title compound.

$^1$H NMR (300 MHz, CDCl$_3$): δ 10.16 (s, 1H), 7.66 (d, 2H).

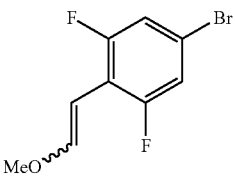 [SMILES: COC=Cc1c(F)cc(Br)cc1F]

Step 2. 2-(4-Bromo-2,6-difluorophenyl)vinyl methyl ether (Methoxymethyl)triphenylphosphonium chloride (1133 g, 3.7 mol) was suspended in tetrahydrofuran (7.0 L) under argon atmosphere, and stirred with ice-water cooling. t-BuOK (397 g, 3.54 mol) was added in portions. Then a solution of 4-bromo-2,6-difluorobenzaldehyde (340 g, 1.54 mol) in tetrahydrofuran (2.7 L) was added and the reaction was stirred at room temperature for 6 hours. The solution was then poured into ice-water and extracted with ethyl acetate (2×). The combined organic phases were dried and concentrated in vacuo. This material was purified by flash chromatography to afford the title compound.

$^1$H NMR (400 MHz, CDCl$_3$): δ 7.02 (d, 2H), 6.30 (d, 0.3H), 5.70 (d, 0.6H), 5.10 (d, 0.3H), 3.75 (s, 3H).

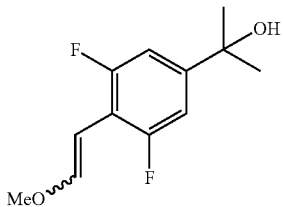

Step 3. 2-{3,5-Difluoro-4-[2-methoxyvinyl]phenyl}propan-2-ol

To a cooled (−78° C.) solution of 2-(4-bromo-2,6-difluorophenyl)vinyl methyl ether (45 g, 0.18 mol) in methyl tert-butyl ether (300 mL) was added n-BuLi (75 mL of 2.5M in hexanes, 0.19 mol), and the mixture was stirred at −78° C. for one hour. A solution of acetone (13.6 g, 0.24 mol) in methyl tert-butyl ether (100 mL) was added dropwise to the reaction mixture and the resulting solution was stirred at −78° C. for two hours. Water (90 ml) was added to quench the reaction. The resulting biphasic mixture was extracted with ethyl acetate (2×). The organic layers were dried and concentrated in vacuo. Purification via flash chromatography afforded the title compound.

$^1$H NMR (400 MHz, CDCl$_3$): δ 7.35 (d, 1H), 6.96 (d, 2H), 532 (d, 1H), 3.72 (s, 3H), 1.50 (s, 6H).

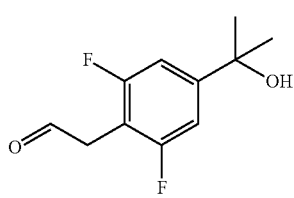

Step 4. [2,6-Difluoro-4-(1-hydroxy-1-methylethyl) phenyl]acetaldehyde

A solution of 2-{3,5-difluoro-4-[2-methoxyvinyl] phenyl}propan-2-ol (5.0 g, 22 mmol) in acetone (25 mL) was added dropwise to 4 M aqueous hydrochloric acid (25 mL, 100 mmol) with ice-water cooling, keeping the temperature below 10° C. Then the mixture was stirred at room temperature for six hours. The resulting mixture was extracted with ethyl acetate (2×) and the combined organic phases were washed with saturated aqueous sodium bicarbonate and brine. The organic layer was then dried and concentrated in vacuo to afford the title compound.

$^1$H NMR (400 MHz, CDCl$_3$): δ 9.70 (s, 1H), 7.00 (d, 2H), 3.72 (s, 2H), 1.50 (s, 6H).

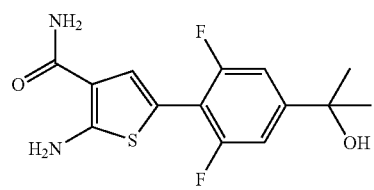 [SMILES: CC(C)(O)c1cc(F)c(-c2cc(C(N)=O)c(N)s2)c(F)c1]

Step 5. 2-Amino-5-[2,6-difluoro-4-(1-hydroxy-1-methylethyl)phenyl]thiophene-3-carboxamide A solution of [2,6-difluoro-4-(1-hydroxy-1-methylethyl)phenyl]acetaldehyde (84.5 g, 0.395 mol) in dry dimethylformamide (250 mL) was treated with 2-cyanoacetamide (36.5 g, 0.434 mol) and sulfur (13.9 g, 0.434 mol). Triethylamine (43.8 g, 0.434 mol) was added dropwise to the reaction mixture using an ice-bath to control the heat release. The reaction was stirred at room temperature overnight, and then poured into a mixture of ice-water (2500 mL) and ethyl acetate (50 mL). An emulsion formed and the insoluble material was filtered. The filtrate was extracted with ethyl acetate (2×). The combined organic phases were dried and concentrated in vacuo. The resulting residue was combined with the filter cake from the previous filtration. This combined material was washed with ethyl acetate. Purification via flash chromatography afforded the title compound.

$^1$H NMR (400 MHz, DMSO): δ 7.50 (s, 4H), 7.18 (d, 2H), 6.70-6.90 (br, 1H), 5.25 (s, 1H), 1.40 (s, 6H). LRMS (APCI) calc'd for (C$_{14}$H$_{16}$FN$_2$O$_2$S) [M+H]$^+$: 313. found 313.

Intermediate 7

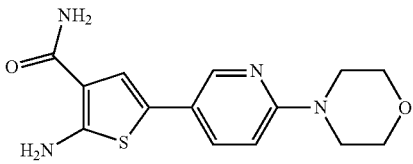 [SMILES: NC(=O)c1cc(-c2ccc(N3CCOCC3)nc2)sc1N]

2-Amino-5-(6-morpholin-4-ylpyridin-3-yl) thiophene-3-carboxamide

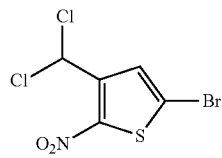 [SMILES: O=[N+]([O-])c1sc(Br)cc1C(Cl)Cl]

Step 1. 5-Bromo-3-(dichloromethyl)-2-nitrothiophene

A solution of 2-bromo-5-nitrothiophene (29 g, 139 mmol) and chloroform (12.37 mL, 153 mmol) in DMF (110 mL) was added dropwise to a solution of potassium tert-butoxide (62.6 g, 558 mmol) in THF (225 mL)/DMF (180 mL). The internal temperature was monitored and maintained at <–60° C. during the addition. Upon complete addition, the reaction was stirred at –78° C. for 30 minutes. 2 N HCl was added and the products were extracted into EtOAc (3×). The combined organic extracts were washed with brine, dried over MgSO$_4$, filtered, and concentrated in vacuo. Purification of the residue by flash silica gel column chromatography (0-10% EtOAc-hexanes) gave the title compound as a brown oil.

$^1$H NMR (600 MHz, DMSO): δ 7.88 (s, 1H), 7.70 (s, 1H).

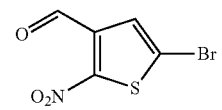

Step 2. 5-Bromo-2-nitrothiophene-3-carbaldehyde

5-Bromo-3-(dichloromethyl)-2-nitrothiophene (60.5 g, 208 mmol) and zinc chloride (113 g, 832 mmol) were stirred in refluxing formic acid (800 mL) overnight. After cooling to ambient temperature, water was added and the mixture was extracted with EtOAc (4×). The combined organic extracts were washed with brine, dried over MgSO$_4$, filtered, and concentrated in vacuo to give the title compound as an orange solid.

$^1$H NMR (600 MHz, DMSO): δ 10.27 (s, 1H), 7.66 (s, 1H).

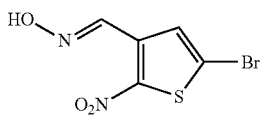 [SMILES: O=[N+]([O-])c1sc(Br)cc1/C=N/O]

Step 3. 5-Bromo-2-nitrothiophene-3-carbaldehyde oxime

5-Bromo-2-nitrothiophene-3-carbaldehyde (22.5 g, 95 mmol), hydroxylamine hydrochloride (6.96 g, 100 mmol) and sodium acetate (8.21 g, 100 mmol) were stirred in ethanol (225 mL) at room temperature overnight. The solvent was removed in vacuo, saturated NaHCO$_3$ was added and the mixture extracted with EtOAc (3×). The combined organic extracts were washed with brine, dried over MgSO$_4$, filtered, and concentrated in vacuo to give the title compound as an orange solid.

LRMS (APCI) calc'd for (C$_5$H$_4$BrN$_2$O$_3$S) [M+H]$^+$: 251, 253. Found: 251, 253.

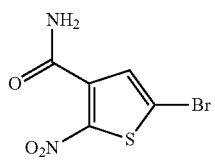

Step 4. 5-Bromo-2-nitrothiophene-3-carboxamide

5-Bromo-2-nitrothiophene-3-carbaldehyde oxime (45 g, 179 mmol), p-toluenesulfonic acid monohydrate (2.73 g, 14.34 mmol), dppe (1.428 g, 3.58 mmol) and Ru(PPh$_3$)$_3$(CO)H$_2$ (3.29 g, 3.58 mmol) were taken up in toluene (750 mL). The flask was evacuated and back-filled with N$_2$ (3×) before stirring at 111° C. under N$_2$ for 24 hours. After cooling to room temperature, the reaction mixture was purified directly by flash silica gel column chromatography (0-100% EtOAc/toluene) to give the title compound as brown needles after recrystallising from EtOH-hexanes.

$^1$H NMR (600 MHz, DMSO): δ 8.07 (s, 1H), 7.87 (s, 1H), 7.52 (s, 1H).

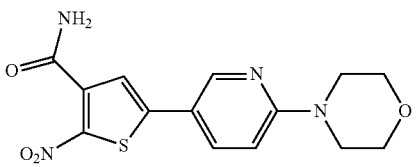

Step 5: 5-(6-Morpholin-4-ylpyridin-3-yl)-2-nitrothiophene-3-carboxamide

5-Bromo-2-nitrothiophene-3-carboxamide (2.50 g, 9.96 mmol) and 4-[5-(4,4,5,5-tetramethyl-1,3,2-dioxaborolan-2-yl)pyridine-2-yl]morpholine (2.89 g, 9.96 mmol) were combined in THF (40 ml). Tetrakis(triphenylphoshine)palladium (0) (0.58 g, 0.50 mmol) was added and the reaction mixture was heated to reflux overnight. After cooling to room temperature, the mixture was diluted with ethyl acetate (500 ml) and water (500 ml). A red solid crashed out. The mixture was filtered and the solid was washed with ethyl acetate to yield the title compound as a red solid.

LRMS (APCI) calc'd for (C$_{14}$H$_{15}$N$_4$O$_4$S) [M+H]$^+$: 335. Found: 335.

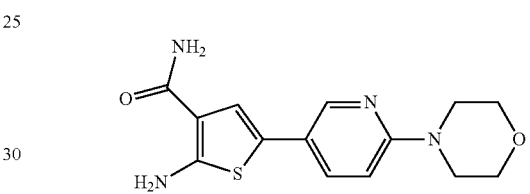

Step 6: 2-Amino-5-(6-morpholin-4-ylpyridin-3-yl)thiophene-3-carboxamide 5-(6-Morpholin-4-ylpyridin-3-yl)-2-nitrothiophene-3-carboxamide (2.77 g, 8.28 mmol), iron(III) chloride (0.03 g, 0.17 mmol), and hydrazine monohydrate (1.34 ml, 27.3 mmol) were combined in methanol (166 ml) and the reaction mixture was purged with nitrogen. The reaction was heated to 65° C. for 3 hours. After cooling to room temperature, the reaction mixture was filtered and solid was washed with methanol. Silica gel was added to the filtrate and the mixture was concentrated. The residue was purified by column chromatography on silica gel, eluting with ethyl acetate/methanol to give the title compound as an orange solid.

LRMS (APCI) called for (C$_{14}$H$_{17}$N$_4$O$_2$S) [M+H]$^+$: 305. Found: 305.

Additional analogues were prepared using procedures similar to those described in the above examples.

TABLE 1

| Intermediate # | Structure | Compound Name | Characterization [M + H]$^+$ |
|---|---|---|---|
| 8 | ![structure] | 2-amino-5-[4-(1-cyano-1-methylethyl)phenyl]thiophene-3-carboxamide | Calc'd 286, found 286 |

Example 1

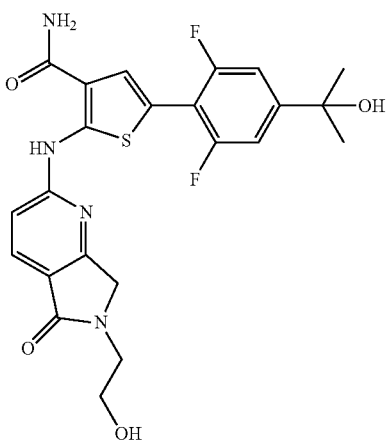 [SMILES: CC(C)(O)c1cc(F)c(-c2cc(C(N)=O)c(Nc3ccc4c(n3)CN(CCO)C4=O)s2)c(F)c1]

5-[2,6-Difluoro-4-(1-hydroxy-1-methylethyl)phenyl]-2-{[6-(2-hydroxyethyl)-5-oxo-6,7-dihydro-5H-pyrrolo[3,4-b]pyridin-2-yl]amino}thiophene-3-carboxamide

Step 1. Methyl 2-methylpyridine-3-carboxylate 1-oxide

Methyl 2-methylpyridine-3-carboxylate (10 g, 66.2 mmol) was taken up in DCM (140 mL) and mCPBA (16.31 g, 72.8 mmol) was added. The resulting solution was stirred at room temperature overnight. The reaction mixture was purified directly by silica gel chromatography (0-20% MeOH/EtOAc) to afford the title compound as a beige solid.

$^1$H NMR (600 MHz, CDCl$_3$): δ 8.56 (dd, J=4.8 and 1.8Hz, 1H), 8.14 (dd, J=8.4 and 1.8Hz, 1 H), 7.16 (dd, J=8.4 and 4.8Hz, 1H), 3.87 (s, 3H), 2.79 (s, 3H).

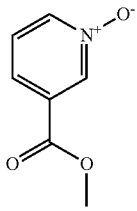

Step 2. Methyl 6-chloro-2-methylpyridine-3-carboxylate and methyl 2-(chloromethyl)pyridine-3-carboxylate Methyl 2-methylpyridine-3-carboxylate 1-oxide (2.93 g, 17.53 mmol) was stirred in refluxing POCl$_3$ (17 mL, 182 mmol) for 3 hours. Room temperature was attained and the reaction mixture poured into ice-water. The resulting dark solution was neutralised with solid Na$_2$CO$_3$ and the mixture was extracted with EtOAc (3×). The combined organic extracts were washed with brine, dried over MgSO$_4$, filtered, and concentrated in vacuo. Purification of the residue by silica gel chromatography (2-30% EtOAc/hexanes) gave methyl 6-chloro-2-methylpyridine-3-carboxylate as a pale yellow oil (A) and methyl 2-(chloromethyl)pyridine-3-carboxylate (B) as an orange oil.

A—$^1$H NMR (600 MHz, CDCl$_3$): δ 8.13 (d, J=8.4Hz, 1H), 7.21 (d, J=8.4Hz, 1H), 3.89 (s, 3 H), 2.79 (s, 3H).

B—$^1$H NMR (600 MHz, CDCl$_3$): δ 8.70 (dd, J=5.4 and 1.8Hz, 1H), 8.26 (dd, J=7.8 and 1.8 Hz, 1H), 7.34 (dd, J=7.8 and 5.4Hz, 1H), 3.87 (s, 3H), 2.79 (s, 3H).

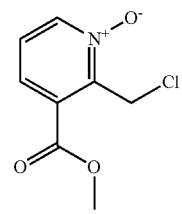

Step 3. Methyl 2-(chloromethyl)pyridine-3-carboxylate 1-oxide

Methyl 2-(chloromethyl)pyridine-3-carboxylate (4.45 g, 23.98 mmol) was taken up in DCM (50 mL) and mCPBA (5.91 g, 26.4 mmol) was added. The resulting solution was stirred at room temperature overnight. The reaction mixture was then purified directly by silica gel chromatography (0-20% MeOH/EtOAe) to give methyl 2-(chloromethyl)pyridine-3-carboxylate 1-oxide as a white solid.

$^1$H NMR (600 MHz, CDCl$_3$): δ 8.22 (d, J=8.4Hz, 1H), 7.37 (d, J=8.4Hz, 1H), 5.03 (s, 2H), 3.95 (s, 3H).

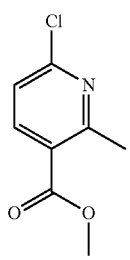 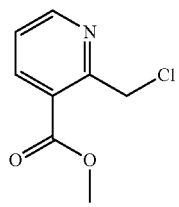

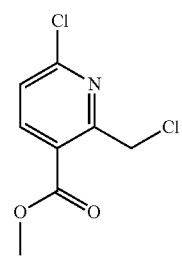

-continued

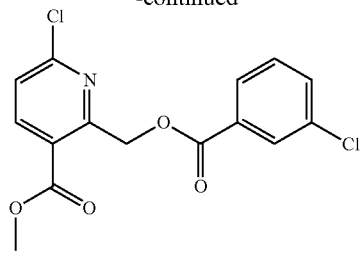

Step 4. Methyl 6-chloro-2-(chloromethyl)pyridine-3-carboxylate and methyl 6-chloro-2-({[(3-chlorophenyl)carbonyl]oxy}methyl)pyridine-3-carboxylate Methyl 2-(chloromethyl)pyridine-3-carboxylate 1-oxide (17.85 g, 89 mmol) was stirred in refluxing $POCl_3$ (80 mL, 858 mmol) for 3 hours. Room temperature was attained and the reaction mixture poured into ice-water. The resulting beige precipitate was collected by filtration and purified by silica gel chromatography (2-20% EtOAc/hexanes) to give methyl 6-chloro-2-(chloromethyl)pyridine-3-carboxylate (A) as a white solid and methyl 6-chloro-2-({[(3-chlorophenyl)carbonyl]oxy}methyl)pyridine-3-carboxylate (B) as a yellow solid.
A—LRMS (APCI) calc'd for $(C_8H_8Cl_2NO_2)$ [M+1]$^+$: 220, 222. Found: 220, 222.
B—LRMS (APCI) calc'd for $(C_{15}H_{12}Cl_2NO_4)$ [M+1]$^+$: 340, 342. Found: 340, 342.

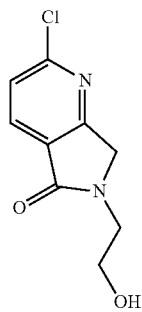 [SMILES: O=C1c2ccc(Cl)nc2CN1CCO]

Step 5. 2-Chloro-6-(2-hydroxyethyl)-6,7-dihydro-5H-pyrrolo[3,4-b]pyridin-5-one Methyl 6-chloro-2-(chloromethyl)pyridine-3-carboxylate (0.1 g, 0.45 mmol) and ethanolamine (0.11 mL, 1.82 mmol) were stirred in MeOH (10 mL) at room temperature overnight. Additional ethanolamine (0.11 mL, 1.82 mmol) was added and stirring continued for 8 hours. Additional ethanolamine (0.22 mL, 3.64 mmol) was then added and stirring continued for 3 days. The solvent was removed in vacuo and the residue purified by silica gel chromatography (0-5% MeOH/EtOAc) to give the title compound as a white solid.

LRMS (APCI) calc'd for $(C_9H_{10}ClN_2O_2)$ [M+H]$^+$, 213. found 213.

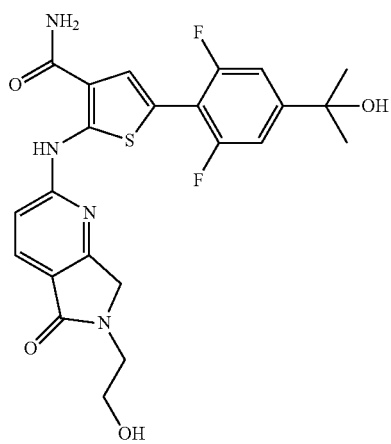 [SMILES: CC(C)(O)c1cc(F)c(-c2cc(C(N)=O)c(Nc3ccc4c(n3)CN(CCO)C4=O)s2)c(F)c1]

Step 6 5-[2,6-Difluoro-4-(1-hydroxy-1-methylethyl)phenyl]-2-{[6-(2-hydroxyethyl)-5-oxo-6,7-dihydro-5H-pyrrolo[3,4-b]pyridin-2-yl]amino}thiophene-3-carboxamide 2-Amino-5-[2,6-difluoro-4-(1-hydroxy-1-methylethyl)phenyl]thiophene-3-carboxamide (90 mg, 0.29 mmol), 2-chloro-6-(2-hydroxyethyl)-6,7-dihydro-5H-pyrrolo[3,4-b]pyridin-5-one (61 mg, 0.29 mmol), $Pd_2dba_3$ (26.4 mg, 0.029 mmol), $K_2CO_3$ (43.8 mg, 0.317 mmol) and X-Phos (68.7 mg, 0.144 mmol) were added to a 2 mL microwave vial. Degassed tert-amyl alcohol (0.7 mL) was added and the vial evacuated and back-filled with nitrogen (3×). The resulting mixture was stirred at 100° C. overnight. Room temperature was attained, MeOH was added and the resulting mixture filtered through Celite. The filtrate was concentrated in vacuo while loading onto silica. Purification of the residue by silica gel chromatography (0-20% MeOH/EtOAc) gave the title compound as a pale yellow solid after triturating in EtOH. LRMS (APCI) calc'd for $(C_{23}H_{23}F_2N_4O_4S)$ [M+H]$^+$, 489. found 489.

Additional analogues were prepared using procedures similar to those described in the above examples.

TABLE 2

| Example # | Structure | Compound Name | Characterization [M + H]+ |
|---|---|---|---|
| 2 | 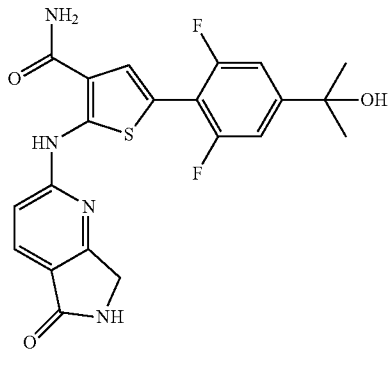 [SMILES: CC(C)(O)c1cc(F)c(-c2cc(C(N)=O)c(Nc3ccc4c(n3)CNC4=O)s2)c(F)c1] | 5-[2,6-difluoro-4-(1-hydroxy-1-methylethyl)phenyl]-2-[(5-oxo-6,7-dihydro-5H-pyrrolo[3,4-b]pyridin-2-yl)amino]thiophene-3-carboxamide | Calc'd: 445, Found: 445 |
| 3 | 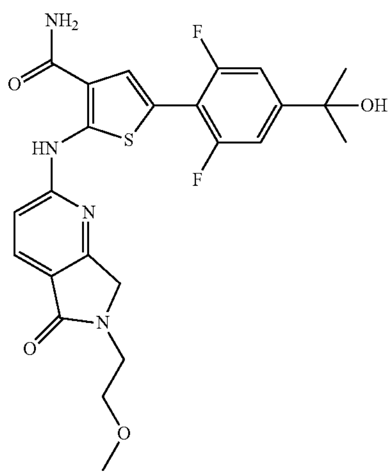 [SMILES: COCCN1Cc2nc(Nc3sc(-c4c(F)cc(C(C)(C)O)cc4F)cc3C(N)=O)ccc2C1=O] | 5-[2,6-difluoro-4-(1-hydroxy-1-methylethyl)phenyl]-2-{[6-(2-methoxyethyl)-5-oxo-6,7-dihydro-5H-pyrrolo[3,4-b]pyridin-2-yl]amino}thiophene-3-carboxamide | Calc'd: 503, Found: 503 |
| 4 | 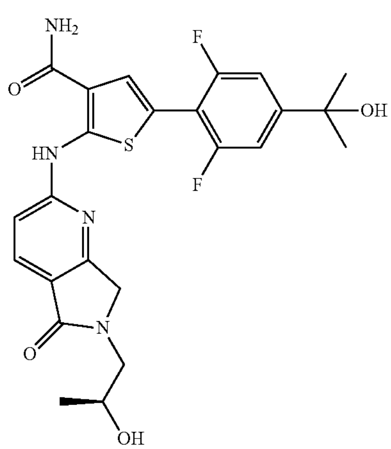 [SMILES: C[C@H](O)CN1Cc2nc(Nc3sc(-c4c(F)cc(C(C)(C)O)cc4F)cc3C(N)=O)ccc2C1=O] | 5-[2,6-difluoro-4-(1-hydroxy-1-methylethyl)phenyl]-2-({6-[(2S)-2-hydroxypropyl]-5-oxo-6,7-dihydro-5H-pyrrolo[3,4-b]pyridin-2-yl}amino)thiophene-3-carboxamide | Calc'd: 503, Found: 503 |

TABLE 2-continued

| Example # | Structure | Compound Name | Characterization [M + H]+ |
|---|---|---|---|
| 5 | 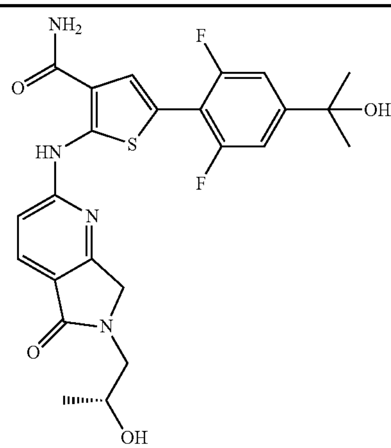 | 5-[2,6-difluoro-4-(1-hydroxy-1-methylethyl)phenyl]-2-({6-[(2R)-2-hydroxypropyl]-5-oxo-6,7-dihydro-5H-pyrrolo[3,4-b]pyridin-2-yl}amino)thiophene-3-carboxamide | Calc'd: 503, Found: 503 |
| 6 | 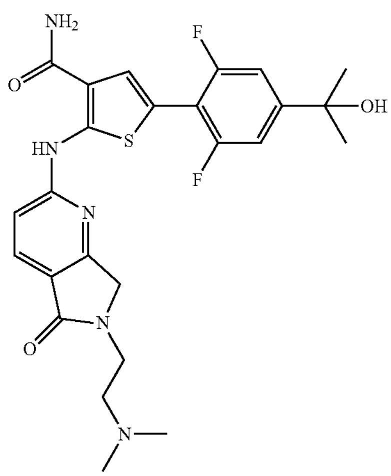 [SMILES: CN(C)CCN1Cc2nc(Nc3sc(-c4c(F)cc(C(C)(C)O)cc4F)cc3C(N)=O)ccc2C1=O] | 5-[2,6-difluoro-4-(1-hydroxy-1-methylethyl)phenyl]-2-({6-[2-(dimethylamino)ethyl]-5-oxo-6,7-dihydro-5H-pyrrolo[3,4-b]pyridin-2-yl}amino)thiophene-3-carboxamide | Calc'd: 516, Found: 516 |

Example 7

5-[2,6-Difluoro-4-(1-hydroxy-1-methylethyl)phenyl]-2-[(6-methyl-5-oxo-6,7-dihydro-5H-pyrrolo[3,4-b]pyridin-2-yl)amino]thiophene-3-carboxamide Step 1. 2-Chloro-6-methyl-6,7-dihydro-5H-pyrrolo[3A-b]pyridin-5-one Methyl 6-chloro-2-(chloromethyl)pyridine-3-carboxylate (Example 1 Step 4) (1.5 g, 6.82 mmol) was stirred in a solution of methylamine in THF (35 mL, 70.0 mmol) at room temperature overnight. Water was added and the mixture extracted with EtOAc (2×). The combined organic extracts were washed with brine, dried over MgSO₄, filtered, and concentrated in vacuo. The residue was triturated in diethyl ether to give batch 1 of the title compound. The mother liquor was concentrated in vacuo and the residue purified by MPLC (40-100% EtOAc-hexanes) and combined with batch 1 to give the title compound as a white solid.

LRMS (APCI) calc'd for ($C_8H_8ClN_2O$) [M+H]⁺, 183, 185. found 183, 185.

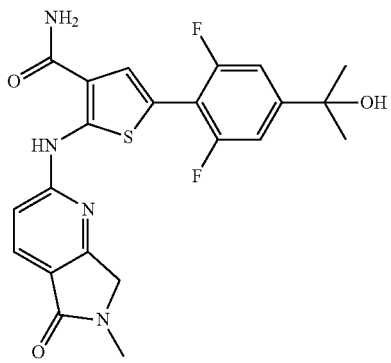 [SMILES: CN1Cc2nc(Nc3sc(-c4c(F)cc(C(C)(C)O)cc4F)cc3C(N)=O)ccc2C1=O]

Step 2 5-[2,6-Difluoro-4-(1-hydroxy-1-methylethyl) phenyl]-2-[(6-methyl-5-oxo-6,7-dihydro-5H-pyrrolo [3,4-b]pyridin-2-yl)amino]thiophene-3-carboxamide The title compound was prepared according to the general procedure in Example 1 Step 5 using 2-amino-5-[2,6-difluoro-4-(1-hydroxy-1-methylethyl)phenyl]thiophene-3-carboxamide (75 mg, 0.240 mmol) and 2-chloro-6-methyl-6,7-dihydro-5H-pyrrolo[3,4-b]pyridin-5-one (43.8 mg, 0.240 mmol) as the starting materials.

LRMS (APCI) calc'd for ($C_{22}H_{21}F_2N_4O_3S$) [M+H]⁺, 459. found 459.

Additional analogues were prepared using procedures similar to those described in the above examples.

TABLE 3

| Example # | Structure | Compound Name | Characterization [M + H]⁺ |
|---|---|---|---|
| 8 | 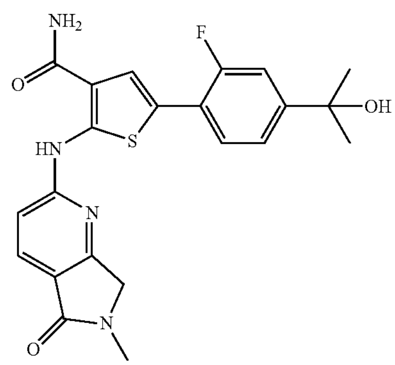 [SMILES: CN1Cc2nc(Nc3sc(-c4ccc(C(C)(C)O)cc4F)cc3C(N)=O)ccc2C1=O] | 5-[2-fluoro-4-(1-hydroxy-1-methylethyl)phenyl]-2-[(6-methyl-5-oxo-6,7-dihydro-5H-pyrrolo[3,4-b]pyridin-2-yl)amino]thiophene-3-carboxamide | Calc'd: 441, Found: 441 |
| 9 | 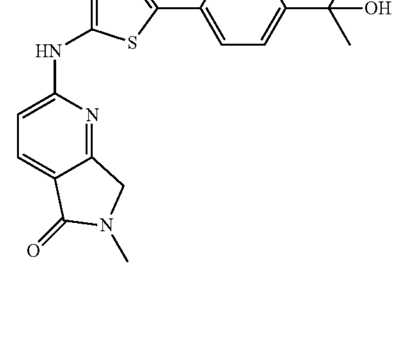 | 5-[4-(1-hydroxy-1-methylethyl)phenyl]-2-[(6-methyl-5-oxo-6,7-dihydro-5H-pyrrolo[3,4-b]pyridin-2-yl)amino]thiophene-3-carboxamide | Calc'd: 423, Found: 423 |

TABLE 3-continued

| Example # | Structure | Compound Name | Characterization [M + H]⁺ |
|---|---|---|---|
| 10 | 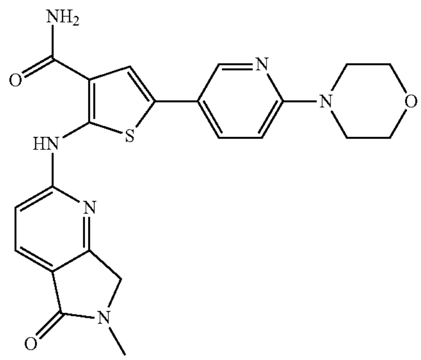 [SMILES: CN1Cc2nc(Nc3sc(-c4ccc(N5CCOCC5)nc4)cc3C(N)=O)ccc2C1=O] | 2-[(6-methyl-5-oxo-6,7-dihydro-5H-pyrrolo[3,4-b]pyridin-2-yl)amino]-5-(6-morpholin-4-ylpyridin-3-yl)thiophene-3-carboxamide | Calc'd: 451, Found: 451 |
| 11 | 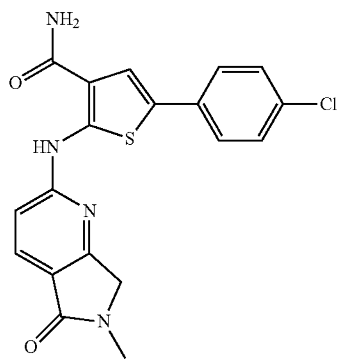 [SMILES: CN1Cc2nc(Nc3sc(-c4ccc(Cl)cc4)cc3C(N)=O)ccc2C1=O] | 5-(4-chlorophenyl)-2-[(6-methyl-5-oxo-6,7-dihydro-5H-pyrrolo[3,4-b]pyridin-2-yl)amino]thiophene-3-carboxamide | Calc'd: 399, 401, Found: 399, 401 |
| 12 | 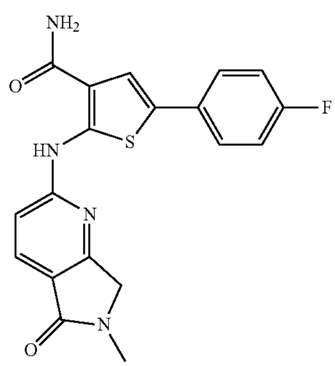 [SMILES: CN1Cc2nc(Nc3sc(-c4ccc(F)cc4)cc3C(N)=O)ccc2C1=O] | 5-(4-fluorophenyl)-2-[(6-methyl-5-oxo-6,7-dihydro-5H-pyrrolo[3,4-b]pyridin-2-yl)amino]thiophene-3-carboxamide | Calc'd: 383, Found: 383 |
| 13 | 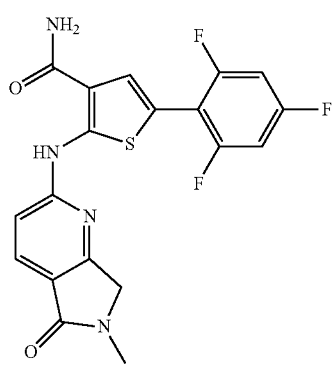 [SMILES: CN1Cc2nc(Nc3sc(-c4c(F)cc(F)cc4F)cc3C(N)=O)ccc2C1=O] | 2-[(6-methyl-5-oxo-6,7-dihydro-5H-pyrrolo[3,4-b]pyridin-2-yl) amino]-5-(2,4,6-trifluorophenyl)thiophene-3-carboxamide | Calc'd: 419, Found: 419 |

TABLE 3-continued

| Example # | Structure | Compound Name | Characterization [M + H]+ |
|---|---|---|---|
| 14 | 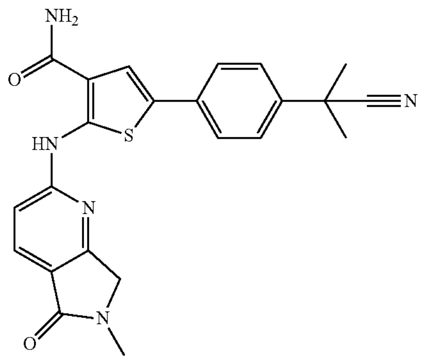 [SMILES: CN1Cc2nc(Nc3sc(-c4ccc(C(C)(C)C#N)cc4)cc3C(N)=O)ccc2C1=O] | 5-[4-(1-cyano-1-methylethyl)phenyl]-2-[(6-methyl-5-oxo-6,7-dihydro-5H-pyrrolo[3,4-b]pyridin-2-yl)amino]thiophene-3-carboxamide | Calc'd: 432, Found: 432 |
| 15 | 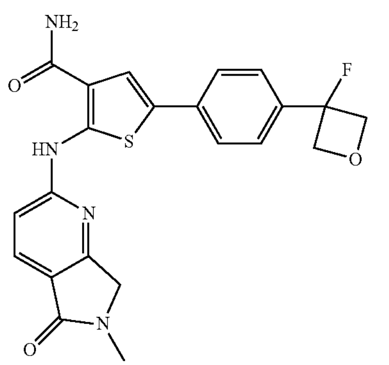 [SMILES: CN1Cc2nc(Nc3sc(-c4ccc(C5(F)COC5)cc4)cc3C(N)=O)ccc2C1=O] | 5-[4-(3-fluorooxetan-3-yl)phenyl]-2-[(6-methyl-5-oxo-6,7-dihydro-5H-pyrrolo[3,4-b]pyridin-2-yl)amino]thiophene-3-carboxamide | Calc'd: 439, Found: 439 |
| 16 | 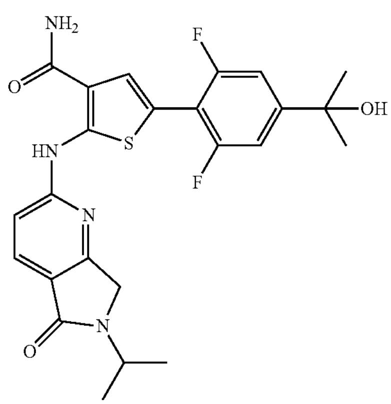 [SMILES: CC(C)N1Cc2nc(Nc3sc(-c4c(F)cc(C(C)(C)O)cc4F)cc3C(N)=O)ccc2C1=O] | 5-[2,6-difluoro-4-(1-hydroxy-1-methylethyl)phenyl]-2-[(6-isopropyl-5-oxo-6,7-dihydro-5H-pyrrolo[3,4-b]pyridin-2-yl)amino]thiophene-3-carboxamide | Calc'd: 487, Found: 487 |

Example 17

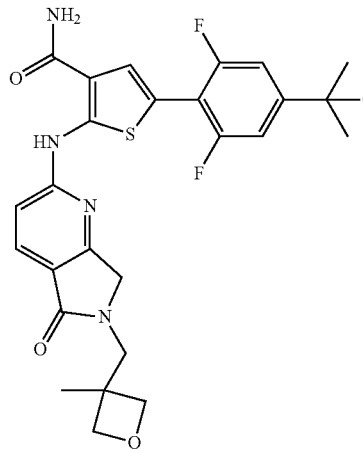

5-[2,6-Difluoro-4-(1-hydroxy-1-methylethyl)phenyl]-2-({6-[(3-methyloxetan-3-yl)methyl]-5-oxo-6,7-dihydro-5H-pyrrolo[3,4-b]pyridin-2-yl}amino)thiophene-3-carboxamide

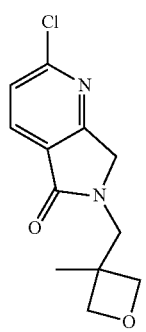 [SMILES: CC1(CN2Cc3nc(Cl)ccc3C2=O)COC1]

Step 1. 2-Chloro-6-methyl-6.,7-dihydro-5H-pyrrolo[3A-b]pyridin-5-one

Methyl 6-chloro-2-(chloromethyl)pyridine-3-carboxylate (Example 1, Step 4) (0.5 g, 2.27 mmol), DIPEA (1.19 mL, 6.82 mmol) and 1-(3-methyloxetan-3-yl)methanamine (0.46 g, 4.54 mmol) were stirred in DMF (25 mL) at room temperature for 3 days. The solvent was removed in vacuo, saturated aqueous NaHCO$_3$ was added. The mixture was extracted with EtOAc (x2) and the combined organic extracts were washed with 1N HCl, dried over MgSO$_4$ and concentrated in vacuo to give the title compound as an off-white solid.

LRMS (APCI) calc'd for ($C_{12}H_{14}ClN_2O_2$) [M+H]$^+$, 253, 255. found 253, 255.

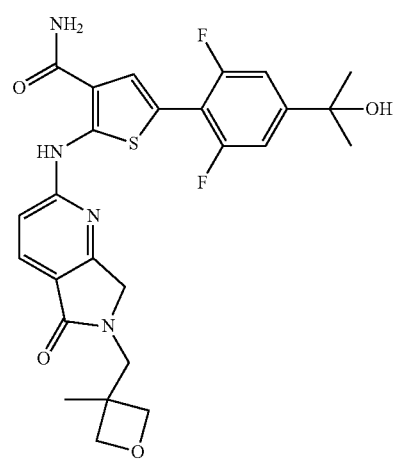 [SMILES: CC1(CN2Cc3nc(Nc4sc(-c5c(F)cc(C(C)(C)O)cc5F)cc4C(N)=O)ccc3C2=O)COC1]

Step 2 5-[2,6-Difluoro-4-(1-hydroxy-1-methylethyl)phenyl]-2-({6-[(3-methyloxetan-3-yl)methyl]-5-oxo-6,7-dihydro-5H-pyrrolo[3,4-b]pyridin-2-yl}amino)thiophene-3-carboxamide The title compound was prepared according to the general procedure in Example 1 Step 5 using 2-amino-5-[2,6-difluoro-4-(1-hydroxy-1-methylethyl)phenyl]thiophene-3-carboxamide (130 mg, 0.42 mmol) and 2-chloro-6-[(3-methyloxetan-3-yl)methyl]-6,7-dihydro-5H-pyrrolo[3,4-b]pyridin-5-one (100 mg, 0.40 mmol) as the starting materials.

LRMS (APCI) calc'd for ($C_{26}H_{27}F_2N_4O_4S$) [M+H]$^+$, 529. found 529.

Additional analogues were prepared using procedures similar to those described in the above examples.

TABLE 4

| Example # | Structure | Compound Name | Characterization [M + H]+ |
|---|---|---|---|
| 18 | 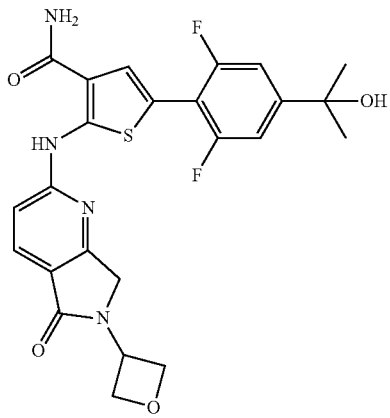 [SMILES: CC(C)(O)c1cc(F)c(-c2cc(C(N)=O)c(Nc3ccc4c(n3)CN(C3COC3)C4=O)s2)c(F)c1] | 5-[2,6-difluoro-4-(1-hydroxy-1-methylethyl)phenyl]-2-{[6-(1,3-oxazol-2-ylmethyl)-5-oxo-6,7-dihydro-5H-pyrrolo[3,4-b]pyridin-2-yl]amino}thiophene-3-carboxamide | Calc'd: 526, Found: 526 |

Example 19

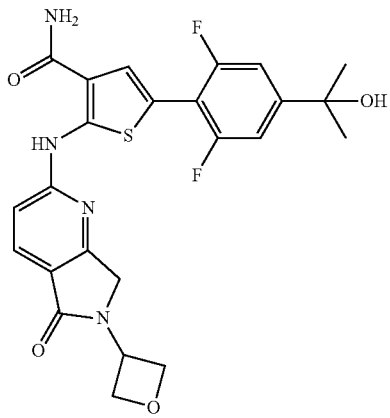 [SMILES: CC(C)(O)c1cc(F)c(-c2cc(C(N)=O)c(Nc3ccc4c(n3)CN(C3COC3)C4=O)s2)c(F)c1]

5-[2,6-Difluoro-4-(1-hydroxy-1-methylethyl)phenyl]-2-[(6-oxetan-3-yl-5-oxo-6,7-dihydro-5H-pyrrolo[3,4-b]pyridin-2-yl)amino]thiophene-3-carboxamide

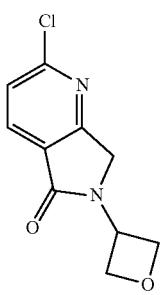 [SMILES: O=C1c2ccc(Cl)nc2CN1C1COC1]

Step 1. 2-Chloro-6-oxetan-3-yl-6,7-dihydro-5H-pyrrolo[3,4-b]pyridin-5-one

Methyl 6-chloro-2-(chloromethyl)pyridine-3-carboxylate (Example 1, Step 4) (0.15 g, 0.68 mmol), oxetan-3-amine hydrochloride (0.15 g, 1.36 mmol) and potassium carbonate (0.38 g, 2.7 mmol) were stirred in DMF (10 mL) at room temperature overnight. Water and ethyl acetate were added and the biphasic mixture was extracted with ethyl acetate (2×). The combined organic extracts were washed with brine, dried over MgSO$_4$, filtered, and concentrated in vacuo. Purification of the residue by silica gel chromatography (6-50% EtOAc/hexanes) gave the title compound as a white solid.

LRMS (APCI) calc'd for (C$_{10}$H$_{10}$ClN$_2$O$_2$) [M+H]+, 225, 227. found 225, 227.

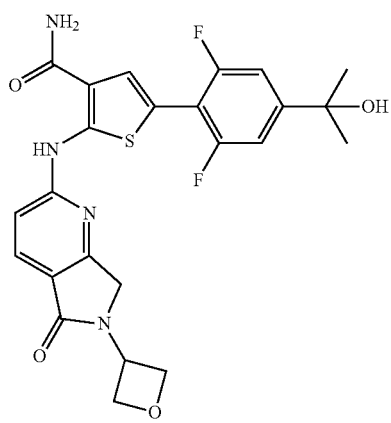 [SMILES: CC(C)(O)c1cc(F)c(-c2cc(C(N)=O)c(Nc3ccc4c(n3)CN(C3COC3)C4=O)s2)c(F)c1]

Step 2 5-[2,6-Difluoro-4-(1-hydroxy-1-methylethyl)phenyl]-2-[(6-oxetan-3-yl-5-oxo-6,7-dihydro-5H-pyrrolo[3,4-b]pyridin-2-yl)amino]thiophene-3-carboxamide The title compound was prepared according to the general procedure in Example 1 Step 5 using 2-amino-5-[2,6-difluoro-4-(1-hydroxy-1-methylethyl)phenyl]thiophene-3-carboxamide (55 mg, 0.176 mmol) and 2-chloro-6-oxetan-3-yl-6,7-dihydro-5H-pyrrolo[3,4-b]pyridin-5-one (39.6 mg, 0.176 mmol) as the starting materials.

LRMS (APCI) calc'd for ($C_{24}H_{23}F_2N_4O_4S$) [M+H]+, 501. found 501.

Example 20

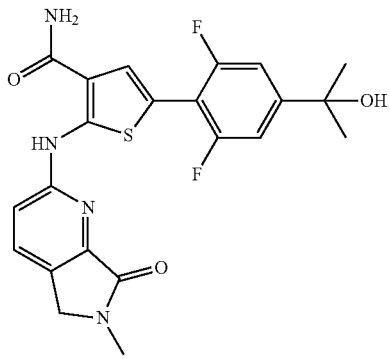 [SMILES: CN1Cc2ccc(Nc3sc(-c4c(F)cc(C(C)(C)O)cc4F)cc3C(N)=O)nc2C1=O]

5-[2,6-Difluoro-4-(1-hydroxy-1-methylethyl)phenyl]-2-[[(6-methyl-7-oxo-6,7-dihydro-5H-pyrrolo[3,4-b]pyridin-2-yl)amino]thiophene-3-carboxamide

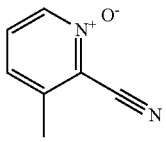

Step 1. 3-Methylpyridine-2-carbonitrile 1-oxide

3-Methylpyridine-2-carbonitrile (10 g, 85 mmol) was taken up in DCM (180 mL) and mCPBA (20.9 g, 93 mmol) was added. The resulting mixture was stirred at room temperature overnight. Additional mcpba (9.49 g, 42 mmol) was added and stirring continued at room temperature for 24 hours. Saturated aqueous NaHCO$_3$ and the resulting mixture was extracted with EtOAc (3×), followed by 20% MeOH—CHCl$_3$ (2×). The combined organic extracts were dried over MgSO$_4$, filtered, and concentrated in vacuo. Purification of the residue by silica gel chromatography (0-20% MeOH/EtOAc) gave the title compound as a white solid.

$^1$H NMR (600 MHz, DMSO): δ 8.26 (m, 1H), 7.54 (m, 1H), 7.37 (m, 1H), 2.40 (s, 3H).

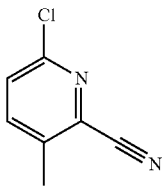

Step 2. 6-Chloro-3-methylpyridine-2-carbonitrile

3-Methylpyridine-2-carbonitrile 1-oxide (8.42 g, 62.8 mmol) was stirred in refluxing POCl$_3$ (60 mL, 646 mmol) for 6 hours. The mixture was cooled to room temperature and slowly poured into ice-water. The resulting beige precipitate was collected by filtration to give the title compound.

$^1$H NMR (600 MHz, CDCl$_3$): δ 7.62 (d, J=8.4Hz, 1H), 7.43 (d, J=8.4Hz, 1H), 2.53 (s, 3H).

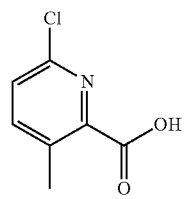

Step 3. 6-Chloro-3-methylpyridine-2-carboxylic acid

6-Chloro-3-methylpyridine-2-carbonitrile (2.95 g, 19.3 mmol) and Potassium hydroxide (3.25 g, 58 mmol) were stirred in refluxing water (60 mL) for 2 hours. The mixture was cooled to room temperature, 30 mL of 2 N HCl was added, followed by the addition of water. The resulting mixture was extracted with EtOAc (3×). The combined organic extracts were washed with brine, dried over MgSO$_4$, filtered, and concentrated in vacuo to give the title compound as a white solid.

$^1$H NMR (600 MHz, DMSO): δ 13.45 (br s, 1H), 7.81 (d, J=8.4Hz, 1H), 7.55 (d, J=8.4Hz, 1H), 2.39 (s, 3H).

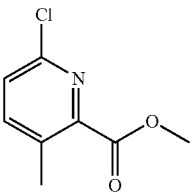

Step 4. Methyl 6-chloro-3-methylpyridine-2-carboxylate

6-Chloro-3-methylpyridine-2-carboxylic acid (3.69 g, 21.51 mmol) was taken up in THF (100 mL)/MeOH (25 mL). A solution of TMS-diazomethane (21.5 mL, 43.0 mmol) was added and the resulting solution stirred at room temperature for 2 hours. The solvent was removed in vacuo and the residue purified by silica gel chromatography (2-20% EtOAc/hexanes) to give the title compound as a white solid.

LRMS (APCI) calcd for ($C_8H_9ClNO_2$) [M+H]$^+$: 186, 188. Found: 186, 188.

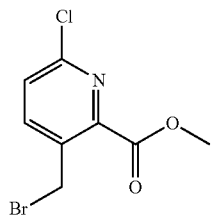

Step 5. Methyl 3-(bromomethyl)-6-chloropyridine-2-carboxylate

Methyl 6-chloro-3-methylpyridine-2-carboxylate (3.46 g, 18.6 mmol), NBS (3.32 g, 18.6 mmol) and AIBN (61 mg, 0.37 mmol) were stirred in refluxing $CCl_4$ (40 mL) for 6 hours. The mixture was then cooled to room temperature and purified directly by silica gel chromatography (2-20% EtOAc/hexanes) to give the title compound as a white solid.

LRMS (APCI) calc'd for ($C_8H_8BrClNO_2$) [M+H]$^+$, 266. found 266.

Step 6. 2-Chloro-6-methyl-5,6-dihydro-7H-pyrrolo[3,4-b]pyridin-7-one

2-Chloro-6-methyl-5,6-dihydro-7H-pyrrolo[3,4-b]pyridin-7-one was prepared according to the general procedure in Example 7 Step 1 using methyl 3-(bromomethyl)-6-chloropyridine-2-carboxylate (0.40 g, 1.49 mmol) and methylamine, 2 M in THF (10 mL, 20 mmol) as the starting materials.

LRMS (APCI) calc'd for ($C_8H_8ClN_2O$) [M+H]$^+$, 183. found 185.

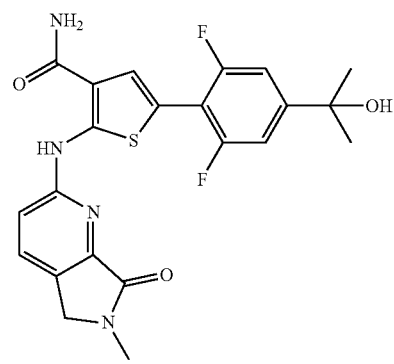 [SMILES: CN1Cc2ccc(Nc3sc(-c4c(F)cc(C(C)(C)O)cc4F)cc3C(N)=O)nc2C1=O]

Step 7. 5-[2,6-Difluoro-4-(1-hydroxy-1-methylethyl)phenyl]-2-[(6-methyl-7-oxo-6,7-dihydro-5H-pyrrolo[3,4-b]pyridin-2-yl)amino]thiophene-3-carboxamide The title compound was prepared according to the procedure in Example 1 Step 5 using 2-amino-5-[2,6-difluoro-4-(1-hydroxy-1-methylethyl)phenyl]thiophene-3-carboxamide (100 mg, 0.32 mmol) and 2-chloro-6-methyl-5,6-dihydro-7H-pyrrolo[3,4-b]pyridin-7-one (52.6 mg, 0.29 mmol) as the starting materials.

LRMS (APCI) calc'd for ($C_{22}H_{21}F_2N_4O_3S$) [M+H]$^+$, 459. found 459.

Additional analogues were prepared using procedures similar to those described in the above examples.

TABLE 5

| Example # | Structure | Compound Name | Characterization |
|---|---|---|---|
| 21 | 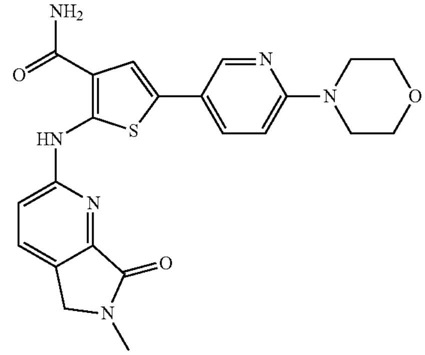 [SMILES: CN1Cc2ccc(Nc3sc(-c4ccc(N5CCOCC5)nc4)cc3C(N)=O)nc2C1=O] | 2-[(6-methyl-7-oxo-6,7-dihydro-5H-pyrrolo[3,4-b]pyridin-2-yl)amino]-5-(6-morpholin-4-ylpyridin-3-yl)thiophene-3-carboxamide | Calc'd [M + H]$^+$: 451, Found: 445 |

Example 22

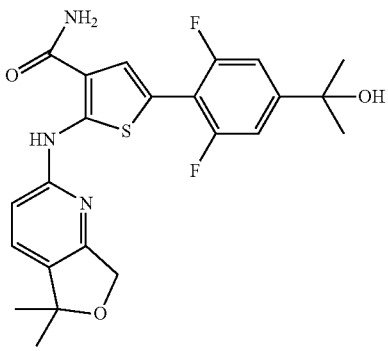 [SMILES: CC(C)(O)c1cc(F)c(-c2cc(C(N)=O)c(Nc3ccc4c(n3)COC4(C)C)s2)c(F)c1]

5-[2,6-Difluoro-4-(1-hydroxy-1-methylethyl)phenyl]-2-[(5,5-dimethyl-5,7-dihydrofuro[3,4-b]pyridin-2-yl)amino]thiophene-3-carboxamide

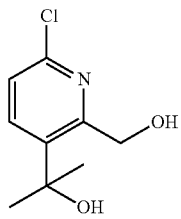

Step 1: 2-[6-Chloro-2-(hydroxymethyl)pyridin-3-yl]propan-2-ol

Methyl 6-chloro-2-{[(3-chlorobenzoyl)oxy]methyl}nicotinate (Example 1, Step 4) (1 g, 2.94 mmol) was taken up in tetrahydrofuran (14.7 ml) and cooled to 0° C. Methylmagnesium bromide (5.9 ml of 3.0M in diethyl ether, 17.6 mmol) was added dropwise. The reaction was stirred for two hours, then allowed to reach room temperature and left to stir overnight. The reaction was quenched with saturated aqueous ammonium chloride and extracted with ethyl acetate (2×). The combined organics were dried over anhydrous magnesium sulfate, filtered, and concentrated in vacuo. Purification via flash chromatography (silica, 0-60% ethyl acetate/hexanes) afforded the title compound as a light orange oil.

$^1$H NMR (500 MHz, CDCl$_3$): δ 7.64 (d, 1H), 7.21 (d, 1H), 497 (s, 2H), 430 (s, 1H), 2.02 (s, 1H), 1.63 (s, 6H).

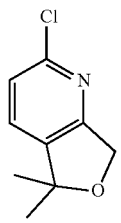

Step 2: 2-Chloro-5,5-dimethyl-5,7-dihydrofuro[3,4-b]pyridine

2-[6-Chloro-2-(hydroxymethyl)pyridin-3-yl]propan-2-ol (200 mg, 0.99 mmol) was taken up in tetrahydrofuran (5 mL) and cooled to −78° C. n-Butyllithium (1.24 mL 011.6 M in hexanes, 1.98 mmol) was added dropwise and the mixture was allowed to stir for 30 minutes. p-Toluenesulfonylchloride (190 mg, 0.99 mmol) was then added in one portion and the mixture was allowed to warm to room temperature warm slowly to 0° C. over two hours and then left to warm to room temperature overnight. The reaction was quenched with saturated aqueous ammonium chloride and the biphasic mixture was extracted with ethyl acetate (2×). The combined organics were dried over magnesium sulfate, filtered, and concentrated in vacuo. The resulting residue was purified via flash chromatography (silica, 0-50% ethyl acetate/hexanes) to afford the title compound as a colorless oil.

$^1$H NMR (500 MHz, CDCl$_3$): δ 7.39 (d, 1H), 7.21 (d, 1H), 5.00 (s, 2H), 1.51 (s, 6H).

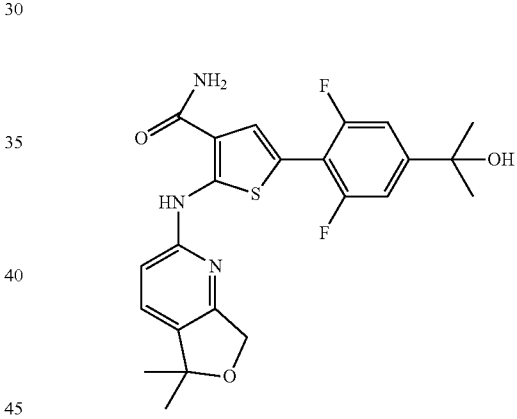

Step 3: 5-[2,6-Difluoro-4-(1-hydroxy-1-methylethyl)phenyl]-2-[(5,5-dimethyl-5,7-dihydrofuro[3,4-b]pyridin-2-yl)amino]thiophene-3-carboxamide The title compound was prepared as described in Example 1, Step 5 using 2-amino-5-[2,6-difluoro-4-(1-hydroxy-1-methylethyl)phenyl]thiophene-3-carboxamide (185 mg, 0.59 mmol) and 2-chloro-5,5-dimethyl-5,7-dihydrofuro[3,4-h]pyridine (110 mg, 0.60 mmol) as starting materials.

$^1$H NMR (500 MHz, d6-DMSO): δ 12.21 (s, 1H), 7.89 (s, 1H), 7.75 (s, 1H), 7.65 (d, 1H), 7.38 (s, 1H), 7.25 (d, 2H), 6.97

(d, 1H), 5.29 (s, 1H), 4.89 (s, 2H), 1.42 (s, 12H). LRMS (APCI) calc'd for (C$_{23}$H$_{24}$F$_2$N$_3$O$_3$S) [M+H]$^+$: 460. found 460.

Example 23

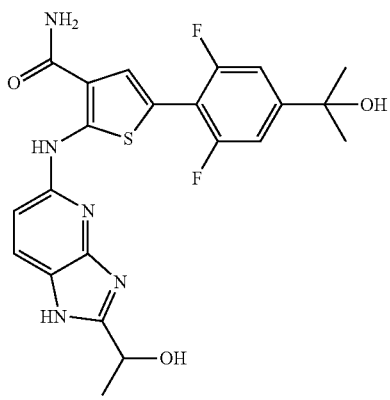 [SMILES: CC(O)c1nc2nc(Nc3sc(-c4c(F)cc(C(C)(C)O)cc4F)cc3C(N)=O)ccc2[nH]1]

5-[2,6-Difluoro-4-(1-hydroxy-1-methylethyl)phenyl]-2-{[2-(1-hydroxyethyl)-1H-imidazo[4,5-b]pyridin-5-yl]amino}thiophene-3-carboxamide

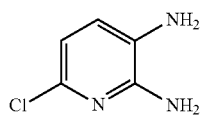

Step 1: 6-Chloropyridine-2,3-diamine

A flask was charged with 6-chloro-3-nitropyridin-2-amine (500 mg, 2.88 mmol) and tin(II) chloride dihydrate (3.25 g, 14.40 mmol) under argon. A 9:1 mixture of ethyl acetate:2-methyl-2-propanol was then added, and the reaction was allowed to stir at 60° C. for one hour. Sodium borohydride (55 mg, 1.44 mmol) was then added, and the reaction was allowed to stir for 3 hours at 60° C. The reaction mixture was then cooled and the solvent evaporated under reduced pressure. The solid was taken up in water and saturated aqueous sodium carbonate was added until pH~7 was attained. The mixture was extracted with ethyl acetate (2×). The combined organics were washed with brine, and dried over magnesium sulfate. This mixture was filtered and the filtrate concentrated under reduced pressure. Recrystallization from ethyl acetate/hexanes afforded the title compound.

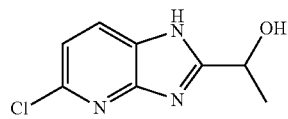

Step 2: 1-(5-Chloro-1H-imidazo[4,5-b]pyridin-2-yl)ethanol

6-Chloropyridine-2,3-diamine (150 mg, 1.05 mmol) and 2-hydroxypropanoic acid (277 mg, 2.61 mmol) were heated to 110° C. for 4 hours. To the cooled mixture was then added 1 N hydrochloric acid, followed by 7N ammonia in methanol to neutralize the acid. The aqueous solution was then evaporated under reduced pressure and the resulting oil was purified via flash chromatography (silica, 0-3% methanol/ethyl acetate) to afford the title compound.

LRMS (APCI) calc'd for (C$_8$H$_9$ClN$_3$O) [M+H]$^+$, 198. found 198.

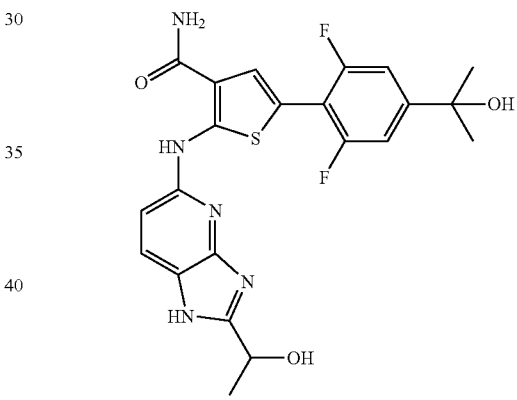

Step 3: 5-[2,6-Difluoro-4-(1-hydroxy-1-methylethyl)phenyl]-2-{[2-(1-hydroxyethyl)-1H-imidazo[4,5-b]pyridin-5-yl]amino}thiophene-3-carboxamide The title compound was prepared as described in Example 1 Step 5 using 2-amino-5-[2,6-difluoro-4-(1-hydroxy-1-methylethyl)phenyl]thiophene-3-carboxamide (150 mg, 0.48 mmol), and 1-(5-chloro-1H-imidazo[4,5-b]pyridin-2-yl)ethanol (95 mg, 0.48 mmol) as starting materials.

LRMS (APCI) calc'd for (C$_{22}$H$_{22}$F$_2$N$_5$O$_3$S) [M+H]$^+$, 474. found 474.

Additional analogues were prepared using procedures similar to those described in the above examples.

TABLE 6

| Example | Structure | Compound Name | Characterization [M + H]+ |
|---|---|---|---|
| 24 | 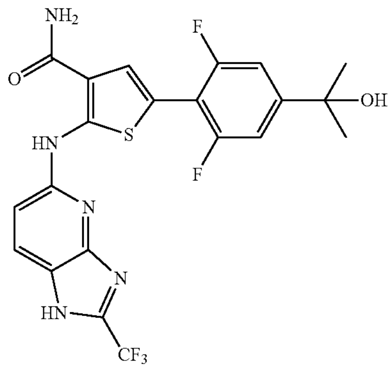 [SMILES: CC(C)(O)c1cc(F)c(-c2cc(C(N)=O)c(Nc3ccc4[nH]c(C(F)(F)F)nc4n3)s2)c(F)c1] | 5-[2,6-difluoro-4-(1-hydroxy-1-methylethyl)phenyl]-2-{[2-(trifluoromethyl)-3H-imidazo[4,5-b]pyridin-5-yl]amino}thiophene-3-carboxamide | Calc'd 498; found 498 |
| 25 | 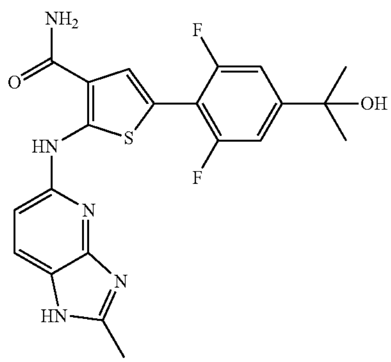 [SMILES: Cc1nc2nc(Nc3sc(-c4c(F)cc(C(C)(C)O)cc4F)cc3C(N)=O)ccc2[nH]1] | 5-[2,6-difluoro-4-(1-hydroxy-1-methylethyl)phenyl]-2-[(2-methyl-1H-imidazo[4,5-b]pyridin-5-yl)amino]thiophene-3-carboxamide | Calc'd 444; found 444 |

Example 26

5-[2,6-Difluoro-4-(1-hydroxy-1-methylethyl)phenyl]-2-{[2-(morpholin-4-ylmethyl)-1H-imidazo[4,5-b]pyridin-5-yl]amino}thiophene-3-carboxamide

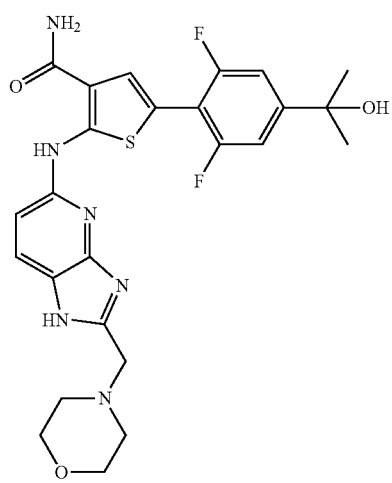 [SMILES: CC(C)(O)c1cc(F)c(-c2cc(C(N)=O)c(Nc3ccc4[nH]c(CN5CCOCC5)nc4n3)s2)c(F)c1]

Step 1: 5-Chloro-2-(morpholin-4-ylmethyl)-1H-imidazo[4,5-b]pyridine

The title compound was prepared as described in Example 23, Step 2 using 6-chloropyridine-2,3-diamine (650 mg, 4.53 mmol) (Example 23, Step 1) and morpholin-4-ylacetic acid (660 mg, 4.53 mmol) as starting materials.

LRMS (APCI) calc'd for ($C_{11}H_{13}ClN_4O$) [M+H], 253. found 253.

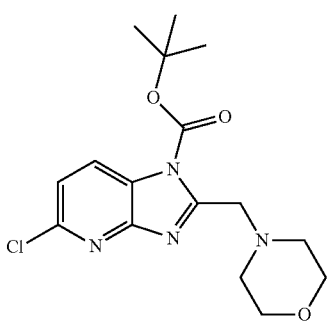 [SMILES: CC(C)(C)OC(=O)n1c(CN2CCOCC2)nc2nc(Cl)ccc21]

Step 2: tert-Butyl 5-chloro-2-(morpholin-4-ylmethyl)-1H-imidazo[4,5-b]pyridine-1-carboxylate A cooled (0° C.) solution of di-tert-butyl dicarbonate (0.92 ml, 3.96 mmol) in DMF (20 ml) was added to a flask containing 5-chloro-2-(morpholin-4-ylmethyl)-1H-imidazo[4,5-b]pyridine (1.0 g, 3.96 mmol) and dimethylaminopyridine (0.48 g, 3.96 mmol). The mixture was allowed to warm to room temperature and then heated to 60° C. overnight. The reaction was then cooled to room temperature, diluted with water, and extracted in ethyl acetate (3×). The combined organic layers were dried over magnesium sulfate, filtered, and concentrated under reduced pressure. Purification via silica gel chromatography (0-3% methanol in ethyl acetate followed by a second column eluting with 50-100% ethyl acetate in hexane) afforded the title compound.

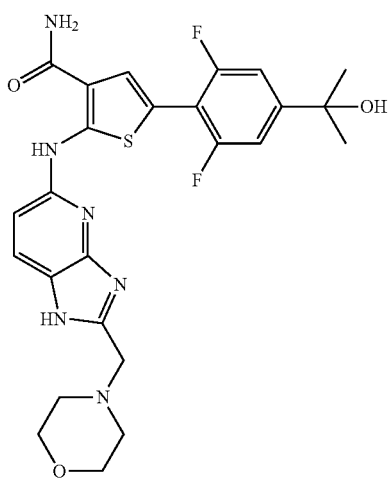 [SMILES: CC(C)(O)c1cc(F)c(-c2cc(C(N)=O)c(Nc3ccc4[nH]c(CN5CCOCC5)nc4n3)s2)c(F)c1]

Step 3: 5-[2,6-Difluoro-4-(1-hydroxy-1-methylethyl)phenyl]-2-{[2-(morpholin-4-ylmethyl)-1H-imidazo[4,5-b]pyridin-5-yl]amino}thiophene-3-carboxamide The title compound was prepared as described in Example 1 Step 5 using 2-amino-5-[2,6-difluoro-4-(1-hydroxy-1-methylethyl)phenyl]thiophene-3-carboxamide (300 mg, 0.96 mmol) and tert-butyl 5-chloro-2-(morpholin-4-ylmethyl)-1H-imidazo[4,5-b]pyridine-1-carboxylate (340 mg, 0.96 mmol) as starting materials.

LRMS (APCI) calc'd for ($C_{25}H_{27}F_2N_6O_3S$) [M+H]$^+$, 529. found 529.

Example 27

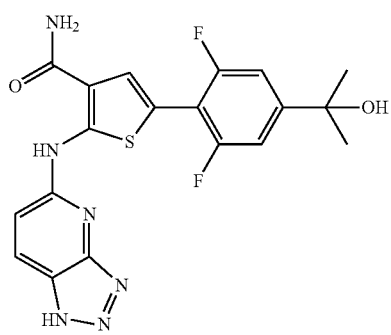 [SMILES: CC(C)(O)c1cc(F)c(-c2cc(C(N)=O)c(Nc3ccc4[nH]nnc4n3)s2)c(F)c1]

5-[2,6-Difluoro-4-(1-hydroxy-1-methylethyl)phenyl]-2-(1H-[1,2,3]triazolo[4,5-b]pyridin-5-ylamino)thiophene-3-carboxamide

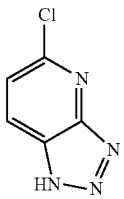

Step 1 5-Chloro-1H-[1,2,3]triazolo[4,5-b]pyridine

6-Chloropyridine-2,3-diamine (Example 23, Step 1) (226 mg, 1.57 mmol) was taken up in warm water (6.3 ml). Sulfuric acid (0.26 ml, 4.72 mmol) was added, and the solution was cooled to −15° C. In a separate flask, sodium nitrite (119 mg, 1.73 mmol) was dissolved in 2 mL cold water. The sodium nitrite solution was added dropwise to the reaction mixture over 15 minutes. The mixture was allowed to stir at −15° C. for 1 hour, then filtered, and the yellow-brown precipitate was collected. The solid was recrystallized from water to yield the title compound as a yellow-brown solid. The filtrate from the separation was neutralized with aqueous sodium bicarbonate and extracted 3× with ethyl acetate. All organic fractions were combined, washed with brine, dried over anhydrous magnesium sulfate, filtered, and concentrated in vacuo to give an additional portion of the title compound as a yellow-brown solid.

LRMS (APCI) calc'd for ($C_5H_4ClN_4$) [M+H]$^+$, 156. found 155.

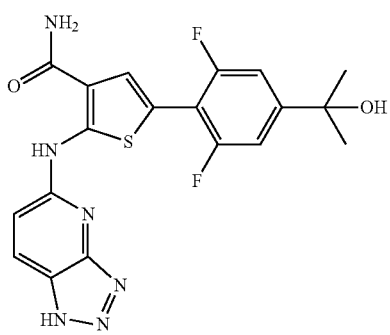 [SMILES: CC(C)(O)c1cc(F)c(-c2cc(C(N)=O)c(Nc3ccc4[nH]nnc4n3)s2)c(F)c1]

Step 2 5-[2,6-Difluoro-4-(1-hydroxy-1-methylethyl)phenyl]-2-(1H-[1,2,3]triazolo[4,5-b]pyridin-5-ylamino)thiophene-3-carboxamide The title compound was prepared as described in Example 1, Step 5 using 2-amino-5-[2,6-difluoro-4-(1-hydroxy-1-methylethyl)phenyl]thiophene-3-carboxamide (70 mg, 0.22 mmol) and 5-chloro-1H-[1,2,3]triazolo[4,5-b]pyridine (35 mg, 0.22 mmol) as starting materials.

LRMS (APCI) calc'd for $(C_{19}H_{17}F_2N_6O_2S)$ [M+H]$^+$, 431. found 431.

Example 28

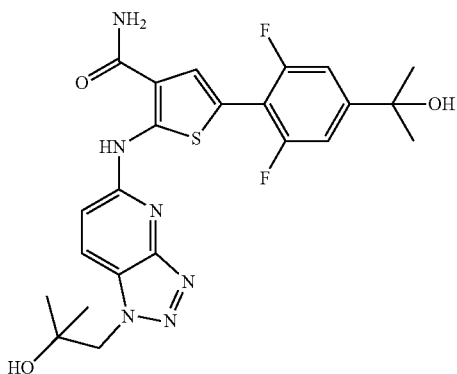 [SMILES: CC(C)(O)Cn1nnc2nc(Nc3sc(-c4c(F)cc(C(C)(C)O)cc4F)cc3C(N)=O)ccc21]

5-[2,6-Difluoro-4-(1-hydroxy-1-methylethyl)phenyl]-2-{[1-(2-hydroxy-2-methylpropyl)-1H-[1,2,3]triazolo[4,5-b]pyridin-5-yl]amino}thiophene-3-carboxamide

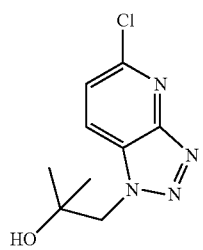

Step 1 1-(5-Chloro-1H-[1,2,3]triazolo[4,5-b]pyridin-1-yl)-2-methylpropan-2-ol

5-Chloro-1H-[1,2,3]triazolo[4,5-b]pyridine (Example 27, Step 1) (285 mg, 1.85 mmol) and 2,2-dimethyloxirane (0.18 mL, 1.94 mmol) were taken-up in DMF (7.4 mL) and potassium tert-butoxide (310 mg, 2.77 mmol) was added. The mixture was heated to 60° C. overnight and then to 85° C. for an additional 36 hours. The mixture was then cooled to room temperature, diluted with saturated aqueous ammonium chloride, and extracted with ethyl acetate (3×). The organic layers were combined, dried over anhydrous magnesium sulfate, filtered, concentrated in vacuo and purified via reverse phase HPLC (10-100% acetonitrile/water+0.05% TFA modifier). Desired fractions were lyophilized to afford the title compound as a yellow solid.

LRMS (APCI) calc'd for $(C_9H_{11}ClN_4O)$ [M+H]$^+$, 227. found 227.

Step 2 5-[2,6-Difluoro-4-(1-hydroxy-1-methylethyl)phenyl]-2-{[1-(2-hydroxy-2-methylpropyl)-1H-[1,2,3]triazolo[4,5-b]pyridin-5-yl]amino}thiophene-3-carboxamide The title compound was prepared as described in Example 1, Step 5 using 2-amino-5-[2,6-difluoro-4-(1-hydroxy-1-methylethyl)phenyl]thiophene-3-carboxamide (23 mg, 0.074 mmol) and 1-(5-chloro-1H-[1,2,3]triazolo[4,5-b]pyridin-1-yl)-2-methylpropan-2-ol (17 mg, 0.074 mmol) as starting materials.

LRMS (APCI) calc'd for ($C_{23}H_{25}F_2N_6O_2S$) [M+H]$^+$, 503. found 503.

Example 29

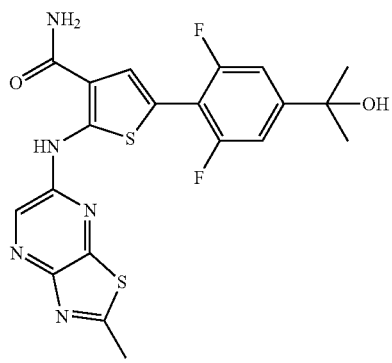 [SMILES: Cc1nc2ncc(Nc3sc(-c4c(F)cc(C(C)(C)O)cc4F)cc3C(N)=O)nc2s1]

5-[2,6-Difluoro-4-(1-hydroxy-1-methylethyl)phenyl]-2-[(2-methyl[1,3]thiazolo[4,5-b]pyrazin-6-yl)amino]thiophene-3-carboxamide Method A: The title compound was prepared according to the general procedure in Example 1 Step 5 using 2-amino-5-[2,6-difluoro-4-(1-hydroxy-1-methylethyl)phenyl]thiophene-3-carboxamide (100 mg, 0.320 mmol) and 6-bromo-2-methyl[1,3]thiazolo[4,5-b]pyrazine (73.7 mg, 0.320 mmol) as the starting materials.

LRMS (APCI) calc'd for ($C_{20}H_{18}F_2N_5O_2S_2$) [M+H]$^+$, 462. found 462.

Example 30

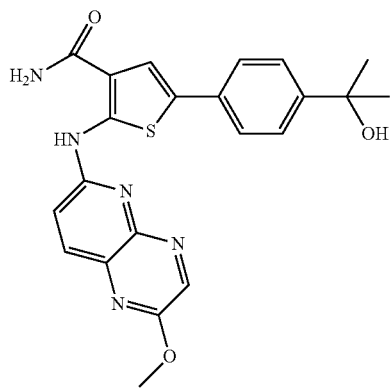 [SMILES: COc1cnc2nc(Nc3sc(-c4ccc(C(C)(C)O)cc4)cc3C(N)=O)ccc2n1]

5-(4-(1-Hydroxy-1-methylethyl)phenyl)-2-[(2-methoxypyrido[2,3-b]pyrazin-6-yl)amino]thiophene-3-carboxamide Method B: To a solution of 6-bromo-2-methoxypyrido[2,3-b]pyrazine (47.8 mg, 0.20 mmol) in t-amyl alcohol (1.0 ml) was added 2-amino-5-(2-fluoro-4-(1-hydroxy-1-methylethyl)phenyl)-3-thiophenecarboxamide (50 mg, 0.18 mmol), potassium carbonate (27.5 mg, 0.20 mmol), X-Phos (43.1 mg, 0.09 mmol) and tris(dibenzylideneacetone)dipalladium (16.6 mg, 0.018 mmol). The vial was capped, evacuated, and backfilled with argon. The reaction mixture was heated in microwave at 120° C. for 20 min, cooled to room temperature, filtered, and filtrate was concentrated in vacuo. Purification by preparative HPLC Reverse phase (C-18), eluting with acetonitrile/water+0.05% TFA followed by lyophilizing the desired fractions afforded the title compound as a TFA salt.

LRMS (APCI) calc'd for ($C_{22}H_{22}N_5O_3S$) [M+H]$^+$: 436. Found: 436.

Example 31

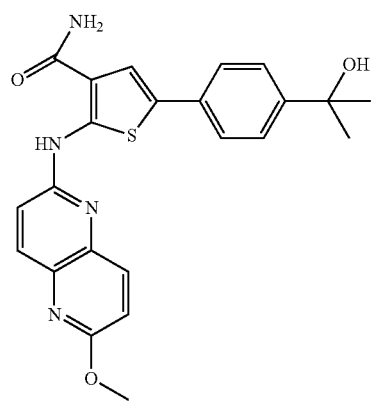 [SMILES: COc1ccc2nc(Nc3sc(-c4ccc(C(C)(C)O)cc4)cc3C(N)=O)ccc2n1]

5-[4-(1-Hydroxy-1-methylethyl)phenyl]-2-[(6-methoxy-1,5-naphthyridin-2-yl)amino]thiophene-3-carboxamide

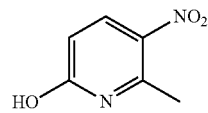

Step 1 6-Methyl-5-nitropyridin-2-ol

A 3-necked roundbottom flask was charged with a solution of 6-methyl-5-nitropyridin-2-amine (20 g, 130.72 mmol) in water (330 ml). To the mixture was added sulfuric acid (23.6 ml). The mixtir was cooled to 0° C. and a solution of sodium nitrite (12.0 g, 173.91 mmol) in water (30 ml) was added dropwise. The resulting solution was allowed to react, with stirring, for 20 at 0° C. and then allowed to warm to room temperature and stirred for an additional one hour. The resulting slurry was filtered and the solids collected to afford the title compound.

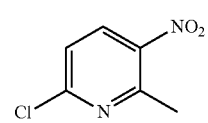

Step 2 6-Chloro-2-methyl-3-nitropyridine

A roundbottom flask was charged with a solution of 6-methyl-5-nitropyridin-2-ol (1.5 g, 9.74 mmol) in phosphorus oxychloride (5 ml). To the mixture was added phosphoryl pentachloride (2.0 g, 9.59 mmol). The resulting solution was allowed to react, with stirring, for three hours while the temperature was maintained at reflux. The mixture was poured into ice water and the solids that formed were collected by filtration to afford the title compound.

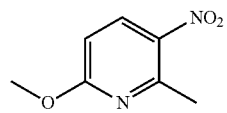

Step 3 6-Methoxy-2-methyl-3-nitropyridine

A roundbottom flask was charged with a solution of 6-chloro-2-methyl-3-nitropyridine (12.0 g, 69.36 mmol) in methanol (100 ml). Sodium methanolate (5.6 g, 103.70 mmol) was added and the resulting solution was stirred at room temperature for 24 hours. The mixture was poured into 100 ml of water and the solids that formed were collected by filtration to afford the title compound.

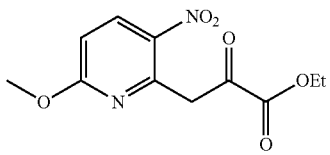 [SMILES: CCOC(=O)C(=O)Cc1nc(OC)ccc1[N+](=O)[O-]]

Step 4 Ethyl 3-(6-methoxy-3-nitropyridin-2-yl)-2-oxopropanoate

A roundbottom flask was charged with ethanol (540 ml) and (7.2 L). To this was added potassium (81.6 g, 2.09 mol) and mixture was stirred until all the potassium dissolved. Diethyl oxalate (306 g, 2.10 mol) was then added. The mixture was stirred for 5 minutes and then 6-methoxy-2-methyl-3-nitropyridine (320.0 g, 1.87 mol) was added. The resulting solution was stirred at room temperature for 36 hours. The slurry was filtered and the collected solids were washed thoroughly with ether and dried under reduced pressure. The solid was then suspended in 30 ml of water acetic acid was added until the pH=4. The solids that formed were collected by filtration to afford the title compound.

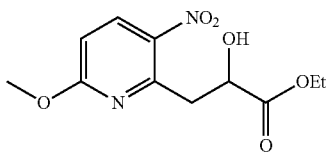 [SMILES: CCOC(=O)C(O)Cc1nc(OC)ccc1[N+](=O)[O-]]

Step 5 Ethyl 3-(6-methoxy-3-nitropyridin-2-yl)-2-oxopropanoate

A roundbottom flask was charged with a solution of ethyl 3-(6-methoxy-3-nitropyridin-2-yl)-2-oxopropanoate (3.73 mmol) in a solution of ethyl acetate (50 mL) and methanol (20 mL). The mixture was cooled to 0° C. and a solution of sodium borohydride (0.5 mg, 0.01 mmol) in methanol (30 ml) was added. Aluminum trichloride (50 mg, 0.37 mmol) was then added and the resulting solution was stirred for 4 hours at 0° C. The reaction mixture was then quenched by the addition of ice water. The resulting solution was diluted with 100 ml of water and extracted two times with 100 ml of ethyl acetate. The combined organic layers were concentrated under reduced pressure to afford the title compound.

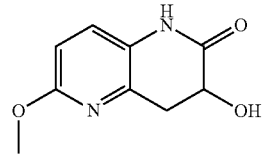

Step 6 3-Hydroxy-6-methoxy-3,4-dihydro-1,5-naphthyridin-2(1H)-one

A roundbottom flask was charged with a solution of ethyl 2-hydroxy-3-(6-methoxy-3-nitropyridin-2-yl)propanoate (37 mmol) in methanol (500 ml). To the mixture was added 10% palladium on carbon (3 g). The solution was shaken under 40 psi of hydrogen for 12 hours. The resulting solution was then allowed to react, with stirring, for 5 hours while the temperature was maintained at room temperature. The mixture was then filtered and the filtrate was diluted with 100 ml of water. Hydrochloric acid was added until the pH=5. The mixture was filtered and the filtrate was adjusted to pH=8 by the addition of sodium carbonate. The solids that formed were collected by filtration to afford the title compound.

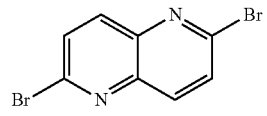

Step 7 2,6-Dibromo-1,5-naphthyridine

A 3-necked roundbottom flask was charged with phosphorus oxybromide (80 ml). To this was added 3-hydroxy-6-methoxy-3,4-dihydro-1,5-naphthyridin-2(1H)-one (5 g, 25.8 mmol) followed by a catalytic amount of N,N-dimethylformamide. The resulting solution was refluxed for 20 minutes. The resulting solution was diluted with 100 ml of ice water. Adjustment of the pH to 7-8 was accomplished by the addition of sodium carbonate. The resulting solution was extracted three times with 200 ml of ethyl acetate. The organic layers were combined and dried over magnesium sulfate, filtered, and concentrated under reduced pressure to afford the title compound.

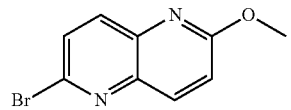

Step 8 2-Bromo-6-methoxy-1,5-naphthyridine

A 3-necked roundbottom flask was charged with a solution of 2,6-dibromo-1,5-naphthyridine (39 g, 135.42 mmol) in methanol (150 ml). The mixture was cooled to 0° C. and a solution of sodium methoxide (8.77 g, 162.41 mmol) in methanol (50 ml) was added dropwise. The resulting solution was allowed to react, with stirring, for three hours at 0° C. The reaction mixture was cooled to <0° C. and a solid precipitated. The mixture was filtered and the filtrated was quenched by the addition of 500 ml of ice water. The solids that formed were collected by filtration and them dissolved in ethyl acetate and dried over magnesium sulfate and filtered. The filtrate was concentrated under reduced pressure. The resulting residue was purified by silica gel chromatography using 1:10 ethyl acetate:petroleum ether as eluant to afford the title compound.

LRMS (APCI) calc'd for $C_{22}H_{20}FN_5O_3S$ [M+H]$^+$: 436. Found: 436.

Example 32

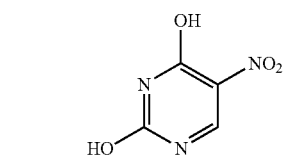

5-[4-(1-Hydroxy-1-methylethyl)phenyl]-2-[(2-methoxypyrido[3,2-d]pyrimidin-6-yl)amino]thiophene-3-carboxamide

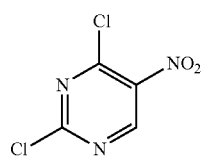

Step 1 5-Nitropyrimidine-2,4-diol

A 3-necked roundbottom flask was charged with sulfuric acid (5400 ml) and the solution was cooled to 0° C. Pyrimidine-2,4-diol (1.0 kg, 8.93 mol) was added in several batches. The resulting solution was allowed to react, with stirring, for 30 minutes. To the above was added nitric acid (1800 ml) dropwise with stirring, while the temperature was maintained at 0° C. The resulting solution was allowed to react, with stirring, for 2 hours. The reaction mixture was then quenched by adding ice water and a precipitate formed. The solid was collected by filtration and dried in an oven under reduced pressure to afford the title compound.

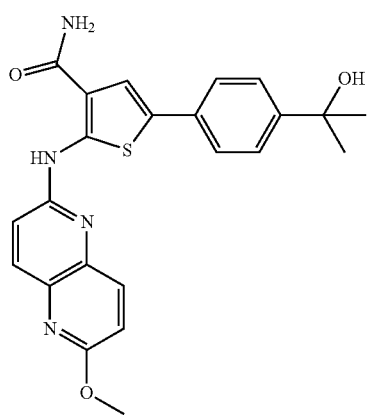 [SMILES: COc1ccc2nc(Nc3sc(-c4ccc(C(C)(C)O)cc4)cc3C(N)=O)ccc2n1]

Step 9 5-[4-(1-Hydroxy-1-methylethyl)phenyl]-2-[(6-methoxy-1,5-naphthyridin-2-yl)amino]thiophene-3-carboxamide The title compound was prepared according to the general procedure in Example 30 (Method B) using 2-bromo-6-methoxy-1,5-naphthyridine (54 mg, 0.22 mmol), 2-amino-5-[4-(1-hydroxy-1-methylethyl)phenyl]thiophene-3-carboxamide (60 mg, 0.20 mmol), potassium carbonate (31 mg, 0.22 mmol), X-Phos (49 mg, 0.10 mmol), and tris(dibenzylideneacetone)dipalladium (16 mg, 0.02 mmol) as the starting materials.

Step 2 2,4-Dichloro-5-nitropyrimidine

A 4-necked roundbottom flask was charged N,N-diethylbenzenamine (1.7 L). To the mixture was added phosphoryl trichloride (3.5 L). followed by 5-nitropyrimidine-2,4-diol (700 g, 4.46 mol) in several batches. The resulting solution was allowed to react, with stirring, for 3 hours while the temperature was maintained at reflux. The mixture was then concentrated under reduced pressure and then quenched by adding ice water. The resulting solution was extracted four times with 5 L of ethyl acetate. The combined organic layers were washed 3 times with 2 L of brine, dried over sodium sulfate, and concentrated under reduced pressure. The resulting residue was purified via silica gel chromatography eluting with 1:50 ethyl acetate/petroleum ether to afford the title compound.

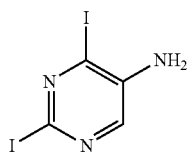

Step 3 2,4-Diiodopyrimidin-5-amine

A 4-necked roundbottom flask was charged with acetone (9.8 L), 2,4-dichloro-5-nitropyrimidine (670 g, 3.45 mol), and sodium iodide dihydrate (1929.6 g, 10.38 mol). Hydrogen iodide (67 ml, 40%) was then added dropwise. The resulting solution was allowed to react, with stirring, for three hours while the temperature was maintained at 20-30° C. Iron (978.6 g, 17.48 mol) was then added followed by the dropwise addition of water (300 ml). The resulting solution was allowed to react, with stirring, for an additional two hours while the temperature was maintained at reflux. The resulting slurry was filtered and the filtrate was concentrated under reduced pressure. The resulting aqueous solution was extracted four times with five liters of ethyl acetate. The combined organic layers were concentrated under reduced pressure. The resulting residue was purified via silica gel chromatography eluting with 1:1 ethyl acetate/petroleum ether to afford the title compound.

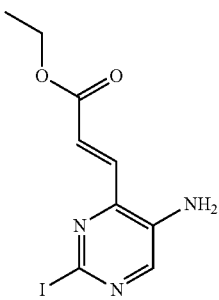

Step 4 (E)-Ethyl 3-(5-amino-2-iodopyrimidin-4-yl) acrylate

A 3-necked roundbottom flask was purged and maintained under an atmosphere of nitrogen. 2,4-Diiodopyrimidin-5-amine (135 g, 389.4 mmol) in dioxane (1400 ml) was added followed by palladium(II) acetate (4.8 g, 19.63 mmol), triethylamine (157 g, 1.55 mol), ethyl acrylate (390 g, 3.90 mol), and tetrabutylammonium chloride (108 g, 389.9 mmol). The resulting solution was allowed to react, with stirring, for 16 hours while the temperature was maintained at 90° C. Upon completion, the mixture was concentrated under reduced pressure. The resulting residue was purified via silica gel chromatography eluting with 1:4 to 1:1 ethyl acetate/ petroleum ether to afford the title compound.

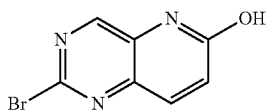

Step 5 2-Bromopyrido[3,2-d]pyrimidin-6-ol

A 3-necked roundbottom flask, was charged with (E)-ethyl 3-(5-amino-2-iodopyrimidin-4-yl)acrylate (120 g, 388 mmol) followed by hydrogen bromide/acetic acid (1500 ml). The resulting solution was allowed to react, with stirring, for 1.5 hours while the temperature was maintained at 40~50° C. Upon completion, the mixture was concentrated under reduced pressure. The resulting residue was dissolved in 500 ml of methanol and the pH was adjusted to 7 by the addition of sodium bicarbonate. The resulting mixture was washed once with a solution of 46 g of NaHSO$_3$ in 200 mL of water. The organic layer was concentrated under reduced pressure. The resulting slurry was filtered and the solids collected to afford the title compound.

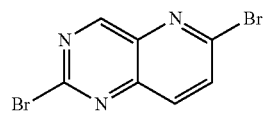

Step 6 2,6-Dibromopyrido[3,2-d]pyrimidine

A roundbottom flask was charged with N,N-dimethylformamide (4.2 L). Phosphorus oxybromide (646.9 g, 2.26 mol, 2.30 equiv) was added followed by dropwise addition of 2-bromopyrido-[3,2-d]-pyrimidin-6-ol (170 g, 752.1 mmol). The resulting solution was allowed to react, with stirring, for 1 minute while the temperature was maintained at 90° C. The reaction mixture was then quenched by the addition of 10 L of water/ice. The resulting solution was extracted once with ethyl acetate. The organic layer was washed with aqueous NaHSO$_4$ and brine, dried over magnesium sulfate, filtered, and concentrated under reduced pressure. The resulting residue was purified via silica gel chromatography eluting with dichloromethane to afford the title compound.

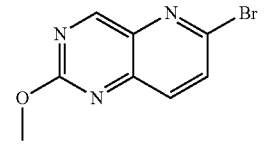

Step 7 6-Bromo-2-methoxypyrido[3,2-d]pyrimidine

A 3-necked roundbottom flask purged and maintained with an inert atmosphere of nitrogen was charged with 2,6-dibromopyrido[3,2-d]pyrimidine (10.7 g, 37.04 mmol). To this was added tetrahydrofuran (500 ml) and methanol (150 ml). A solution of sodium (89 mg, 3.87 mmol, 0.10 equiv) in methnaol (60 ml) was then added dropwise with stirring, while warming to a temperature of 40° C. The resulting solution was allowed to react, with stirring, for 1.5 hours while the temperature was maintained at 40° C. The reaction progress was monitored by TLC. The reaction mixture was then quenched by adding 1.5 L of water. The mixture was concentrated under reduced pressure. The resulting slurry was filtered and the solids collected. The solids were then dissolved in 2 L of ethyl acetate. The resulting mixture was washed once with 500 ml of brine. The organic layer was dried over magnesium sulfate, filtered, and concentrated under reduced pressure. The resulting residue was purified recrystallization from 2:1 tetrahydrofuran:methanol to afford the title compound.

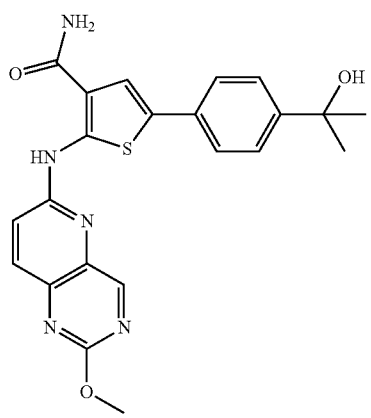 [SMILES: COc1ncc2nc(Nc3sc(-c4ccc(C(C)(C)O)cc4)cc3C(N)=O)ccc2n1]

Step 8 5-[4-(1-Hydroxy-1-methylethyl)phenyl]-2-[(2-methoxypyrido[3,2-d]pyrimidin-6-yl)amino]thiophene-3-carboxamide The title compound was prepared according to the general procedure in Example 30 (Method B) using 6-bromo-2-methoxypyrido[3,2-d]pyrimidine (48 mg, 0.20 mmol), 2-amino-5-[4-(1-hydroxy-1-methylethyl)phenyl]thiophene-3-carboxamide (50 mg, 0.20 mmol), potassium carbonate (31 mg, 0.22 mmol), X-Phos (49 mg, 0.10 mmol), and tris(dibenzylideneacetone)dipalladium (16 mg, 0.02 mmol) as the starting materials.

LRMS (APCI) calc'd for $C_{22}H_{21}N_5O_3S$ [M+H]$^+$: 437. Found: 437.

Additional analogues were prepared using procedures similar to those described in the above examples.

TABLE 7

| Example | Structure | Compound Name | Characterization [M + H]$^+$ | Method |
|---|---|---|---|---|
| 33 | 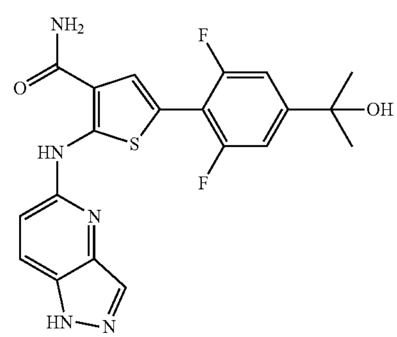 [SMILES: CC(C)(O)c1cc(F)c(-c2cc(C(N)=O)c(Nc3ccc4[nH]ncc4n3)s2)c(F)c1] | 5-[2,6-difluoro-4-(1-hydroxy-1-methylethyl)phenyl]-2-(1H-pyrazolo[4,3-b]pyridin-5-ylamino)thiophene-3-carboxamide | Calc'd 430; found 430 | A |
| 34 | 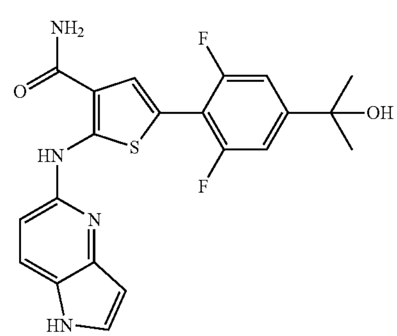 [SMILES: CC(C)(O)c1cc(F)c(-c2cc(C(N)=O)c(Nc3ccc4[nH]ccc4n3)s2)c(F)c1] | 5-[2,6-difluoro-4-(1-hydroxy-1-methylethyl)phenyl]-2-(1H-pyrrolo[3,2-b]pyridin-5-ylamino)thiophene-3-carboxamide | Calc'd 429; found 429 | A |

TABLE 7-continued

| Example | Structure | Compound Name | Characterization [M + H]⁺ | Method |
|---------|-----------|---------------|---------------------------|--------|
| 35 | 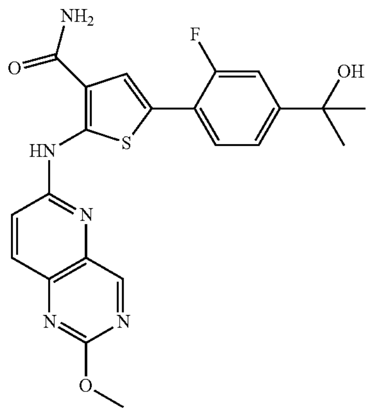 [SMILES: COc1ncc2nc(Nc3sc(-c4ccc(C(C)(C)O)cc4F)cc3C(N)=O)ccc2n1] | 5-(2-fluoro-4-(1-hydroxy-1-methylethyl)phenyl)-2-((2-methoxypyrido[3,2-d]pyrimidin-6-yl)amino)-3-thiophenecarboxamide | Calc'd: 454; Found: 454 | B |
| 36 | 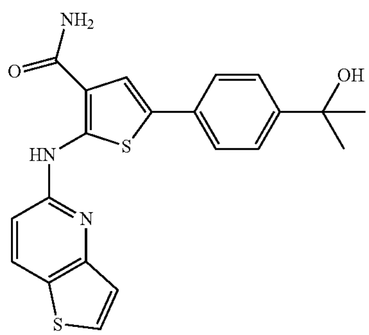 [SMILES: CC(C)(O)c1ccc(-c2cc(C(N)=O)c(Nc3ccc4sccc4n3)s2)cc1] | 5-(4-(1-hydroxy-1-methylethyl)phenyl)-2-(thieno[3,2-b]pyridin-5-ylamino)-3-thiophenecarboxamide | Calc'd: 411, Found: 411 | B |
| 37 | 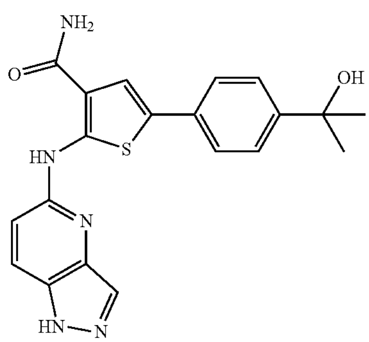 [SMILES: CC(C)(O)c1ccc(-c2cc(C(N)=O)c(Nc3ccc4[nH]ncc4n3)s2)cc1] | 5-(4-(1-hydroxy-1-methylethyl)phenyl)-2-(1H-pyrazolo[4,3-b]pyridin-5-ylamino)-3-thiophenecarboxamide | Calc'd: 394, Found: 394 | B |
| 38 | 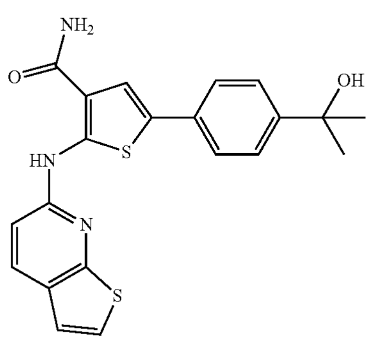 [SMILES: CC(C)(O)c1ccc(-c2cc(C(N)=O)c(Nc3ccc4ccsc4n3)s2)cc1] | 5-(4-(1-hydroxy-1-methylethyl)phenyl)-2-(thieno[2,3-b]pyridin-6-ylamino)-3-thiophenecarboxamide | Calc'd: 411, Found: 411 | B |

TABLE 7-continued

| Example | Structure | Compound Name | Characterization [M + H]+ | Method |
|---|---|---|---|---|
| 39 | 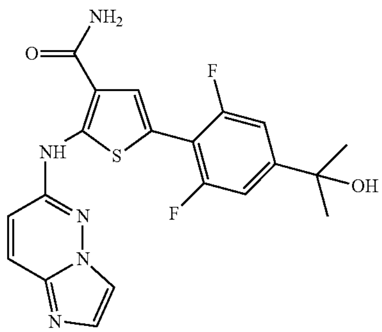 [SMILES: CC(C)(O)c1cc(F)c(-c2cc(C(N)=O)c(Nc3ccc4nccn4n3)s2)c(F)c1] | 5-[2,6-difluoro-4-(1-hydroxy-1-methylethyl)phenyl]-2-(imidazo[1,2-b]pyridazin-6-ylamino)thiophene-3-carboxamide | Calc'd: 430, Found: 430 | A |
| 40 | 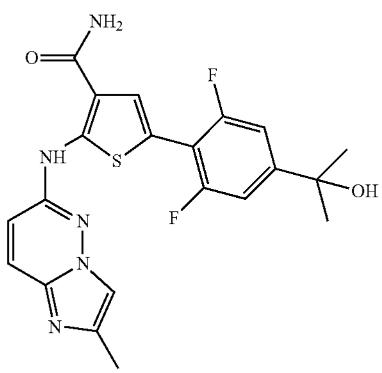 [SMILES: Cc1cn2nc(Nc3sc(-c4c(F)cc(C(C)(C)O)cc4F)cc3C(N)=O)ccc2n1] | 5-[2,6-difluoro-4-(1-hydroxy-1-methylethyl)phenyl]-2-[(2-methylimidazo[1,2-b]pyridazin-6-yl)amino]thiophene-3-carboxamide | Calc'd: 444, Found: 444 | A |
| 41 | 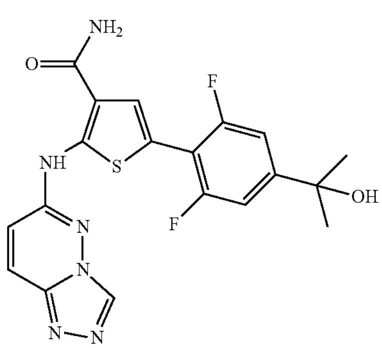 [SMILES: CC(C)(O)c1cc(F)c(-c2cc(C(N)=O)c(Nc3ccc4nncn4n3)s2)c(F)c1] | 5-[2,6-difluoro-4-(1-hydroxy-1-methylethyl)phenyl]-2-([1,2,4]triazolo[4,3-b]pyridazin-6-ylamino)thiophene-3-carboxamide | Calc'd: 431, Found: 431 | A |

TABLE 7-continued

| Example | Structure | Compound Name | Characterization [M + H]+ | Method |
|---|---|---|---|---|
| 42 | 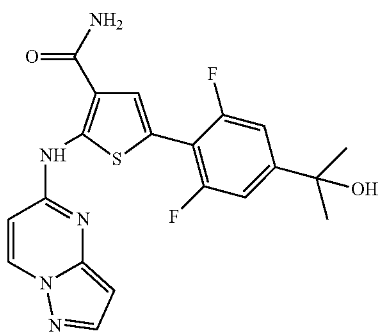 [SMILES: CC(C)(O)c1cc(F)c(-c2cc(C(N)=O)c(Nc3ccn4nccc4n3)s2)c(F)c1] | 5-[2,6-difluoro-1-(1-hydroxy-1-methylethyl)phenyl]-2-(pyrazolo[1,5-a]pyrimidin-5-ylamino)thiophene-3-carboxamide | Calc'd: 430, Found: 430 | A |
| 43[a] | 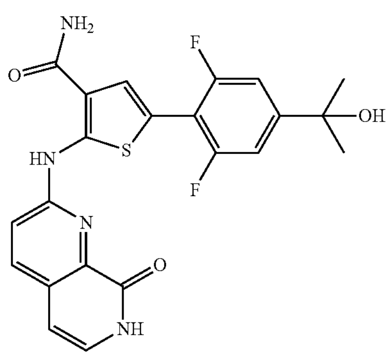 [SMILES: CC(C)(O)c1cc(F)c(-c2cc(C(N)=O)c(Nc3ccc4cc[nH]c(=O)c4n3)s2)c(F)c1] | 5-[2,6-difluoro-4-(1-hydroxy-1-methylethyl)phenyl]-2-[(8-oxo-7,8-dihydro-1,7-naphthyridin-2-yl)amino]thiophene-3-carboxamide | Calc'd: 457, Found: 457 | A |
| 44[a] | 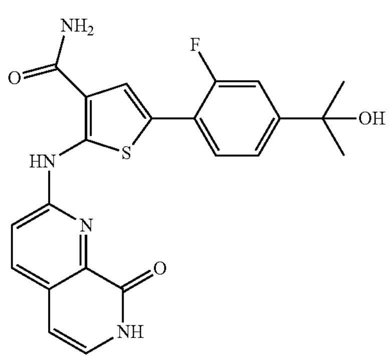 [SMILES: CC(C)(O)c1ccc(-c2cc(C(N)=O)c(Nc3ccc4cc[nH]c(=O)c4n3)s2)c(F)c1] | 5-[2-fluoro-4-(1-hydroxy-1-methylethyl)phenyl]-2-[(8-oxo-7,8-dihydro-1,7-naphthyridin-2-yl)amino]thiophene-3-carboxamide | Calc'd: 439, Found: 439 | A |

Method A: Using procedures described in Example 29.
Method B: Using procedures described in Example 30.

[a] 2-Chloro-1,7-naphthyridin-8(7H)-one was prepared as described in U.S. Pat. No. 2007/0,078,155 A1.

Example 45

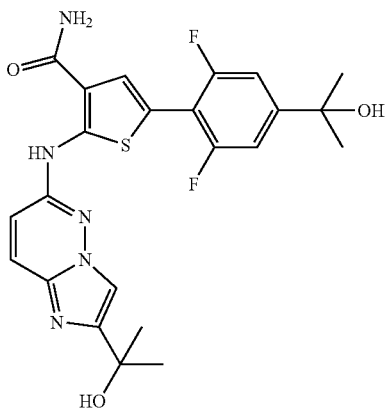 [SMILES: CC(C)(O)c1cc(F)c(-c2cc(C(N)=O)c(Nc3ccc4nc(C(C)(C)O)cn4n3)s2)c(F)c1]

5-[2,6-Difluoro-4-(1-hydroxy-1-methylethyl)phenyl]-2-{[2-(1-hydroxy-1-methylethyl)imidazo[1,2-b]pyridazin-6-yl]amino}thiophene-3-carboxamide

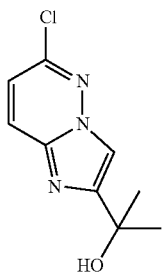

Step 1: 2-(6-Chloroimidazo[1,2-b]pyridazin-2-yl)propan-2-ol

A solution of 2-methyltetrahydrofuran (0.45 mL, 4.43 mmol) in toluene (6.1 mL) was cooled to −20° C. and methylmagnesium chloride (14.8 ml, 44.3 mmol) was added dropwise over five minutes. The solution was stirred for 30 minutes at −20° C., warmed to 0° C. and stirred for 15 minutes, and then re-cooled to −20° C. Ethyl 6-chloroimidazo[1,2-B]pyridazine-2-carboxylate (1 g, 4.43 mmol) was added in portions and the resulting mixture was stirred at 0° C. for 30 minutes then poured into a flask containing 40 ml of cooled (0° C.) 1 N HCl, diluted with ethyl acetate (40 mL) and stirred for ten minutes. The resulting organic layer was washed with saturated aqueous sodium bicarbonate and sodium chloride. The aqueous later was neutralized with saturated aqueous sodium bicarbonate and extracted with ethyl acetate. The organic layers were combined, dried over magnesium sulfate, filtered, concentrated, and purified via silica gel chromatography (0-15% methanol in dichloromethane) to afford the title compound as a white solid.

LRMS (APCI) calc'd for ($C_9H_{11}ClN_3O$) [M+H]$^+$: 212. Found: 212.

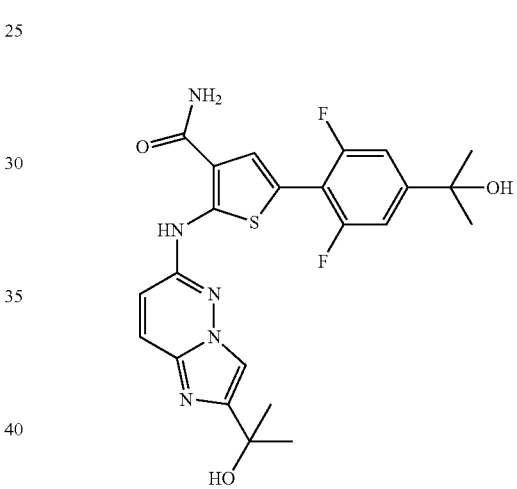

Step 2: 5-[2,6-Difluoro-4-(1-hydroxy-1-methylethyl)phenyl]-2-{[2-(1-hydroxy-1-methylethyl)imidazo[1,2-b]pyridazin-6-yl]amino}thiophene-3-carboxamide The title compound was prepared as described in Example 1, Step 5 using 2-(6-chloroimidazo[1,2-b]pyridazin-2-yl)propan-2-ol (258 mg, 1.22 mmol) and 5-[2,6-difluoro-4-(1-hydroxy-1-methylethyl)phenyl]-2-amino-thiophene-3-carboxamide (90 mg, 0.31 mmol) as starting materials.

Calcd for $C_{23}H_{24}F_2N_5O_3S$ [M+H]$^+$: 488. Found: 488.

Additional analogues were prepared using procedures similar to those described in the above examples.

TABLE 8

| Example # | Structure | Compound Name | Characterization [M + H]+ |
|---|---|---|---|
| 46 | 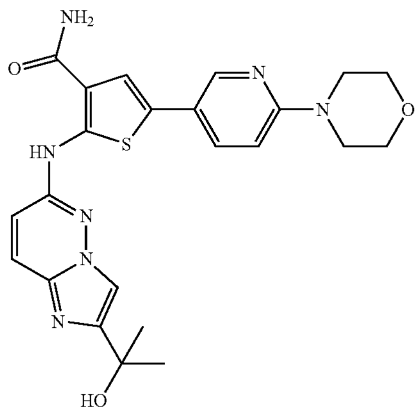 [SMILES: CC(C)(O)c1cn2nc(Nc3sc(-c4ccc(N5CCOCC5)nc4)cc3C(N)=O)ccc2n1] | 2-{[2-(1-hydroxy-1-methylethyl)imidazo[1,2-b]pyridazin-6-yl]amino}-5-(6-morpholin-4-ylpyridin-3-yl)thiophene-3-carboxamide | Calc'd: 480, Found: 480 |
| 47 | 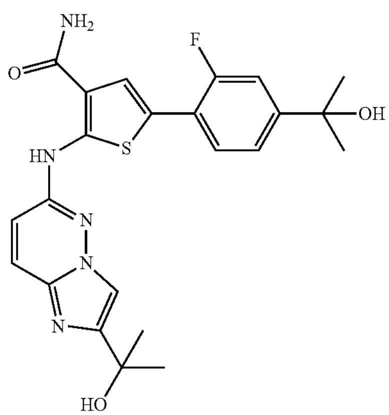 [SMILES: CC(C)(O)c1ccc(-c2cc(C(N)=O)c(Nc3ccc4nc(C(C)(C)O)cn4n3)s2)c(F)c1] | 5-[2-fluoro-4-(1-hydroxy-1-methylethyl)phenyl]-2-{[2-(1-hydroxy-1-methylethyl)imidazo[1,2-b]pyridazin-6-yl]amino}thiophene-3-carboxamide | Calc'd: 470, Found: 470 |

Example 48

5-[2,6-Difluoro-4-(1-hydroxy-1-methylethyl)phenyl]-2-{[2-(2-furyl)imidazo[1,2-b]pyridazin-6-yl]amino}thiophene-3-carboxamide

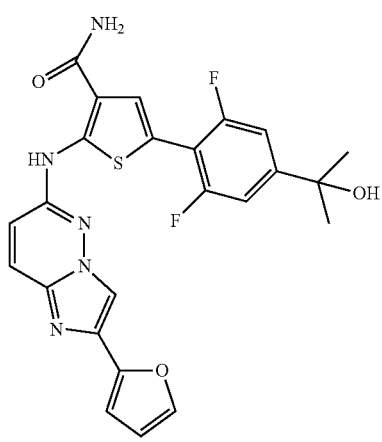 [SMILES: CC(C)(O)c1cc(F)c(-c2cc(C(N)=O)c(Nc3ccc4nc(-c5ccco5)cn4n3)s2)c(F)c1]

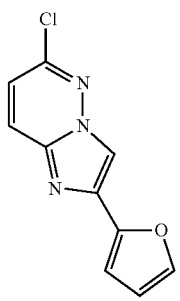 [SMILES: Clc1ccc2nc(-c3ccco3)cn2n1]

Step 1:
6-Chloro-2-(2-furyl)imidazo[1,2-b]pyridazine

A solution of 2-bromo-1-(2-furyl)ethanone (220 mg, 1.16 mmol) and 6-chloropyridazin-3-amine (150 mg, 1.16 mmol) in dioxane (4 ml) was stirred at room temperature for 1.5 hours, and at 65° C. for 16 hours. The reaction mixture was then cooled to ambient temperature, diluted with 3:1 (chloroform:isopropanol) and water. The layers were separated and the organic layer was concentrated under reduced pressure. Silica gel chromatography (0-15% methanol in dichloromethane) afforded the title compound.

LRMS (APCI) calc'd for ($C_{10}H_7ClN_3O$) [M+H]$^+$: 220. found 220.

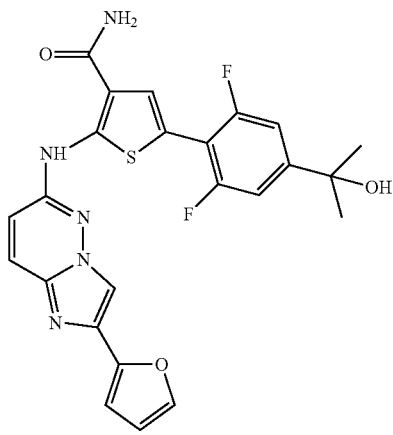 [SMILES: CC(C)(O)c1cc(F)c(-c2cc(C(N)=O)c(Nc3ccc4nc(-c5ccco5)cn4n3)s2)c(F)c1]

Step 2: 5-[2,6-Difluoro-4-(1-hydroxy-1-methylethyl)phenyl]-2-{[2-(2-furyl)imidazo[1,2-b]pyridazin-6-yl]amino}thiophene-3-carboxamide The title compound was prepared as described in Example 1, Step 5 using 6-chloro-2-(2-furyl)imidazo[1,2-b]pyridazine (61.9 mg, 0.282 mmol) and 2-amino-5-[2,6-difluoro-4-(1-hydroxy-1-methylethyl)phenyl]thiophene-3-carboxamide as starting materials.

LRMS (APCI) calcd for ($C_{24}H_{20}F_2N_5O_3S$) [M+H]$^+$: 496. found 496.

Additional analogues were prepared using procedures similar to those described in the above examples.

TABLE 9

| Example # | Structure | Compound Name | Characterization [M + H]$^+$ |
|---|---|---|---|
| 49 | 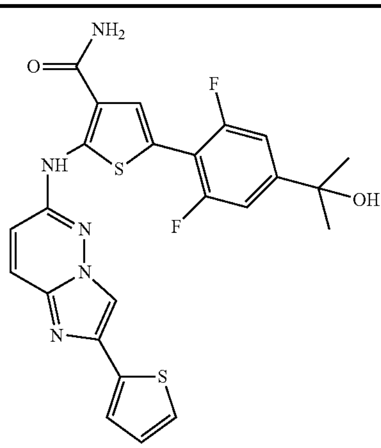 | 5-[2,6-difluoro-4-(1-hydroxy-1-methylethyl)phenyl]-2-{[2-(2-thienyl)imidazo[1,2-b]pyridazin-6-yl]amino}thiophene-3-carboxamide | Calc'd: 512, Found: 512 |
| 50 | 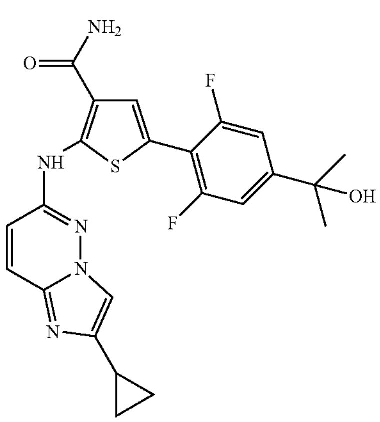 [SMILES: CC(C)(O)c1cc(F)c(-c2cc(C(N)=O)c(Nc3ccc4nc(C5CC5)cn4n3)s2)c(F)c1] | 2-[(2-cyclopropylimidazo[1,2-b]pyridazin-6-yl)amino]-5-[2,6-difluoro-4-(1-hydroxy-1-methylethyl)phenyl]thiophene-3-carboxamide | Calc'd: 470, Found: 470 |

Example 51

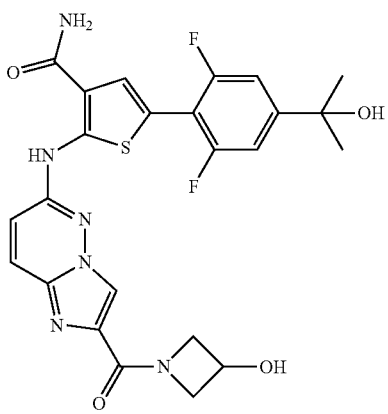 [SMILES: CC(C)(O)c1cc(F)c(-c2cc(C(N)=O)c(Nc3ccc4nc(C(=O)N5CC(O)C5)cn4n3)s2)c(F)c1]

5-[2,6-Difluoro-4-(1-hydroxy-1-methylethyl)phenyl]-2-({2-[(3-hydroxyazetidin-1-yl)carbonyl]imidazo[1,2-b]pyridazin-6-yl}amino)thiophene-3-carboxamide

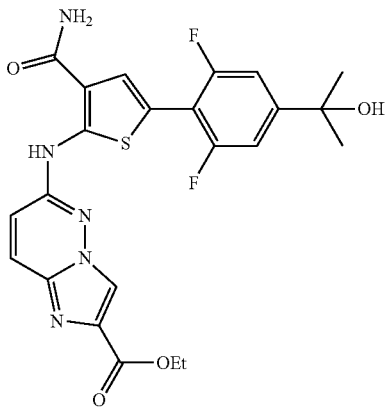 [SMILES: CCOC(=O)c1cn2nc(Nc3sc(-c4c(F)cc(C(C)(C)O)cc4F)cc3C(N)=O)ccc2n1]

Step 1: Ethyl 6-({3-(aminocarbonyl)-5-[2,6-difluoro-4-(1-hydroxy-1-methylethyl)phenyl]-2-thienyl}amino)imidazo[1,2-b]pyridazine-2-carboxylate The title compound was prepared as described in Example 1, Step 5 using ethyl 6-chloroimidazo[1,2-b]pyridazine-2-carboxylate (430 mg, 1.92 mmol) and 2-amino-5-[2,6-difluoro-4-(1-hydroxy-1-methylethyl)phenyl]thiophene-3-carboxamide (400 mg, 1.28 mmol) as starting materials.

LRMS (APCI) calc'd for ($C_{23}H_{22}F_2N_5O_4S$) [M+H]$^+$: 502. Found: 502.

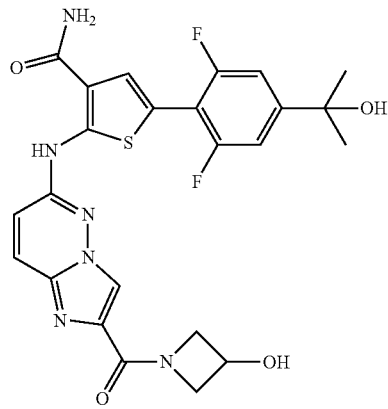 [SMILES: CC(C)(O)c1cc(F)c(-c2cc(C(N)=O)c(Nc3ccc4nc(C(=O)N5CC(O)C5)cn4n3)s2)c(F)c1]

Step 2: 5-[2,6-Difluoro-4-(1-hydroxy-1-methylethyl)phenyl]-2-({2-[(3-hydroxyazetidin-1-yl)carbonyl]imidazo[1,2-b]pyridazin-6-yl}amino)thiophene-3-carboxamide Ethyl 6-({3-(aminocarbonyl)-5-[2,6-difluoro-4-(1-hydroxy-1-methylethyl)phenyl]-2-thienyl}amino)imidazo[1,2-b]pyridazine-2-carboxylate (33 mg, 0.07 mmol) was taken up in tetrahydrofuran and cooled to 0° C. Trimethylaluminum (0.53 ml, 1.06 mmol) was added dropwise, followed by 3-hydroxyazetidine hydrochloride (7 mg, 0.07 mmol). The reaction was stirred at 0° C. for one hour, warmed to room temperature and allowed to react overnight. The reaction was then quenched slowly with methanol, followed by stirring for 10 minutes at room temperature. The resulting mixture was filtered, washing the solids with ethyl acetate and water. The filtrate was collected, the phases were separated and the aqueous layer was extracted with ethyl acetate. The combined organics were concentrated under and purified via flash chromatography (0-15% methanol in dichloromethane) to afford the title compound.

LRMS (APCI) calc'd for ($C_{24}H_{23}F_2N_6O_4S$) [M+H]$^+$: 529. Found: 529.

Example 52

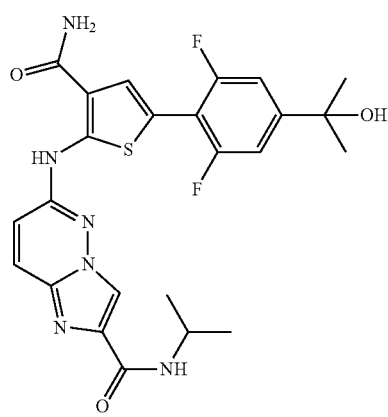 [SMILES: CC(C)NC(=O)c1cn2nc(Nc3sc(-c4c(F)cc(C(C)(C)O)cc4F)cc3C(N)=O)ccc2n1]

6-({3-(Aminocarbonyl)-5-[2,6-difluoro-4-(1-hydroxy-1-methylethyl)phenyl]-2-thienyl}amino)-N-isopropylimidazo[1,2-b]pyridazine-2-carboxamide

Step 1: 6-Chloro-N-isopropylimidazo[1,2-b]pyridazine-2-carboxamide

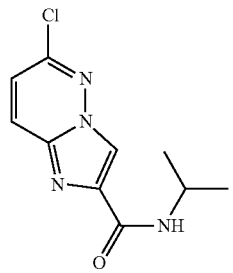 [SMILES: CC(C)NC(=O)c1cn2nc(Cl)ccc2n1]

Ethyl 6-chloroimidazo[1,2-b]pyridazine-2-carboxylate (250 mg, 1.11 mmol) was taken up in tetrahydrofuran and cooled to 0° C. Trimethylaluminum (6.6 mL, 13.3 mmol) was added dropwise followed by the addition of isopropylamine (0.4 mL, 2.2 mmol). The cold bath was removed and the reaction was allowed to proceed overnight at room temperature. The reaction was then quenched slowly with methanol, and stirred for 10 minutes. The resulting mixture was filtered, washing the solids with ethyl acetate and water. The filtrate was collected, the phases were separated and the aqueous layer was extracted with ethyl acetate. The combined organics were concentrated under and purified via flash chromatography (0-15% methanol in dichloromethane) to afford the title compound.

LRMS (APCI) calc'd for $C_{10}H_{12}ClN_4O$ [M+H]$^+$: 239. Found: 239.

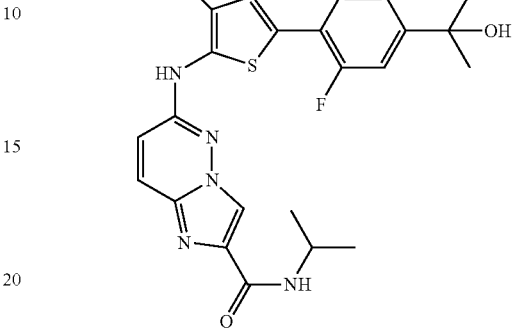

Step 2: 6-({3-(Aminocarbonyl)-5-[2,6-difluoro-4-(1-hydroxy-1-methylethyl)phenyl]-2-thienyl}amino)-N-isopropylimidazo[1,2-b]pyridazine-2-carboxamide The title compound was prepared as described in Example 1, Step 5 using 6-chloro-N-isopropylimidazo[1,2-b]pyridazine-2-carboxamide (149 mg, 0.62 mmol) and 2-amino-5-[2,6-difluoro-4-(1-hydroxy-1-methylethyl)phenyl]thiophene-3-carboxamide (177 mg, 0.57 mmol) as starting materials.

LRMS (APCI) calc'd for ($C_{24}H_{25}F_2N_6O_3S$) [M+H]$^+$: 515. Found: 515.

Additional analogues were prepared using procedures similar to those described in the above examples.

TABLE 10

| Example # | Structure | Compound Name | Characterization [M + H]$^+$ |
|---|---|---|---|
| 53 | 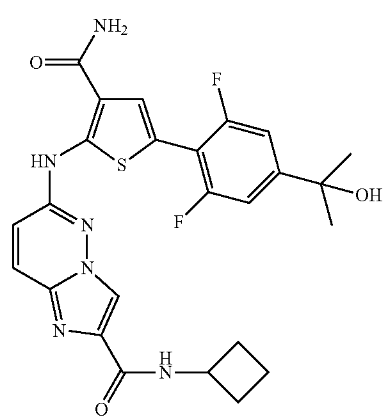 [SMILES: CC(C)(O)c1cc(F)c(-c2cc(C(N)=O)c(Nc3ccc4nc(C(=O)NC5CCC5)cn4n3)s2)c(F)c1] | 6-({3-(aminocarbonyl)-5-[2,6-difluoro-4-(1-hydroxy-1-methylethyl)phenyl]-2-thienyl}amino)-N-cyclobutylimidazo[1,2-b]pyridazine-2-carboxamide | Calc'd: 527, Found: 527 |

TABLE 10-continued

| Example # | Structure | Compound Name | Characterization [M + H]+ |
|---|---|---|---|
| 54 | 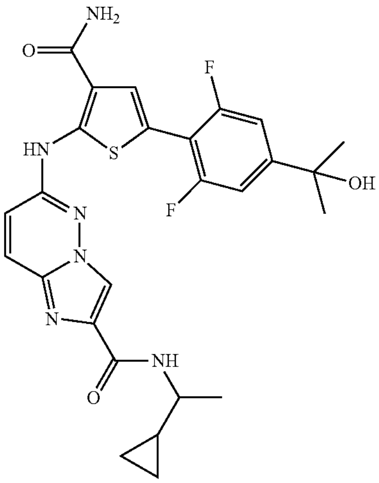 [SMILES: CC(NC(=O)c1cn2nc(Nc3sc(-c4c(F)cc(C(C)(C)O)cc4F)cc3C(N)=O)ccc2n1)C1CC1] | 6-({3-(aminocarbonyl)-5-[2,6-difluoro-4-(1-hydroxy-1-methylethyl)phenyl]-2-thienyl}amino)-N-(1-cyclopropylethyl)imidazo[1,2-b]pyridazine-2-carboxamide | Calc'd: 541, Found: 541 |
| 55 | 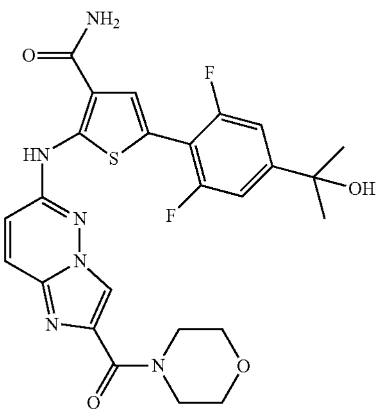 [SMILES: CC(C)(O)c1cc(F)c(-c2cc(C(N)=O)c(Nc3ccc4nc(C(=O)N5CCOCC5)cn4n3)s2)c(F)c1] | 5-[2,6-difluoro-4-(1-hydroxy-1-methylethyl)phenyl]-2-{[2-(morpholin-4-ylcarbonyl)imidazo[1,2-b]pyridazin-6-yl]amino}thiophene-3-carboxamide | Calc'd: 543, Found: 543 |

Example 56

5-[2,6-Difluoro-4-(1-hydroxy-1-methylethyl)phenyl]-2-([1,2,5]oxadiazolo[3,4-b]pyridin-5-ylamino)thiophene-3-carboxamide

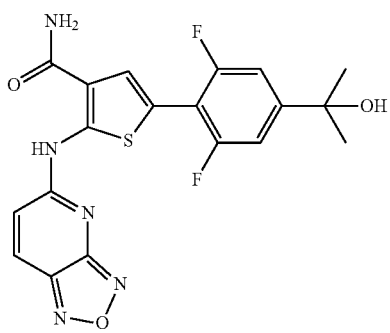 [SMILES: CC(C)(O)c1cc(F)c(-c2cc(C(N)=O)c(Nc3ccc4nonc4n3)s2)c(F)c1]

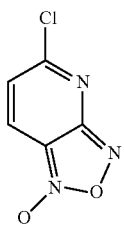

Step 1 5-Chloro[1,2,5]oxadiazolo[3,4-b]pyridine 1-oxide

6-Chloro-3-nitropyridin-2-amine (1.25 g, 7.06 mmol) and iodobenzene diacetate (5.80 g, 17.65 mmol) were taken-up in acetone (70.6 ml) and stirred at 80° C. for 6 hours. The reaction was then concentrated directly, and the resulting crude product was purified by silica gel chromatography (0-100% ethyl acetate/hexanes) to afford 5-chloro[1,2,5]oxadiazolo[3,4-b]pyridine 1-oxide. LRMS (APCI) calc'd for ($C_5H_3ClN_3O_2$) [M+H]$^+$, 172. found 172.

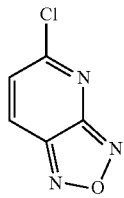

Step 2 5-Chloro[1,2,5]oxadiazolo[3,4-b]pyridine

In a dry flask, 5-chloro[1,2,5]oxadiazolo[3,4-b]pyridine 1-oxide (200 mg, 1.166 mmol) and triphenylphosphine (459 mg, 1.749 mmol) were taken-up in dichloromethane (11.7 ml) under argon. The mixture was stirred at 35° C. for 24 hours. The reaction was quenched with 1.0 M aqueous sodium hydroxide and extracted three times with ethyl acetate. All organic fractions were combined, dried over anhydrous magnesium sulfate, and concentrated. The crude product was purified by reverse-phase HPLC (20-100% acetonitrile/water with 0.05% trifluoroacetic acid), and then the appropriate fractions were neutralized with aqueous sodium bicarbonate and washed twice with ethyl acetate. All organic fractions were combined, dried over anhydrous magnesium sulfate, and concentrated to afford 5-chloro[1,2,5]oxadiazolo[3,4-b]pyridine. LRMS (APCI) calc'd for ($C_5H_3ClN_2O$) [M+H]$^+$, 156. found 156.

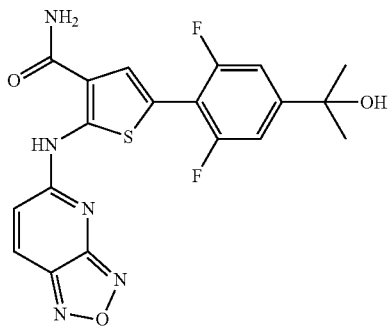 [SMILES: CC(C)(O)c1cc(F)c(-c2cc(C(N)=O)c(Nc3ccc4nonc4n3)s2)c(F)c1]

Step 3 5-[2,6-Difluoro-4-(1-hydroxy-1-methylethyl)phenyl]-2-([1,2,5]oxadiazolo[3,4-b]pyridin-5-ylamino)thiophene-3-carboxamide The title compound was prepared as described in Example 1, Step 5 using 2-amino-5-[2,6-difluoro-4-(1-hydroxy-1-methylethyl)phenyl]thiophene-3-carboxamide (125 mg, 0.40 mmol) and 5-chloro[1,2,5]oxadiazolo[3,4-b]pyridine (62.2 mg, 0.40 mmol) as starting materials. LRMS (APCI) calc'd for ($C_{19}H_{16}F_2N_5O_3S$) [M+H]$^+$, 432. found 432.

Example 57

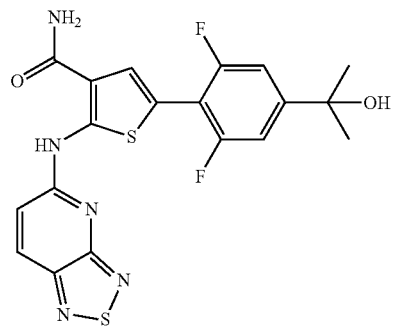

5-[2,6-Difluoro-4-(1-hydroxy-1-methylethyl)phenyl]-2-([1,2,5]thiadiazolo[3,4-b]pyridin-5-ylamino)thiophene-3-carboxamide

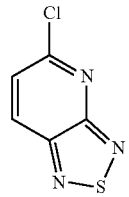

Step 1 5-Chloro[1,2,5]thiadiazolo[3,4-b]pyridine

6-Chloropyridine-2,3-diamine (Example 23, Step 1) (150 mg, 1.045 mmol) was taken-up in dioxane (21.0 ml) under argon at room temperature. Thionyl chloride (686 μl, 9.40 mmol) was added dropwise over 15 minutes. The mixture was then stirred at 75° C. for 24 hours. The reaction was quenched with water and extracted three times with ethyl acetate. All organic layers were combined, dried over anhydrous magnesium sulfate, and concentrated. The resulting crude product was purified by silica gel chromatography (0-65% ethyl acetate/hexanes) to afford 5-chloro[1,2,5]thiadiazolo[3,4-b]pyridine. LRMS (APCI) calc'd for ($C_5H_3ClN_3S$) [M+H]$^+$, 172. found 172.

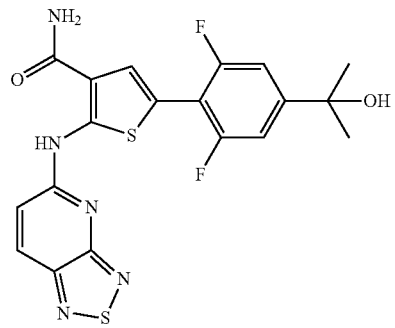 [SMILES: CC(C)(O)c1cc(F)c(-c2cc(C(N)=O)c(Nc3ccc4nsnc4n3)s2)c(F)c1]

Step 2 5-[2,6-Difluoro-4-(1-hydroxy-1-methylethyl) phenyl]-2-([1,2,5]thiadiazolo[3,4-b]pyridin-5-ylamino)thiophene-3-carboxamide The title compound was prepared as described in Example 1, Step 5 using 2-amino-5-[2,6-difluoro-4-(1-hydroxy-1-methylethyl)phenyl]thiophene-3-carboxamide (150 mg, 0.48 mmol) and 5-chloro[1,2,5]thiadiazolo[3,4-b]pyridine (82 mg, 0.48 mmol) as starting materials. LRMS (APCI) calc'd for $(C_{19}H_{16}F_2N_5O_2S_2)$ $[M+H]^+$, 448. found 448.

Pharmaceutical Composition

As a specific embodiment of this invention, 100 mg of 5-[2,6-Difluoro-4-(1-hydroxy-1-methylethyl)phenyl]-2-{[6-(2-hydroxyethyl)-5-oxo-6,7-dihydro-5H-pyrrolo[3,4-b]pyridin-2-yl]amino}thiophene-3-carboxamide is formulated with sufficient finely divided lactose to provide a total amount of 580 to 590 mg to fill a size 0, hard-gelatin capsule.

BIOLOGICAL ASSAYS

JAK1 Enzyme Assay

For the JAK1 enzyme assay, reactions (50 uL) contained 5×IVGN buffer (50 mM Hepes, pH 7.5, 10 mM $MgCl_2$, 0.01% Brij-35, 1 mM EGTA, 0.1 mg/ml BSA), 2 mM DTT, 2.0 µM peptide substrate, 25 µM MgATP, 400 pM JAK1 enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle-1000 us, flash energy level-103) Peptide substrate is amino hexanoyl biotin-EQEDEPEGDY-FEWLE-$NH_2$ (SEQ. ID NO.: 1); in DMSO.

JAK2 Kinase Activity Inhibition Assay and Determination of $IC_{50}$

The kinase activity was measured using a modified version of the homogeneous time-resolved tyrosine kinase assay described in Park et al. *Anal. Biochem.* 269, 94-104 (1999).

The procedure for determining the potency of a compound to inhibit JAK2 kinase comprises the following steps:
1. prepare 3-fold serial diluted compound/inhibitor solutions in 100% (DMSO) at 20× of the final desired concentrations in a 96 well plate;
2. prepare a master reaction mix containing 6.67 mM $MgCl_2$, 133.3 mM NaCl, 66.7 mM Tris-HCl (pH 7.4), 0.13 mg/ml BSA, 2.67 mM dithiothreitol, 0.27 recombinant JAK2 and 666.7 nM biotinylated synthetic peptide substrate (biotin-ahx-EQEDEPEGDYFEWLE-$CONH_2$) (SEQ. ID NO.: 1);
3. in a black assay plate, add 2.5 µl compound/inhibitor (or DMSO) and 37.5 µl master reaction mix per well; initiate the kinase reaction by adding 10 µl of 75 µM MgATP per well, allow the reactions to proceed for 80 minutes at room temperate; (the final conditions for the reactions are: 50 nM JAK2 JH1 domain (Upstate), 2.0 µM substrate, 15 µM MgATP, 5 mM $MgCl_2$, 100 mM NaCl, 2 mM DTT, 0.1 mg/ml BSA, 50 mM Tris (pH 7.4) and 5% DMA));
4. stop the kinase reaction with 50 µl of Stop/Detection buffer containing 10 mM EDTA, 25 mM HEPES, 0.1% TRITON X-100, 0.126 µg/ml Eu-chelate labeled anti-phosphotyrosine antibody PY20 (cat. # AD0067, PerkinElmer) and 45 µg/ml Streptavidin-allophycocyanin conjugate (cat. #PJ25S, Prozyme); and
5. read HTRF signals on a Victor reader (PerkinElmer) in HTRF mode after 60 minutes.

$IC_{50}$ was obtained by fitting the observed relationship between compound/inhibitor concentration and HTRF signal with a 4-parameter logistic equation.

Compounds of the instant invention described in Examples 1-55 are potent inhibitors of recombinant purified JAK2 kinase activity with an $IC_{50}$ of approximately 0.8 nM-1.5 µM. Compounds of the instant invention described in Examples 1-21 are potent inhibitors of recombinant purified JAK2 kinase activity with an $IC_{50}$ of approximately 0.8 nM-95 nM. Compounds of the instant invention described in Examples 23-27 are potent inhibitors of recombinant purified JAK2 kinase activity with an $IC_{50}$ of approximately 7 nM-14 nM.

JAK3 Enzyme Assay

For the JAK3 enzyme assay, reactions (50 uL) contained 5×IVGN buffer (50 mM Hepes, pH 7.5, 10 mM $MgCl_2$, 0.01% Brij-35, 1 mM EGTA, 0.1 mg/ml BSA), 2 mM DTT, 2.0 µM peptide substrate, 25 µM MgATP, 400 µM JAK3 enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103) Peptide substrate is amino hexanoyl biotin-EQEDEPEGDY-FEWLE-NH2 (SEQ. ID NO.: 1); in DMSO.

TYK2 Enzyme Assay

For the TYK2 enzyme assay, reactions (50 uL) contained 5×IVGN buffer (50 mM Hepes, pH 7.5, 10 mM $MgCl_2$, 0.01% Brij-35, 1 mM EGTA, 0.1 mg/ml BSA), 2 mM DTT, 2.0 µM peptide substrate, 15 µM MgATP, 125 pM enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103) Peptide substrate is amino hexanoyl biotin-EQEDEPEGDY-FEWLE-NH2 (SEQ. ID NO.: 1); in DMSO.

Assay For JAK Family Protein Kinase Activity

Materials: Streptavidin•allophycocyanin conjugate (SA•APC) and Europium•cryptate (Eu•K) were from Packard Instrument Company. Eu•K conjugated pY20 was produced as described in Cummings, R. T.; McGovern, H. M.; Zheng, S.; Park, Y. W. and Hermes, J. D. Use Of A Phosphotyrosine-Antibody Pair As A General Detection Method In Homogeneous Time Resolved Fluorescence-Application To Human Immunodeficiency Viral Protease. *Analytical Biochemistry* 1999, 33, 79-93. Homogenous time resolved fluorescence (HTRF) measurements were made using the Discovery instrument from Packard. T-stim Culture Supplement was from Collaborative Biomedical Research. Recombinant mouse IL2 was from Pharmingen or R & D.

JAK family kinase expression: JAK3, TYK2 and JAK2 kinase domains with N-terminal "Flag" affinity tags were expressed in Sf9 cells using standard baculovirus methods. The human JAK3 gene and the human TYK2 gene can be purchased from Update (now part of Millpore Corporation). Human JAK2 kinase domain was cloned from a MOLT4 cDNA library (Clonetech).

Assay for JAK family protein kinase activity: Tyrosine kinase activity was measured by detection of the tyrosine phosphorylated peptide amino hexanoyl biotin-EQEDEPEGDY-FEWLE-NH$_2$ (SEQ. ID NO.: 1); (S, hereafter) detected by time-resolved fluorescence using a europium labeled antibody to phosphotyrosine (pY20). The JAK3(JH1) catalyzed phosphorylation reactions were carried out in a 30 uL total reaction volume. The compound was run at 5% DMSO and preincubated with enzyme buffer (EB). The EB comprised Invitrogen 5× kinase buffer (50 mM Hepes, pH 7.5, 10 mM MgCl$_2$, 0.01% Brij-35, 1 mM EGTA, 0.1 mg/ml BSA), 2 mM (final) DTT, 2 µM (final) S, and 250 pM (final) JAK3 enzyme. The assay was run at ATP $K_m$ (5 µM final) for 40 to 80 minutes. Reactions were run at ambient temperature and quenched with an equal volume of quench buffer (QB) (10 mM EDTA, 25 mM HEPES, 0.1% TRITON X-100) containing 50 µg/mL SA•APC conjugate and 0.75 nM Eu•K conjugated pY20. This mixture was incubated at ambient temperature for at least 60 minutes and read on an optimized fluorescent reader at Ex=320 nm and $Em_1$=665 nm (SA-APC) and $Em_2$=615 nM (Eu). The data was analyzed by using a standard 4P fit on the ratio of the Em results: $(EM_1 \div EM_2)$ *10,000.

JAK2 384-well HEL irf1-bla AlphaScreen™ SureFire™ p-STAT5 Assay:

Principle: When JAK2 is activated and dimerized, it phosphorylates STAT5 which translocates to the nucleus and actives the transcription of target genes. AlphaScreen™ SureFire™ p-STAT5 assay (Perkin Elmer and TGR Biosciences) uses both biotinylated anti-phospho-STAT5 antibody, which is captured by Streptavidin-coated Donor beads, and anti-total STAT5 antibody, which is captured by Protein A conjugated Acceptor beads. The irf1-bla HEL CellSensor™ cell line was created by transducing parental HEL 92.1.7 cells (ATCC) with the pLenti-bsd/irf1-bla CellSensor™ vector. When both antibodies bind to phospho-STAT5 proteins released from HEL irf1-bla cells, the Donor and Acceptor beads are brought into the close proximity (<=200 nm) and a cascade of chemical reactions is initiated to produce a greatly amplified signal. Upon laser excitation, a photosensitizer in the donor bead converts ambient oxygen to a more excited singlet state. The singlet state oxygen molecules diffuse across to react with a chemiluminescer in the acceptor bead that further activates fluorophores contained within the same bead. The fluorophores subsequently emit light at 520-620 nm. The emitted light intensity is directly proportional to the amount of phospho-STAT5 proteins released from HEL irf1-bla cells.

Growth Medium: RPMI Medium 1640 (Invitrogen) with 10% dialyzed FBS (Invitrogen), 1 µg/ml blasticidin, 0.1 mM NEAA, 1 mM sodium pyruvate and 1% Pen-Strep.

Method: On day 1, split HEL irf1-bla cells at density of 500,000 cells/ml. Incubate cells in a tissue culture flask at 37° C., 5% CO$_2$ overnight. On day 2, harvest cells and wash the once with HBSS (Invitrogen) containing 0.5% dialyzed FBS. Next, seed cells at a density of 100,000 cells/well in 8 ul of HBSS w/0.5% dialyzed FBS in 384-well microtiter plates. Temporarily put these cell plates in a 37° C., 5% CO$_2$ incubator. To prepare a compound plate, prepare serially diluted compounds in DMSO at a 500× stock concentration. Transfer 2 uL of the serially diluted compounds from the compound plate to an intermediate dilution plate containing 198 uL of HBSS w/0.5% dialyzed FBS. Next, transfer 2 uL of intermediately diluted compounds to each well of the cell plate to get 1:500 final dilution of each test compound and controls. Incubate the cell plates at 37° C., 5% CO$_2$ for 1 hr. Add 2.5 ul/well of 5× lysis buffer from the kit to cell plates. Gently agitate the plates for 5-10 min.

Make detection reagent mixture A by adding together 800 uL reaction buffer, 20 uL acceptor beads, and 200 uL activation buffer. Add 15 uL/well of detection mixture A to the cell plates and gently agitate the plates for 1-2 mM. Seal the plates with an adhesive cover and incubate at room temperature for 2 hr, avoiding exposure to light. Make detection mixture B by adding together 400 uL dilution buffer and 20 uL donor beads. Add 6 uL/well of mixture B to the cell plates and gently agitate the plates for 1-2 min. Seal the plates with an adhesive cover and incubate at room temperature for 2 hr, avoiding exposure to light. Read the plates on an AlphaScreen-capable plate reader.

Compounds of the instant invention described in Examples 1-55 are potent inhibitors of pSTAT5 in the HEL irf1-bla AlphaScreen™ SureFire™ p-STATS Assay activity with an inflexion point (IP) of <20 µM.

Cellular proliferation assays: CTLL-2 cells (ATCC) were maintained in 6% T-stim Culture Supplement (source of IL2) in RPMI-1640 supplemented with 10% fetal bovine serum, 1 mM sodium pyruvate, 50 µM β-mercaptoethanol, 1.4 mM L-glutamine, 10 mM HEPES, 1 mg/ml dextrose, 0.04 mM essential amino acids, 0.02 mM nonessential amino acids, penicillin and streptomycin (H10). The day before use in the proliferation assay, cells were washed and resuspended in 0.2% Tstim at a cell concentration of 5×10$^5$/ml. The next day, cells were washed and plated at 0.2-1×10$^5$ cells/well in a 96 well tissue culture plate (CoStar). 0.05 ng/ml mouse recombinant IL2 (Pharmingen), with or without a test compound, or 20 ng/ml PMA (Sigma) and 1 µCi/well [$^3$H]-thymidine were added. After overnight culture, cells were harvested with a glass fiber Filtermat (Wallac) and a Tomtek cell harvester. Tritium incorporation was measured by liquid scintillation counting on a Topcount scintillation counter (Packard).

Compounds of the instant invention described in Examples 1-55 are potent inhibitors of recombinant purified JAK3 kinase activity with an IC$_{50}$ of approximately 70 nM->3 µM.

In Vitro PDK1 Kinase Assay

Activated recombinant full-length mT(Glu-Glu-Phe) tagged human PDK1 is used to determine whether the compounds of the instant invention modulate the enzymatic activity of this kinase.

The cDNA, encoding full-length PDK1, is subcloned into a baculovirus expression vector pBlueBac4.5 (Invitrogen), containing an in frame middle T tag (MEYMPME) at its N-terminus. Soluble activated recombinant full-length mT(Glu-Glu-Phe) tagged human PDK1 is expressed in a baculovirus-infected SD insect cells (Kemp Biotechnologies), according to the protocol recommended by the manufacturer. Immunoaffinity purification of the PDK1 kinase from the insect cell lysate is performed using a middle Tag antibody bound to Protein G-EE column. Upon elution using 50 mM Tris pH 7.4, 1 mM EDTA, 1 mM EGTA, 0.5 mM Na$_3$VO$_4$, 1 mM DTT, 50 mM NaF, Na Pyrophospate, Na-β-glycerophosphate, 10% glycerol, Complete, 1 µM microcystein, and 50 µg/ml EYMPME peptide, fractions containing PDK1 protein are pooled together, based on SDS-PAGE and western blot analyses, and then analyzed for protein concentration using BCA Protein Assay (Pierce) with BSA as standard. The final product was aliqouted and flash frozen in liquid nitrogen before being stored at −80° C. Resulting PDK1 protein has MW of 64 kDa, is phosphorylated 'by default' and purifies as an activated kinase from insect cells.

The procedure for determining the potency of a compound to inhibit PDK1 kinase comprises the following steps:

1. Prepare 3-fold serial diluted compound solutions in 100% dimethyl sulfoxide (DMSO) at 20× of the desired final concentrations in a 384-well plate.
2. Prepare a master reaction mix containing 62.5 mM HEPES (pH 7.5), 12.5 mM MgCl2, 0.013% Brij-35, 1.25 mM EGTA, 2.5 mM dithiothreitol, 1.25 nM recombinant PDK1 and 375 nM biotinylated synthetic peptide substrate (Biotin-GGDGATMKTFCGGTPSDGDP-DGGEFTEF-COOH) (SEQ. ID NO.: 2).

3. In a black assay plate, add 2.5 μl of compound solution (or DMSO) and 22.5 μl of master reaction mix per well. Pre-incubate for 10 min. Initiate the kinase reaction by adding 6 μl of 0.25 mM MgATP per well. Allow the reactions to proceed for 25 min at room temperature. The final conditions for the reaction are 1 nM PDK1, 300 nM peptide substrate, 5 μM MgATP, 10 mM MgCl$_2$, 2 mM DTT, 50 mM HEPES (pH 7.5), 0.01% Brij-35, 1 mM EGTA and 5% DMSO.
4. Stop the kinase reaction with 30 μl of Stop/Detection buffer containing 10 mM EDTA, 1× Lance Detection Buffer (cat. # CR97-100, PerkinElmer), 1% Super-Blocking in TBS (cat. # 37535, Pierce), 5 nM phospho-Akt(T308) monoclonal antibody (cat. # 4056, Cell Signaling Technologies), 5 nM Lance labeled Eu-Anti-rabbit IgG (cat. # AD0083, PerkinElmer), and 100 nM Streptavidin-allophycocyanin conjugate (cat. # PJ25S, Prozyme).
5. Read HTRF signals on an Envision reader (PerkinElmer) in HTRF mode after 60 min.
6. I050 is determined by fitting the observed relationship between compound concentration and HTRF signal with a 4-parameter logistic equation.

Compounds of the instant invention were tested in the above assay and found to have an IC$_{50}$ of approximately 670 nM-2.5 μM.

While a number of embodiments of this invention have been described, it is apparent that the basic examples may be altered to provide other embodiments, encompassed by the present invention. Therefore, it will be appreciated that the scope of this invention is to be defined by the appended claims rather than by the specific embodiments, which have been represented by way of example.

What is claimed is:
1. A compound of formula I:

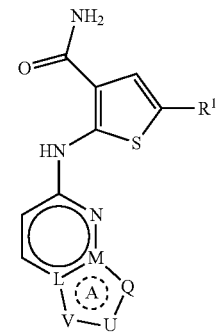

wherein
L is C;
M is C;
Q is CHR$^3$;
U is NR$^5$;
V is C=O;
the dashed circle which represents optional aromatic bonds is absent;
R$^1$ is aryl or heteroaryl, wherein said aryl and heteroaryl groups are optionally substituted on either the carbon or the heteroatom with one to three substituents independently selected from the group consisting of halo, hydroxyl, cyano, C$_{1-6}$ alkyl and heterocyclyl, wherein

---

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Completely synthetic
<220> FEATURE:
<221> NAME/KEY: AMIDATION
<222> LOCATION: (15)...(15)
<223> OTHER INFORMATION: Glutamic acid amide

<400> SEQUENCE: 1

Glu Gln Glu Asp Glu Pro Glu Gly Asp Tyr Phe Glu Trp Leu Glu
1               5                   10                  15

<210> SEQ ID NO 2
<211> LENGTH: 28
<212> TYPE: PRT
<213> ORGANISM: Artificial Sequence
<220> FEATURE:
<223> OTHER INFORMATION: Completely synthetic

<400> SEQUENCE: 2

Gly Gly Asp Gly Ala Thr Met Lys Thr Phe Cys Gly Gly Thr Pro Ser
1               5                   10                  15

Asp Gly Asp Pro Asp Gly Gly Glu Phe Thr Glu Phe
            20                  25
``` said alkyl group is optionally substituted with hydroxyl or cyano, and said heterocyclyl group is optionally substituted with halo;

$R^3$ is hydrogen;

$R^5$ is hydrogen, halo, cyano, $C_{1-6}$ alkyl, $(C_{1-6}$ alkyl$)OR^6$, heteroyclyl, $CH_2$-heterocyclyl or $CH_2$-heteroaryl, wherein said alkyl groups are optionally substituted with one to three substituents independently selected from the group consisting of halo, hydroxyl and $NR^6R^7$, and said heterocyclyl groups are optionally substituted on either the carbon or the heteroatom with $C_{1-6}$ alkyl;

$R^6$ is hydrogen or $C_{1-6}$ alkyl, wherein said alkyl group is optionally substituted with hydroxyl or $C_{3-6}$ cycloalkyl;

$R^7$ is hydrogen or $C_{1-6}$ alkyl, wherein said alkyl group is optionally substituted with hydroxyl;

or a pharmaceutically acceptable salt thereof.

2. The compound of claim 1 wherein $R^1$ is aryl, wherein said aryl group is substituted with one to three substituents independently selected from the group consisting of halo and $C_{1-6}$ alkyl, wherein said alkyl group is optionally substituted with hydroxyl; or a pharmaceutically acceptable salt thereof.

3. The compound of claim 2 wherein $R^1$ is phenyl, wherein said phenyl group is substituted with one to three substituents independently selected from the group consisting of halo and $C_{1-6}$ alkyl, wherein said alkyl group is optionally substituted with hydroxyl; or a pharmaceutically acceptable salt thereof.

4. The compound of claim 3 wherein
$R^5$ is $C_{1-6}$ alkyl, wherein said alkyl group is optionally substituted with one to three hydroxyl; or a pharmaceutically acceptable salt thereof.

5. The compound of claim 1 selected from
5-[2,6-Difluoro-4-(1-hydroxy-1-methylethyl)phenyl]-2-{[6-(2-hydroxyethyl)-5-oxo-6,7-dihydro-5H-pyrrolo[3,4-b]pyridin-2-yl]amino}thiophene-3-carboxamide;
5-[2,6-difluoro-4-(1-hydroxy-1-methylethyl)phenyl]-2-[(5-oxo-6,7-dihydro-5H-pyrrolo[3,4-b]pyridin-2-yl)amino]thiophene-3-carboxamide;
5-[2,6-difluoro-4-(1-hydroxy-1-methylethyl)phenyl]-2-{[6-(2-methoxyethyl)-5-oxo-6,7-dihydro-5H-pyrrolo[3,4-b]pyridin-2-yl]amino}thiophene-3-carboxamide;
5-[2,6-difluoro-4-(1-hydroxy-1-methylethyl)phenyl]-2-({6-[(2S)-2-hydroxypropyl]-5-oxo-6,7-dihydro-5H-pyrrolo[3,4-b]pyridin-2-yl}amino)thiophene-3-carboxamide;
5-[2,6-difluoro-4-(1-hydroxy-1-methylethyl)phenyl]-2-({6-[(2R)-2-hydroxypropyl]-5-oxo-6,7-dihydro-5H-pyrrolo[3,4-b]pyridin-2-yl}amino)thiophene-3-carboxamide;
5-[2,6-difluoro-4-(1-hydroxy-1-methylethyl)phenyl]-2-({6-[2-(dimethylamino)ethyl]-5-oxo-6,7-dihydro-5H-pyrrolo[3,4-b]pyridin-2-yl}amino)thiophene-3-carboxamide;
5-[2,6-Difluoro-4-(1-hydroxy-1-methylethyl)phenyl]-2-[(6-methyl-5-oxo-6,7-dihydro-5H-pyrrolo[3,4-b]pyridin-2-yl)amino]thiophene-3-carboxamide;
5-[2-fluoro-4-(1-hydroxy-1-methylethyl)phenyl]-2-[(6-methyl-5-oxo-6,7-dihydro-5H-pyrrolo[3,4-b]pyridin-2-yl)amino]thiophene-3-carboxamide;
5-[4-(1-hydroxy-1-methylethyl)phenyl]-2-[(6-methyl-5-oxo-6,7-dihydro-5H-pyrrolo[3,4-b]pyridin-2-yl)amino]thiophene-3-carboxamide;
2-[(6-methyl-5-oxo-6,7-dihydro-5H-pyrrolo[3,4-b]pyridin-2-yl)amino]-5-(6-morpholin-4-ylpyridin-3-yl)thiophene-3-carboxamide;
5-(4-chlorophenyl)-2-[(6-methyl-5-oxo-6,7-dihydro-5H-pyrrolo[3,4-b]pyridin-2-yl)amino]thiophene-3-carboxamide;
5-(4-fluorophenyl)-2-[(6-methyl-5-oxo-6,7-dihydro-5H-pyrrolo[3,4-b]pyridin-2-yl)amino]thiophene-3-carboxamide;
2-[(6-methyl-5-oxo-6,7-dihydro-5H-pyrrolo[3,4-b]pyridin-2-yl)amino]-5-(2,4,6-trifluorophenyl) thiophene-3-carboxamide;
5-[4-(1-cyano-1-methylethyl)phenyl]-2-[(6-methyl-5-oxo-6,7-dihydro-5H-pyrrolo[3,4-b]pyridin-2-yl)amino]thiophene-3-carboxamide;
5-[4-(3-fluorooxetan-3-yl)phenyl]-2-[(6-methyl-5-oxo-6,7-dihydro-5H-pyrrolo[3,4-b]pyridin-2-yl)amino]thiophene-3-carboxamide;
5-[2,6-difluoro-4-(1-hydroxy-1-methylethyl)phenyl]-2-[(6-isopropyl-5-oxo-6,7-dihydro-5H-pyrrolo[3,4-b]pyridin-2-yl)amino]thiophene-3-carboxamide;
5-[2,6-Difluoro-4-(1-hydroxy-1-methylethyl)phenyl]-2-({6-[(3-methyloxetan-3-yl)methyl]-5-oxo-6,7-dihydro-5H-pyrrolo [3,4-b]pyridin-2-yl}amino)thiophene-3-carboxamide;
5-[2,6-difluoro-4-(1-hydroxy-1-methylethyl)phenyl]-2-{[6-(1,3-oxazol-2-ylmethyl)-5-oxo-6,7-dihydro-5H-pyrrolo[3,4-b]pyridin-2-yl]amino}thiophene-3-carboxamide;
5-[2,6-Difluoro-4-(1-hydroxy-1-methylethyl)phenyl]-2-[(6-oxetan-3-yl-5-oxo-6,7-dihydro-5H-pyrrolo[3,4-b]pyridin-2-yl)amino]thiophene-3-carboxamide;
or a pharmaceutically acceptable salt thereof.

6. A pharmaceutical composition comprising a pharmaceutically effective amount of the compound according to claim 1, and a pharmaceutically acceptable carrier.

* * * * *